(12) United States Patent
Masumoto et al.

(10) Patent No.: US 8,658,459 B2
(45) Date of Patent: Feb. 25, 2014

(54) COMPOUND AND METHOD OF PRODUCING ORGANIC SEMICONDUCTOR DEVICE

(75) Inventors: Akane Masumoto, Yokohama (JP); Toshihiro Kikuchi, Yokohama (JP); Noboru Ono, Matsuyama (JP); Hidemitsu Uno, Matsuyama (JP); Hiroko Nakashima, Matsuyama (JP)

(73) Assignee: Canon Kabushiki Kaisha, Tokyo (JP)

( * ) Notice: Subject to any disclaimer, the term of this patent is extended or adjusted under 35 U.S.C. 154(b) by 271 days.

(21) Appl. No.: 13/049,778

(22) Filed: Mar. 16, 2011

(65) Prior Publication Data

US 2011/0223714 A1    Sep. 15, 2011

Related U.S. Application Data

(62) Division of application No. 11/964,619, filed on Dec. 26, 2007, now Pat. No. 7,928,221.

(30) Foreign Application Priority Data

Dec. 27, 2006 (JP) ................................ 2006-352555
Sep. 6, 2007 (JP) ................................ 2007-232091

(51) Int. Cl.
*H01L 51/40* (2006.01)
*H01L 51/05* (2006.01)
*H01L 51/00* (2006.01)

(52) U.S. Cl.
CPC ........ *H01L 51/0545* (2013.01); *H01L 51/0055* (2013.01); *H01L 51/0056* (2013.01)
USPC ......................... 438/99; 257/40; 257/E51.024

(58) Field of Classification Search
USPC ............... 438/99; 257/40, E51.024, E51.025
See application file for complete search history.

(56) References Cited

U.S. PATENT DOCUMENTS

| | | | |
|---|---|---|---|
| 4,487,667 A * | 12/1984 | Traynor | 528/423 |
| 5,659,181 A | 8/1997 | Bridenbaugh | |
| 7,586,117 B2 | 9/2009 | Masumoto | |
| 2004/0087676 A1 | 5/2004 | Okuyama | |
| 2006/0081880 A1 | 4/2006 | Miyazaki | |
| 2007/0012914 A1* | 1/2007 | Miura et al. | 257/40 |
| 2007/0051947 A1* | 3/2007 | Nakayama et al. | 257/40 |
| 2007/0085072 A1 | 4/2007 | Masumoto | |
| 2007/0244099 A1* | 10/2007 | Rudolf et al. | 514/221 |
| 2008/0308789 A1 | 12/2008 | Miura et al. | |

FOREIGN PATENT DOCUMENTS

| | | |
|---|---|---|
| JP | 5-55568 | 3/1993 |
| JP | 5-190877 | 7/1993 |
| JP | 8-264805 | 10/1996 |
| JP | 2004-107216 | 4/2004 |
| JP | 2004-221318 | 8/2004 |
| JP | 2004-266157 | 9/2004 |

OTHER PUBLICATIONS

Christos D. Dimitrakopoulos, et al., "Organic Thin Film Transistors for Large Area Electronics", Advanced Materials, 2002, pp. 99-117, vol. 14, No. 2.
Eizoh Kawatoh, et al., "Analysis of Sputtered Neutrals by Nonresonant Multiphoton Ionization", Japanese Journal of Applied Physics, 1991, pp. 608-677, vol. 30, No. 3.
H. Sirringhaus, et al., "Two-Dimensional Charge Transport in Self-Organized, High-Mobility Conjugated Polymers", Nature, 1999, pp. 685-688, vol. 401.
A. R. Brown, et al. "Precursor Route Pentacene Metal-Insulator-Semiconductor Field-Effect Transistors", Journal of Applied Physics, 1996, pp. 2136-2138, vol. 79, No. 4.
Nathalie Vets, et al., "Synthesis and Thermolysis of a Diels-Alder Adduct of Pentacene and Thiophosgene", Tetrahedron Letters, 2004, pp. 7287-7289, vol. 45.
Ali Afzali, et al., "Photosensitive Pentacene Precursor: Synthesis, Photothermal Pattering, and Application in Thin-Film Transistors", Advanced Materials, 2003, pp. 2066-2069, vol. 15, No. 24.
Leo A. Paquette, "Organics Reactions", vol. 52, Ed., Apr. 1998, pp. 76-79 and 352-353.

* cited by examiner

*Primary Examiner* — Michael Trinh

(74) *Attorney, Agent, or Firm* — Fitzpatrick, Cella, Harper and Scinto

(57) ABSTRACT

A method of producing an organic semiconductor device is provided in which a layer composed of an organic semiconductor having excellent crystallinity and orientation in a low-temperature region can be formed, and the device can be produced in the air. The method includes forming a layer composed of an organic semiconductor precursor on a base body and irradiating the organic semiconductor precursor with light, wherein the organic semiconductor precursor is a porphyrin compound or an azaporphyrin compound having in its molecule at least one of the structure represented by the following general formula (1) or (2):

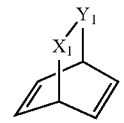

General formula (1)

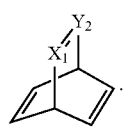

General formula (2)

7 Claims, 4 Drawing Sheets

COMPOUND AND METHOD OF PRODUCING ORGANIC SEMICONDUCTOR DEVICE

This application is a division of application Ser. No. 11/964,619, filed Dec. 26, 2007, now U.S. Pat. No. 7,928,221.

BACKGROUND OF THE INVENTION

1. Field of the Invention

The present invention relates to a novel compound and a method of producing an organic semiconductor device.

2. Description of the Related Art

Development of a thin film transistor using an organic semiconductor has gradually become active since the latter half of 1980s. In recent years, the basic performance of the thin film transistor using the organic semiconductor has exceeded the basic performance of a thin film transistor using amorphous silicon. Each of organic semiconductor materials often has a high affinity for a plastic substrate on which a semiconductor device such as a thin-film field effect transistor (FET) is formed. Therefore, the organic semiconductor materials are each an attractive material for a semiconductor layer in a device of which flexibility or lightweight property is desired. In addition, some of the organic semiconductor materials can each be formed into a film by the application of a solution or a printing method. The use of any such material enables a large-area device to be produced simply at a low cost.

Examples of the organic semiconductor materials heretofore proposed include the following materials. First, the examples include acenes disclosed in Japanese Patent Application Laid-Open No. H05-55568, such as pentacene and tetracene. The examples further include phthalocyanines each containing lead phthalocyanine disclosed in Japanese Patent Application Laid-Open No. H05-190877, and low-molecular-weight compounds such as perylene and a tetracarboxylic acid derivative of perylene. In addition, Japanese Patent Application Laid-Open No. H08-264805 proposes an aromatic oligomer typified by a thiophene hexamer referred to as α-thienyl or sexithiophene, and, furthermore, polymer compounds such as polythiophene, polythienylene vinylene, and poly-p-phenylene vinylene. It should be noted that most of them are described in Advanced Material, 2002, 2nd issue, p. 99 to 117.

Characteristics demanded when a device is produced by using any such compound in the semiconductor layer of the device, such as a non-linear optical characteristic, conductivity, and a semiconductor characteristic, largely depend on not only the purity of the compound as a material for the layer but also the crystallinity and orientation of the material.

By the way, most of low-molecular-weight compounds (such as pentacene) in each of which a π-conjugated system is expanded has high crystallinity, and is insoluble in a solvent. Accordingly, a thin film composed of each of those compounds is formed by employing a vacuum deposition method in most cases. Pentacene is known to show high field effect mobility, but has involved the following problem: pentacene is so instable in the air as to be apt to be oxidized and to deteriorate. In addition, when employing vacuum film formation such as a vacuum deposition method, the merit of an organic semiconductor material is reduced such that a large-area device can be produced from the material at a low cost.

On the other hand, an organic semiconductor using a π-conjugated polymer can be easily formed into a thin film by, for example, a solution application method in many cases. Therefore, the applied development of an organic semiconductor film using a π-conjugated polymer has been advanced because the film is often excellent in moldability ("Japanese Journal of Applied Physics" by the Japan Society of Applied Physics, 1991, vol. 30, p. 610 to 611). The arrangement state of molecular chains in the π-conjugated polymer is known to have a large influence on electrical conductivity. Similarly, it has been reported that the field effect mobility of a π-conjugated polymer field effect transistor greatly depends on the arrangement state of molecular chains in a semiconductor layer ("Nature", Nature Publishing Group, 1999, vol. 401, p. 685-687). However, the arrangement of molecular chains in the π-conjugated polymer is performed during the period from coating with a solution to drying of the solution, so the arrangement state of the molecular chains may vary to a large extent owing to a change in environment and a difference in coating method. Accordingly, the field effect mobility varies depending on a condition under which the solution is applied, so it may be difficult to stably produce the transistor.

In addition, in recent years, an FET has also been reported which uses a film obtained by: forming a thin film composed of a soluble precursor by coating; and converting the precursor into an organic semiconductor by heat treatment or irradiation with light (J. Appl. Phys. vol. 79, 1996, p. 2136, Japanese Patent Application Laid-Open No. 2004-266157, and Japanese Patent Application Laid-Open No. 2004-221318). Pentacene and porphyrin have been reported as examples in which a precursor is converted into an organic semiconductor by heat treatment. However, problems have been raised in that the conversion of the precursor into porphyrin or pentacene requires treatment at high temperature, and eliminated components having large mass must be removed by decompression. Pentacene is cited as an example in which a precursor is converted into an organic semiconductor by irradiation with light. In this case, treatment at high temperature is not required, but a problem is raised in that irradiation with light must be performed in an inert atmosphere.

Further, a dimer of pentacene is a known example of an organic semiconductor into which a precursor can be converted with either of heat and light. However, the dimer has involved the following problem: [4+4] optical dimerization is employed for the dimerization of pentacene, so a skeleton to which the dimer is adaptable is limited (Japanese Patent Application Laid-Open No. 2004-107216).

Further, in Tetrahedron Letters 45 (2004), p. 7287 to 7289, a material having a skeleton represented by the following general formula (12) (hereinafter referred to as "SCO skeleton") is described as a pentacene precursor, and it is described that the pentacene precursor is converted into pentacene by heating. However, in Tetrahedron Letters 45 (2004), p. 7287 to 7289, it is not described that the conversion of the pentacene precursor into pentacene proceeds also with light.

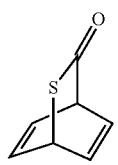

General formula (12)

In addition, in Advanced Materials 15, No. 24 (2003), p. 2066 to 2069 it is described that a pentacene precursor is converted into pentacene by heating. However, in the document, it is described that irradiation with light only results in the polymerization of a substituent of the precursor, so a bicyclo skeleton is maintained, and the conversion of the precursor into pentacene does not occur. The foregoing indicates that an N-sulfinyl group represented by a general formula (14) is converted with heat, but not converted with light:

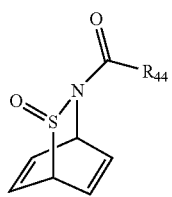

General formula (14)

where $R_{44}$ represents a linear or branched alkyl, alkenyl, alkoxy, alkylthio, alkyl ester, or aryl group, a hydroxyl group, or a halogen atom.

In addition, as reported in Organic Reactions Volume 52, in a skeleton represented by a general formula (15), irradiation with light results in the elimination of ketene to aromatize the remainder, but heating at 180° C. does not cause the elimination. From those examples, it is realized that skeletons are very rare which undergo elimination with either of light and heat in a low-temperature process up to 200° C.

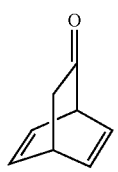

General formula (15)

As described above, in an FET device using an organic semiconductor compound, an organic semiconductor layer having crystallinity and orientation has been conventionally formed through a complicated step such as vacuum film formation.

Even the formation of a film excellent in orientation and crystallinity by a simple method such as a coating method has often required extremely high temperature. In addition, a film that can be formed at low temperature has been poor in stability in the air.

SUMMARY OF THE INVENTION

That is, according to the present invention, a layer composed of an organic semiconductor excellent in crystallinity and orientation in a low-temperature region can be formed, and an organic semiconductor device can be produced in the air. Accordingly, an organic semiconductor device can be easily produced by using any one of various plastic substrates as well as a heat-resistant substrate such as a glass substrate.

In addition, according to the present invention, an organic semiconductor layer can be formed with either of heat and light, so a heat process and a light process can be alternatively employed for forming an organic semiconductor layer from one material depending on the properties of peripheral members.

In addition, a novel compound is provided which can be used in, for example, the afore-mentioned organic semiconductor device.

A semiconductor device obtained by a production method of the present invention can be utilized in, for example, a plastic IC card, an information tag, or a display because the characteristics of the device vary to a small extent, and the device has high durability.

The present invention provides a method of producing an organic semiconductor device having a layer composed of an organic semiconductor, including: forming a layer composed of an organic semiconductor precursor on a base body; and irradiating the organic semiconductor precursor with light, wherein the layer composed of the organic semiconductor precursor contains, as the organic semiconductor precursor, a porphyrin compound or an azaporphyrin compound having in its molecule at least one of a structure represented by the following general formula (1) or (2):

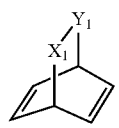

General formula (1)

where $X_1$ and $Y_1$ are each independently one selected from the group consisting of an oxygen atom, a sulfur atom, a carbonyl group, a thiocarbonyl group, $CR_1R_2$, and $NR_3$, wherein $R_1$ to $R_3$ are each independently one selected from the group consisting of a hydrogen atom, linear or branched alkyl, alkenyl, alkoxy, alkylthio, alkyl ester, and aryl groups each having 1 to 12 carbon atoms, and a hydroxyl group, provided that both $X_1$ and $Y_1$ are not $CR_1R_2$ at the same time;

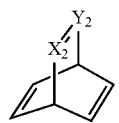

General formula (2)

where $X_2\!=\!Y_2$ is represented by $N\!=\!N$ or $CR_4\!=\!N$ wherein $R_4$ is one selected from the group consisting of a hydrogen atom, linear or branched alkyl, alkenyl, alkoxy, alkylthio, alkyl ester, and aryl groups each having 1 or more to 12 or less carbon atoms, and a hydroxyl group.

The structure represented by the general formula (1) preferably includes a structure represented by any one of the following general formulae (3), (4), and (5).

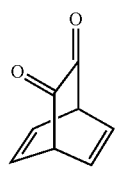

General formula (3)

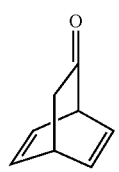

General formula (4)

-continued

General formula (5)

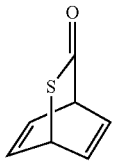

The organic semiconductor precursor preferably includes a compound represented by the following general formula (9):

General formula (9)

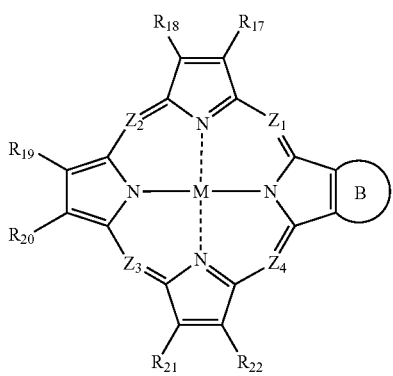

where the B ring is represented by the following general formula (25) or (26), $R_{17}$ to $R_{22}$ are each independently selected from the group consisting of a hydrogen atom, a hydroxyl group, a halogen atom, an alkyl group, an alkoxy group, an alkylthio group, an ester group, an aryl group, a heterocyclic group, and an aralkyl group, $Z_1$ to $Z_4$ are each selected from the group consisting of a nitrogen atom and $CR_{60}$, and may be identical to or different from one another, $R_{60}$ is selected from the group consisting of a hydrogen atom and an aryl group which may have a substituent, M represents two hydrogen atoms, a metal atom, or a metal oxide, and $R_{17}$ and $R_{18}$, $R_{19}$ and $R_{20}$, or $R_{21}$ and $R_{22}$ may be coupled with each other to form the B ring;

General formula (25)

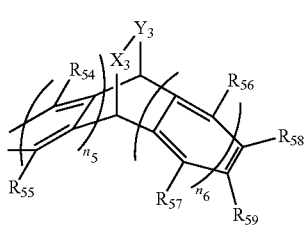

where $X_3$ and $Y_3$ each independently represent one selected from the group consisting of an oxygen atom, a sulfur atom, a carbonyl group, a thiocarbonyl group, $CR_{68}R_{69}$, and $NR_{70}$, wherein $R_{68}$ to $R_{70}$ are each independently selected from the group consisting of a hydrogen atom, linear or branched alkyl, alkenyl, alkoxy, alkylthio, alkyl ester, and aryl groups each having 1 to 12 carbon atoms, and a hydroxyl group, provided that $X_3$ and $Y_3$ are not $CR_{68}R_{69}$ at the same time, $R_{54}$ to $R_{59}$ are each independently selected from the group consisting of a hydrogen atom, an alkyl group, an alkoxy group, an aryl group, a heterocyclic group, an aralkyl group, a phenoxy group, a cyano group, a nitro group, an ester group, a carboxyl group, and a halogen atom, $R_{58}$ and $R_{59}$ may be coupled with each other to form a five-membered heterocyclic ring or a six-membered heterocyclic ring, and $n_5$ and $n_6$ are each independently an integer of 0 or more;

General formula (26)

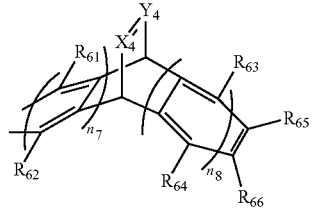

where $X_4=Y_4$ is represented by $N=N$ or $CR_{67}=N$, wherein $R_{67}$ is selected from the group consisting of a hydrogen atom, linear or branched alkyl, alkenyl, alkoxy, alkylthio, alkyl ester, and aryl groups each having 1 to 12 carbon atoms, and a hydroxyl group, $R_{61}$ to $R_{66}$ are each independently selected from the group consisting of a hydrogen atom, an alkyl group, an alkoxy group, an aryl group, a heterocyclic group, an aralkyl group, a phenoxy group, a cyano group, a nitro group, an ester group, a carboxyl group, and a halogen atom, $R_{65}$ and $R_{66}$ may be coupled with each other to form a five-membered heterocyclic ring or a six-membered heterocyclic ring, and $n_7$ and $n_8$ are each independently an integer of 0 or more.

The organic semiconductor precursor preferably has a structure in which the B ring of the general formula (9) is represented by any one of the following general formulae (27), (28), and (29):

General formula (27)

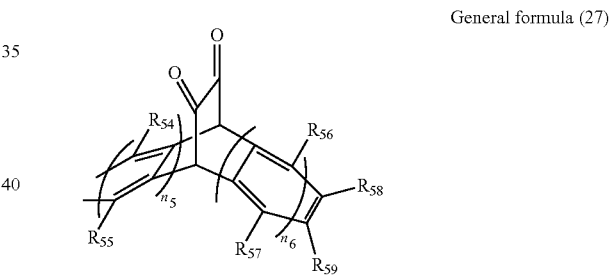

where $R_{54}$ to $R_{59}$ are each independently selected from the group consisting of a hydrogen atom, an alkyl group, an alkoxy group, an aryl group, a heterocyclic group, an aralkyl group, a phenoxy group, a cyano group, a nitro group, an ester group, a carboxyl group, and a halogen atom, $R_{58}$ and $R_{59}$ may be coupled with each other to form a five-membered heterocyclic ring or a six-membered heterocyclic ring, and $n_5$ and $n_6$ are each independently an integer of 0 or more;

General formula (28)

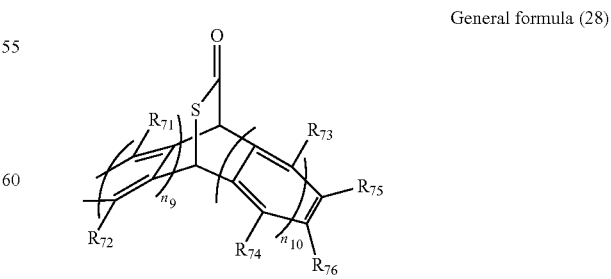

where $R_{71}$ to $R_{76}$ are each independently selected from the group consisting of a hydrogen atom, an alkyl group, an alkoxy group, an aryl group, a heterocyclic group, an aralkyl group, a phenoxy group, a cyano group, a nitro group, an ester group, a carboxyl group, and a halogen atom, $R_{79}$ and $R_{76}$ may be coupled with each other to form a five-membered heterocyclic ring or a six-membered heterocyclic ring, and $n_9$ and $n_{10}$ are each independently an integer of 0 or more;

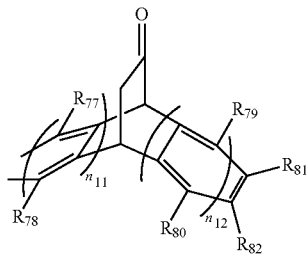

General formula (29)

where $R_{77}$ to $R_{82}$ are each independently selected from the group consisting of a hydrogen atom, an alkyl group, an alkoxy group, an aryl group, a heterocyclic group, an aralkyl group, a phenoxy group, a cyano group, a nitro group, an ester group, a carboxyl group, and a halogen atom, $R_{81}$ and $R_{82}$ may be coupled with each other to form a five-membered heterocyclic ring or a six-membered heterocyclic ring, and $n_{11}$ and $n_{12}$ are each independently an integer of 0 or more.

The organic semiconductor precursor is preferably a compound in which all of $Z_1$ to $Z_4$ of the general formula (9) are each represented by CH, and the B ring of the formula is represented by the general formula (27).

The organic semiconductor precursor preferably includes a compound represented by the following general formula (21):

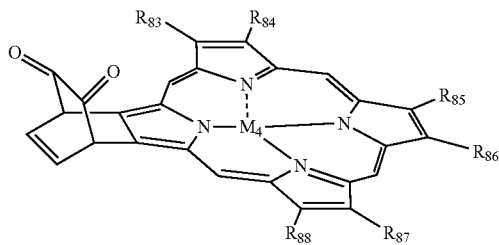

General formula (21)

where $R_{83}$ to $R_{88}$ are each independently selected from the group consisting of a hydrogen atom, a hydroxyl group, a halogen atom, an alkyl group, an alkoxy group, an alkylthio group, an ester group, an aryl group, a heterocyclic group, and an aralkyl group, $M_4$ represents two hydrogen atoms, a metal atom, or a metal oxide, and $R_{83}$ and $R_{84}$, $R_{85}$ and $R_{86}$, or $R_{87}$ and $R_{88}$ may be coupled with each other to form a general formula (30).

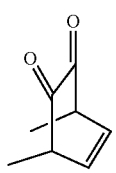

General formula (30)

The irradiation of the organic semiconductor precursor with light is preferably performed while heating the precursor.

The crystallization promoting layer preferably includes a layer containing a polysiloxane compound.

The polysiloxane compound preferably contains a compound having at least a structure represented by the following general formula (6):

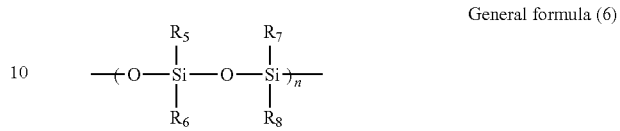

General formula (6)

where $R_5$ to $R_8$ each represent any one of a substituted or unsubstituted alkyl or alkenyl group having 1 to 8 carbon atoms, a substituted or unsubstituted phenyl group, and a siloxane unit, $R_5$ to $R_8$ may be identical to or different from one another, and n represents an integer of 1 or more.

The polysiloxane compound preferably contains a compound having at least a structure represented by the following general formula (7) or (8):

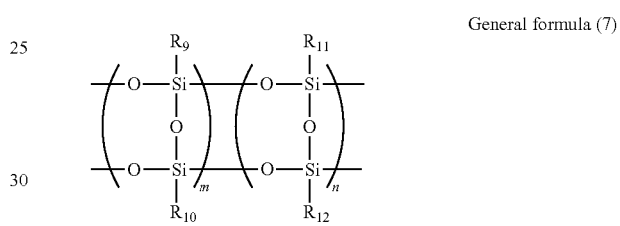

General formula (7)

where $R_9$ to $R_{12}$ each represent one of a substituted or unsubstituted alkyl or alkenyl group having 1 to 8 carbon atoms, and a substituted or unsubstituted phenyl group, $R_9$ to $R_{12}$ may be identical to or different from one another, m and n each independently represent an integer of 0 or more, and the sum of m and n is an integer of 1 or more;

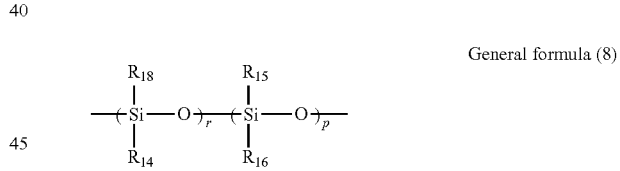

General formula (8)

where $R_{13}$ to $R_{16}$ each represent one of a substituted or unsubstituted alkyl or alkenyl group having 1 to 8 carbon atoms, and a substituted or unsubstituted phenyl group, $R_{13}$ to $R_{16}$ may be identical to or different from one another, r and p each independently represent an integer of 0 or more, and the sum of r and p is an integer of 1 or more.

The organic semiconductor precursor is preferably heated by heating the base body from the outside of the base body.

The formation of the layer composed of the organic semiconductor precursor is preferably performed by applying or printing a solution containing the organic semiconductor precursor on the base body.

In addition, another embodiment of the present invention is a method for producing an organic semiconductor device having a layer composed of an organic semiconductor, including: forming a layer composed of an organic semiconductor precursor on a base body; and subjecting the organic semiconductor precursor to heating and irradiation with light, wherein the layer composed of the organic semiconductor precursor contains, as the organic semiconductor precursor, a compound having in its molecule at least one of a structure represented by the following general formula (12).

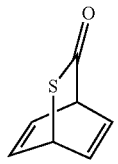

General formula (12)

The layer composed of the organic semiconductor precursor is preferably formed from a solution comprised of the compound having in its molecule at least one of the structure represented by the general formula (12) and an organic solvent containing at least a polar solvent.

The organic semiconductor precursor preferably includes a compound represented by the following general formula (13):

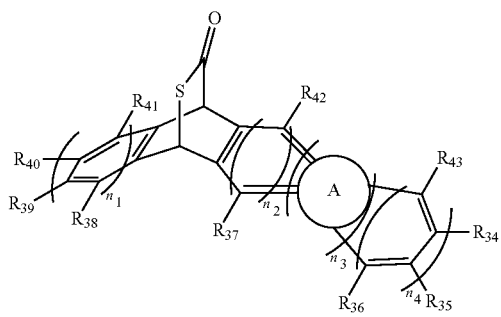

General formula (13)

where the A ring represents one of an SCO skeleton represented by the following general formula (12), a five-membered heterocyclic ring, and a six-membered heterocyclic ring, $R_{37}$ and $R_{42}$ are each independently selected from the group consisting of a hydrogen atom, an alkyl group, an alkoxyl group, an ester group, and a phenyl group, $R_{34}$ to $R_{36}$, $R_{38}$ to $R_{41}$, and $R_{43}$ are each independently selected from the group consisting of a hydrogen atom, an alkyl group, an alkoxyl group, an aryl group, a heterocyclic group, an aralkyl group, a phenoxy group, a cyano group, a nitro group, an ester group, a carboxyl group, and a halogen atom, $R_{34}$ to $R_{36}$, $R_{38}$ to $R_{41}$, and $R_{43}$ may be identical to or different from one another, $R_{34}$ and $R_{35}$, or $R_{39}$ and $R_{40}$ may be coupled with each other to form one of an SCO skeleton, a five-membered heterocyclic ring, and a six-membered heterocyclic ring, and the sum of $n_1$ to $n_4$ represents an integer of 1 or more.

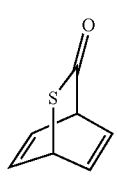

General formula (12)

The compound represented by the general formula (13) preferably includes a compound represented by the following general formula (23).

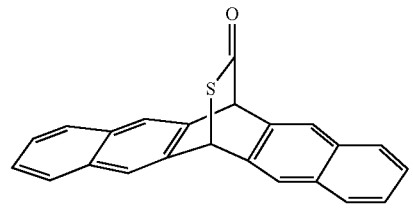

General formula (23)

Further, still another embodiment of the present invention provides a compound which has in its molecule at least one of a structure represented by the following general formula (1) or (2) and has a porphyrin skeleton or an azaporphyrin skeleton.

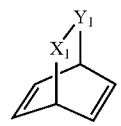

General formula (1)

where $X_1$ and $Y_1$ each independently represent one selected from the group consisting of an oxygen atom, a sulfur atom, a carbonyl group, a thiocarbonyl group, $CR_1R_2$, and $NR_3$, wherein $R_1$ to $R_3$ are each independently selected from the group consisting of a hydrogen atom, linear or branched alkyl, alkenyl, alkoxy, alkylthio, alkyl ester, and aryl groups each having 1 to 12 carbon atoms, and a hydroxyl group, provided that $X_1$ and $Y_1$ are not $CR_1R_2$ at the same time;

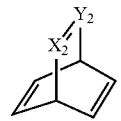

General formula (2)

where $X_2=Y_2$ is represented by $N=N$ or $CR_4=N$, and $R_4$ is selected from the group consisting of a hydrogen atom, linear or branched alkyl, alkenyl, alkoxy, alkylthio, alkyl ester, and aryl groups each having 1 to 12 carbon atoms, and a hydroxyl group.

The structure represented by the general formula (1) preferably includes a structure represented by one of the following general formulae (3), (4), and (5).

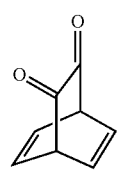

General formula (3)

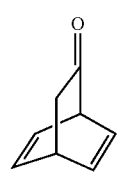

General formula (4)

-continued

General formula (5)

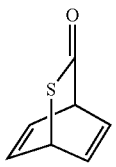

The compound preferably has a structure represented by the following general formula (9).

General formula (9)

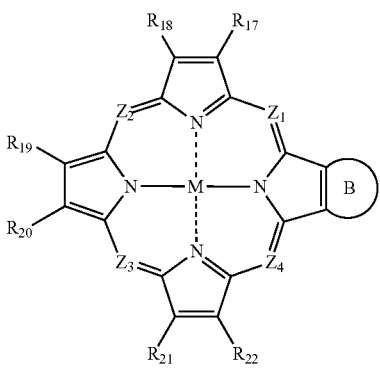

where the B ring is represented by the following general formula (25) or (26), $R_{17}$ to $R_{22}$ are each independently one selected from the group consisting of a hydrogen atom, a hydroxyl group, a halogen atom, an alkyl group, an alkoxy group, an alkylthio group, an ester group, an aryl group, a heterocyclic group, and an aralkyl group, $Z_1$ to $Z_4$ are each selected from the group consisting of a nitrogen atom and $CR_{60}$, and may be identical to or different from one another, wherein $R_{60}$ is one selected from the group consisting of a hydrogen atom and an aryl group which may have a substituent, M represents two hydrogen atoms, a metal atom, or a metal oxide, and each pair of $R_{17}$ and $R_{18}$, $R_{19}$ and $R_{20}$, or $R_{21}$ and $R_{22}$ may be combined together to form the B ring;

General formula (25)

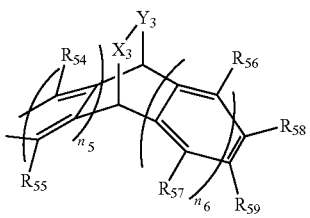

where $X_3$ and $Y_3$ each independently represent one selected from the group consisting of an oxygen atom, a sulfur atom, a carbonyl group, a thiocarbonyl group, $CR_{68}R_{69}$, and $NR_{70}$, $R_{68}$ to $R_{70}$ are each independently one selected from the group consisting of a hydrogen atom, linear or branched alkyl, alkenyl, alkoxy, alkylthio, alkyl ester, and aryl groups each having 1 to 12 carbon atoms, and a hydroxyl group, provided that $X_3$ and $Y_3$ are not $CR_{68}R_{69}$ at the same time, $R_{54}$ to $R_{59}$ are each independently one selected from the group consisting of a hydrogen atom, an alkyl group, an alkoxy group, an aryl group, a heterocyclic group, an aralkyl group, a phenoxy group, a cyano group, a nitro group, an ester group, a carboxyl group, and a halogen atom, $R_{58}$ and $R_{59}$ may be coupled with each other to form a five-membered heterocyclic ring or a six-membered heterocyclic ring, and $n_5$ and $n_6$ each independently represent an integer of 0 or more;

General formula (26)

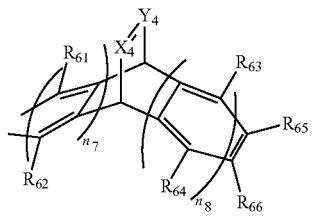

where $X_4$=$Y_4$ is represented by N=N or $CR_{67}$=N, wherein $R_{67}$ is one selected from the group consisting of a hydrogen atom, linear or branched alkyl, alkenyl, alkoxy, alkylthio, alkyl ester, and aryl groups each having 1 to 12 carbon atoms, and a hydroxyl group, $R_{61}$ to $R_{66}$ are each independently one selected from the group consisting of a hydrogen atom, an alkyl group, an alkoxy group, an aryl group, a heterocyclic group, an aralkyl group, a phenoxy group, a cyano group, a nitro group, an ester group, a carboxyl group, and a halogen atom, $R_{65}$ and $R_{66}$ may be coupled with each other to form a five-membered heterocyclic ring or a six-membered heterocyclic ring, and $n_7$ and $n_8$ each independently represent an integer of 0 or more.

The B ring of the general formula (9) preferably has a structure represented by one of the following general formulae (27), (28), and (29):

General formula (27)

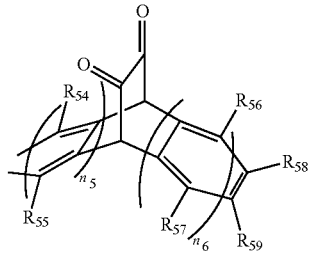

where $R_{54}$ to $R_{59}$ are each independently selected from the group consisting of a hydrogen atom, an alkyl group, an alkoxy group, an aryl group, a heterocyclic group, an aralkyl group, a phenoxy group, a cyano group, a nitro group, an ester group, a carboxyl group, and a halogen atom, $R_{58}$ and $R_{59}$ may be coupled with each other to form a five-membered heterocyclic ring or a six-membered heterocyclic ring, and $n_5$ and $n_6$ each independently represent an integer of 0 or more;

General formula (28)

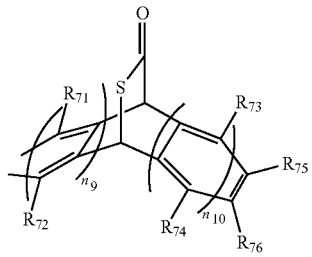

where $R_{71}$ to $R_{76}$ are each independently selected from the group consisting of a hydrogen atom, an alkyl group, an alkoxy group, an aryl group, a heterocyclic group, an aralkyl group, a phenoxy group, a cyano group, a nitro group, an ester group, a carboxyl group, and a halogen atom, $R_{79}$ and $R_{76}$ may be coupled with each other to form a five-membered heterocyclic ring or a six-membered heterocyclic ring, and $n_9$ and $n_{10}$ each independently represent an integer of 0 or more;

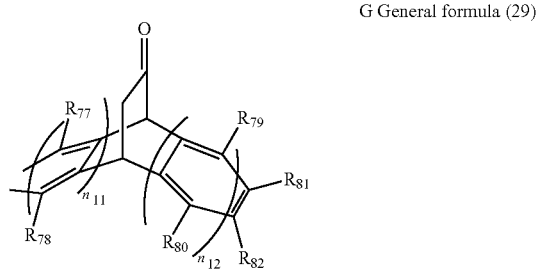

G General formula (29)

where $R_{77}$ to $R_{82}$ are each independently selected from the group consisting of a hydrogen atom, an alkyl group, an alkoxy group, an aryl group, a heterocyclic group, an aralkyl group, a phenoxy group, a cyano group, a nitro group, an ester group, a carboxyl group, and a halogen atom, $R_{81}$ and $R_{82}$ may be coupled with each other to form a five-membered heterocyclic ring or a six-membered heterocyclic ring, and $n_{11}$ and $n_{12}$ each independently represent an integer of 0 or more.

All of $Z_1$ to $Z_4$ of the general formula (9) are preferably represented by CH, and the B ring of the formula is preferably represented by the general formula (27).

All of $Z_1$ to $Z_4$ of the general formula (9) are preferably represented by a nitrogen atom, and the B ring of the formula is preferably represented by the general formula (27).

The compound is preferably represented by the following general formula (21):

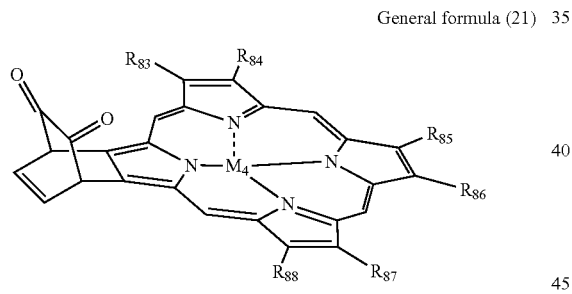

General formula (21)

where $R_{83}$ to $R_{88}$ are each independently selected from the group consisting of a hydrogen atom, a hydroxyl group, a halogen atom, an alkyl group, an alkoxy group, an alkylthio group, an ester group, an aryl group, a heterocyclic group, and an aralkyl group, $M_4$ represents two hydrogen atoms, a metal atom, or a metal oxide, and $R_{83}$ and $R_{84}$, $R_{85}$ and $R_{86}$, or $R_{87}$ and $R_{88}$ may be coupled with each other to form a general formula (30).

General formula (30)

In addition, it is possible to produce a field effect transistor as the semiconductor device.

The present invention comprehends an appropriate combination of the above features.

Further features of the present invention will become apparent from the following description of exemplary embodiments with reference to the attached drawings.

DESCRIPTION OF THE EMBODIMENTS

Figure 1:
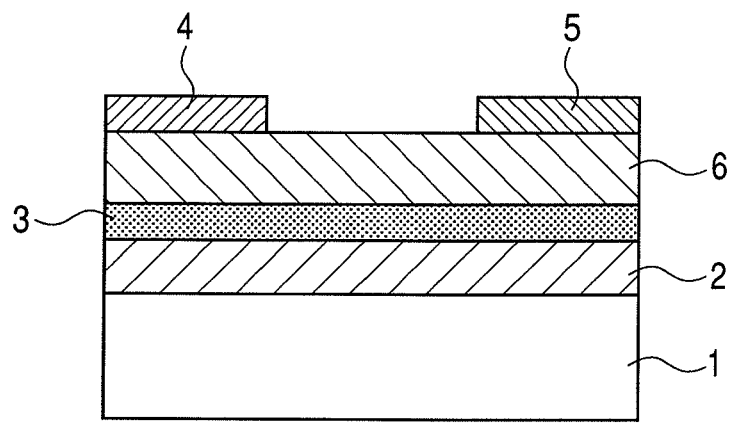
FIG. 1 is a schematic sectional view showing a structure of a top electrode type field effect transistor in Example 1 of the present invention.

Hereinafter, the first and second embodiments of the present invention will be described in detail.

The first embodiment of the present invention provides a method of producing an organic semiconductor device having a layer composed of an organic semiconductor, including: (i) forming a layer composed of an organic semiconductor precursor on a base body; and (ii) irradiating the organic semiconductor precursor with light; and (iii) the layer composed of the organic semiconductor precursor contains, as the organic semiconductor precursor, a porphyrin compound or an azaporphyrin compound having in its molecule at least one of a structure represented by the following general formula (1) or (2):

General formula (1)

where $X_1$ and $Y_1$ each independently represent one selected from the group consisting of an oxygen atom, a sulfur atom, a carbonyl group, a thiocarbonyl group, $CR_1R_2$, and $NR_3$, wherein $R_1$ to $R_3$ are each independently selected from the group consisting of a hydrogen atom, linear or branched alkyl, alkenyl, alkoxy, alkylthio, alkyl ester, and aryl groups each having 1 to 12 carbon atoms, and a hydroxyl group, provided that $X_1$ and $Y_1$ are not $CR_1R_2$ at the same time;

General formula (2)

where $X_2=Y_2$ is represented by $N=N$ or $CR_4=N$, and $R_4$ is selected from the group consisting of a hydrogen atom, linear or branched alkyl, alkenyl, alkoxy, alkylthio, alkyl ester, and aryl groups each having 1 to 12 carbon atoms, and a hydroxyl group.

In addition, the second embodiment of the present invention provides a compound which has in its molecule at least one of a structure represented by the following general formula (1) or (2) and has a porphyrin skeleton or an azaporphyrin skeleton.

Hereinafter, the respective steps possessed by the first embodiment of the present invention, and the second embodiment of the present invention will be described in detail.

Regarding steps (i) and (iii):

In step (i), a layer formed of an organic semiconductor precursor is formed on a base body.

The layer composed of an organic semiconductor precursor includes as the organic semiconductor precursor a porphyrin compound or azaporphyrin compound having in its molecule at least one of the structure represented by the following general formula (1) or (2):

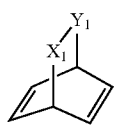

General formula (1)

where $X_1$ and $Y_1$ each independently represent one selected from an oxygen atom, a sulfur atom, a carbonyl group, a thiocarbonyl group, $CR_1R_2$, and $NR_3$, wherein $R_1$ to $R_3$ are each independently selected from a hydrogen atom, linear or branched alkyl, alkenyl, alkoxy, alkylthio, alkyl ester, and aryl groups that have 1 to 12 carbon atoms and may be substituted or unsubstituted, and a hydroxyl group, provided that $X_1$ and $Y_1$ are not $CR_1R_2$ at the same time. Examples of the alkyl group include a methyl group, an ethyl group, a propyl group, an isopropyl group, a butyl group, an isobutyl group, an s-butyl group, and a t-butyl group. Examples of the alkenyl group include a vinyl group and an allyl group. Examples of the alkoxy group include a methoxy group, an ethoxy group, and a propoxy group. Examples of the alkylthio group include a methylthio group and an ethylthio group. Examples of the alkyl ester group include a methyl ester group, an ethyl ester group, a propyl ester group, and a butyl ester group. Examples of the aryl group include a phenyl group and naphthyl group that may have a substituent.

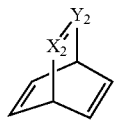

General formula (2)

where $X_2$=$Y_2$ is represented by N=N or $CR_4$=N, and $R_4$ is selected from the group consisting of a hydrogen atom, linear or branched alkyl, alkenyl, alkoxy, alkylthio, alkyl ester, and aryl groups that have 1 to 12 carbon atoms and may be substituted or unsubstituted, and a hydroxyl group. Herein, examples of the alkyl group include a methyl group, an ethyl group, a propyl group, an isopropyl group, a butyl group, an isobutyl group, an s-butyl group, and a t-butyl group. Examples of the alkenyl group include a vinyl group and an allyl group. Examples of the alkoxy group include a methoxy group, an ethoxy group, and a propoxy group. Examples of the alkylthio group include a methylthio group and an ethylthio group. Examples of the alkyl ester group include a methyl ester group, an ethyl ester group, a propyl ester group, and a butyl ester group. Examples of the aryl group include a phenyl group and a naphthyl group that may have a substituent.

It should be noted that the term "porphyrin compound" as used in the present invention refers to a compound having a porphyrin skeleton, and the term "azaporphyrin compound" as used in the present invention refers to a compound having an azaporphyrin skeleton.

In addition, the concept of the term "or" used herein includes "and", so the phrase "A contains B or C" includes a case where A is free from C and contains B, a case where A is free from B and contains C, and a case where A contains B and C.

The porphyrin compound or azaporphyrin compound having a structure represented by the general formula (1) or (2) preferably has a structure represented by one of the following general formulae (3), (4), and (5).

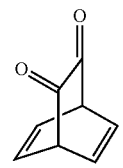

General formula (3)

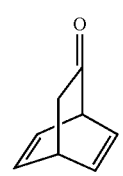

General formula (4)

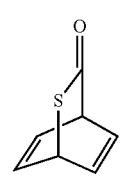

General formula (5)

When an organic semiconductor precursor having as a partial structure bicyclo skeleton represented by the general formula (1) or (2) is irradiated with light (light is applied to the precursor), the bicyclo skeleton undergoes a reverse Diels-Alder reaction with energy obtained by the irradiation. Here, the term "Diels-Alder reaction" refers to an organic chemical reaction in which a double bond referred to as a dienophile is added to a conjugated diene to produce a cyclic structure. The reverse Diels-Alder reaction is a reverse reaction of the Diels-Alder reaction, i.e., a reaction in which the formed cyclic structure is converted into a conjugated diene and dienophile. To be specific, as shown in the following reaction formula (1) or (2), the bicyclo skeleton is converted into an aromatic ring. In conjunction with the conversion, the organic semiconductor precursor is changed to an organic semiconductor.

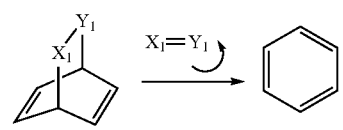

Reaction formula (1)

As shown in the reaction formula (1), the unit $X_1$=$Y_1$ is eliminated from the bicyclo skeleton represented by the general formula (1) with light. In connection with the elimination, the bicyclo skeleton is changed to an aromatic ring. It should be noted that when the unit $X_1$=$Y_1$ is an instable structure, the unit $X_1$=$Y_1$ may be further converted into a stable structure. Accordingly, $X_1$ and $Y_1$ are selected depending on whether the unit $X_1\!=\!Y_1$ can be eliminated with light. $X_1$ and $Y_1$ represent at least one selected from an oxygen atom, a sulfur atom, a carbonyl group, a thiocarbonyl group, $CR_1R_2$, and $NR_3$, wherein $R_1$ to $R_3$ each independently represent one selected from a hydrogen atom, linear or branched alkyl, alkenyl, alkoxy, alkylthio, alkyl ester, and aryl groups each having 1 to 12 carbon atoms, and a hydroxyl group, provided that $X_1$ and $Y_1$ are not $CR_1R_2$ at the same time. Examples of the alkyl group include a methyl group, an ethyl group, a propyl group, an isopropyl group, a butyl group, an isobutyl group, an s-butyl group, and a t-butyl group. Examples of the alkenyl group include a vinyl group and an allyl group. Examples of the alkoxy group include a methoxy group, an ethoxy group, and a propoxy group. Examples of the alkylthio group include a methylthio group and an ethylthio group. Examples of the alkyl ester group include a methyl ester group, an ethyl ester group, a propyl ester group, and a butyl ester group. The aryl group is, for example, a phenyl group which may have a substituent. When the number of carbon atoms of $R_3$ exceeds 12, the molecular weight of the eliminated component increases, so the component remains in the produced organic semiconductor in some cases. In such cases, a sufficient semiconductor characteristic cannot be obtained. In addition, the number of carbon atoms of $R_3$ is more preferably 6 or less.

Reaction formula (2)

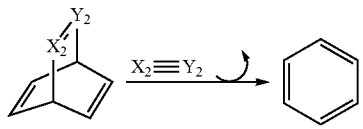

As shown in the reaction formula (2), the unit $X_2\!=\!Y_2$ is eliminated from the bicyclo skeleton represented by the general formula (2) with light. In conjunction with the elimination, the bicyclo skeleton is changed to an aromatic ring. It should be noted that when the unit $X_2\!=\!Y_2$ is an instable structure, the unit $X_2\!=\!Y_2$ may be further converted into a stable structure. Accordingly, $X_2$ and $Y_2$ are selected depending on whether the unit $X_2\!=\!Y_2$ can be eliminated with light. $X_2$ and $Y_2$ each preferably represent a nitrogen atom.

It should be noted that an organic semiconductor precursor having as a partial structure an SCO skeleton represented by the general formula (5) undergoes a reverse Diels-Alder reaction with either of heat energy and light energy. To be specific, as shown in a reaction formula (3), the SCO skeleton is converted into an aromatic ring. In conjunction with the transformation, the organic semiconductor precursor is changed into an organic semiconductor.

Reaction formula (3)

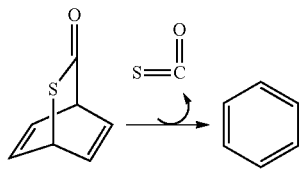

Examples of the porphyrin compound or azaporphyrin compound having a structure represented by the general formula (1) or (2) include compounds represented by the following general formula (9):

General formula (9)

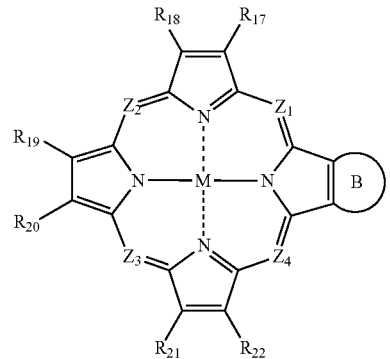

where: the B ring is represented by the general formula (25) or (26) described below; $R_{17}$ to $R_{22}$ each are selected from a hydrogen atom, a linear or branched alkyl group, alkenyl group, alkoxy group, alkylthio group, alkylester group, and aryl group that are substituted or unsubstituted and have 1 to 12 carbon atoms, a hydroxyl group, a hydrogen atom, a heterocyclic group and an aralkyl group, and $R_{17}$ to $R_{22}$ are the same or different from each other; examples of the alkyl group include a methyl group, an ethyl group, a propyl group, an isopropyl group, a butyl group, an isobutyl group, an s-butyl group, and a t-butyl group; examples of the alkenyl group include a vinyl group and an allyl group; examples of the alkoxy group include a methoxy group, an ethoxy group, and a propoxy group; examples of the alkylthio group include a methylthio group and an ethylthio group; examples of the alkyl ester group include a methyl ester group, an ethyl ester group, a propyl ester group, and a butyl ester group; examples of the aryl group include a phenyl group and naphthyl group that may have a substituent; examples of the heterocyclic ring group include a monocylclic heterocyclic ring such as a monovalent pyridine ring, pyradine ring, pyrimidine ring, pyridazine ring, pyrrole ring, imidazole ring, pyrazole ring, furan ring, thiophene ring, oxazole ring, isoxazole ring, thiazole ring, isothiazole ring, furazan ring, and selenophene ring, and silole ring that may have a substituent, and a fused heterocyclic ring group in which a monocyclic heterocyclic ring and an aromatic hydrocarbon ring are arbitrarily combined and fused; examples of the aralkyl group include a benzyl group, a phenylethyl group, and a phenethyl group; $Z_1$ to $Z_4$ are selected from a nitrogen atom or $CR_{60}$, and $Z_1$ to $Z_4$ are the same or different from each other; $R_{60}$ is selected from a hydrogen atom and aryl groups such as a phenyl group and naphthyl group that may have a substituent; M is not particularly limited as long as M represents two hydrogen atoms, a metal atom, or a metal oxide; examples of the metal include copper, gold, silver, zinc, nickel, chromium, magnesium, and lithium. Examples of the metal oxide include TiO and VO. M represents particularly preferably two hydrogen atoms or a copper atom; each pair of $R_{17}$ and $R_{18}$, $R_{19}$ and $R_{20}$, and $R_{21}$ and $R_{22}$ are combined together to form the B ring.

General formula (25)

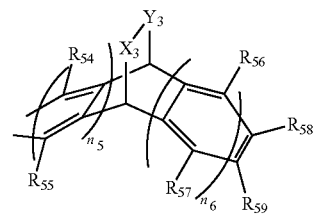

where $X_3$ and $Y_3$ each independently represent at least one selected from the group consisting of an oxygen atom, a sulfur atom, a carbonyl group, a thiocarbonyl group, $CR_{68}R_{69}$, and $NR_{70}$, $R_{68}$ to $R_{70}$ are each independently selected from the group consisting of a hydrogen atom, linear or branched alkyl, alkenyl, alkoxy, alkylthio, alkyl ester, and aryl groups each having 1 to 12 carbon atoms, and a hydroxyl group, provided that $X_3$ and $Y_3$ are not $CR_{68}R_{69}$ at the same time. Examples of the alkyl group include a methyl group, an ethyl group, a propyl group, an isopropyl group, a butyl group, an isobutyl group, an s-butyl group, and a t-butyl group; examples of the alkenyl group include a vinyl group and an allyl group; examples of the alkoxy group include a methoxy group, an ethoxy group, and a propoxy group; examples of the alkylthio group include a methylthio group and an ethylthio group; examples of the alkyl ester group include a methyl ester group, an ethyl ester group, a propyl ester group, and a butyl ester group; examples of the aryl group include a phenyl group and naphthyl group that may have a substituent. $R_{54}$ to $R_{59}$ are each independently selected from the group consisting of a hydrogen atom, an alkyl group, an alkoxy group, an aryl group, a heterocyclic group, an aralkyl group, a phenoxy group, a cyano group, a nitro group, an ester group, a carboxyl group, and a halogen atom. Examples of the alkyl group include a methyl group, an ethyl group, a propyl group, an isopropyl group, a butyl group, an isobutyl group, an s-butyl group, and a t-butyl group; examples of the alkoxy group include a methoxy group, an ethoxy group, and a propoxy group; examples of the ester group include a methyl ester group and an ethyl ester group, a propyl ester group, and a butyl ester group; examples of the aryl group include a phenyl group and naphthyl group that may have a substituent; examples of the heterocyclic ring group include a monocyclic heterocyclic ring group such as a monovalent pyridine ring, pyradine ring, pyrimidine ring, pyridazine ring, pyrrole ring, imidazole ring, pyrazole ring, furan ring, thiophene ring, oxazole ring, isoxazole ring, thiazole ring, isothiazole ring, furazan ring, and selenophene ring, and silole ring that may have a substituent, and a fused heterocyclic ring group in which a monocyclic heterocyclic ring and an aromatic hydrocarbon ring are arbitrarily combined and fused; examples of the aralkyl group include a benzyl group, a phenylethyl group, and a phenethyl group. $R_{58}$ and $R_{59}$ may be coupled with each other to form a five-membered heterocyclic ring or a six-membered heterocyclic ring. Herein, examples of the five-membered or six membered heterocyclic ring include a pyridine ring, a pyradine ring, a pyrimidine ring, a pyridazine ring, a pyrrole ring, an imidazole ring, a pyrazole ring, a furan ring, a thiophene ring, an oxazole ring, an isoxazole ring, a thiazole ring, an isothiazole ring, a furazan ring, a selenophene ring, and a silole ring. $n_5$ and $n_6$ each independently represent an integer of 0 or more.

aryl groups each having 1 to 12 carbon atoms. Herein, examples of the alkyl group include a methyl group, an ethyl group, a propyl group, an isopropyl group, a butyl group, an isobutyl group, an s-butyl group, and a t-butyl group; examples of the alkenyl group include a vinyl group and an allyl group; examples of the alkoxy group include a methoxy group, an ethoxy group, and a propoxy group; examples of the alkylthio group include a methylthio group and an ethylthio group; examples of the alkyl ester group include a methyl ester group, an ethyl ester group, a propyl ester group, and a butyl ester group; examples of the aryl group include a phenyl group and naphthyl group that may have a substituent. $R_{61}$ to $R_{66}$ are each independently selected from the group consisting of a linear or branched alkyl group, alkoxy group, aryl group, heterocyclic group, aralkyl group, and phenoxy group that have 1 to 12 carbon atoms and may be substituted or unsubstituted, a cyano group, a nitro group, an ester group, a carboxyl group, and a halogen atom. Examples of the alkyl group include a methyl group, an ethyl group, a propyl group, an isopropyl group, a butyl group, an isobutyl group, an s-butyl group, and a t-butyl group; examples of the alkoxy group include a methoxy group, an ethoxy group, and a propoxy group; examples of the ester group include a methyl ester group, an ethyl ester group, a propyl ester group, and a butyl ester group; examples of the aryl group include a phenyl group and naphthyl group that may have a substituent; examples of the heterocyclic ring group include a monocyclic heterocyclic ring group such as a monovalent pyridine ring, pyradine ring, pyrimidine ring, pyridazine ring, pyrrole ring, imidazole ring, pyrazole ring, furan ring, thiophene ring, oxazole ring, isoxazole ring, thiazole ring, isothiazole ring, furazan ring, and selenophene ring, and silole ring that may have a substituent, and a fused heterocyclic ring group in which a monocyclic heterocyclic ring and an aromatic hydrocarbon ring are arbitrarily combined and fused; examples of the aralkyl group include a benzyl group, a phenylethyl group, and a phenethyl group. $R_{65}$ and $R_{66}$ may be coupled with each other to form a five-membered heterocyclic ring or a six-membered heterocyclic ring. Examples of the five-membered or six membered heterocyclic ring include a pyridine ring, a pyradine ring, a pyrimidine ring, a pyridazine ring, a pyrrole ring, an imidazole ring, a pyrazole ring, a furan ring, a thiophene ring, an oxazole ring, an isoxazole ring, a thiazole ring, an isothiazole ring, a furazan ring, a selenophene ring, and a silole ring. $n_7$ and $n_8$ each independently represent an integer of 0 or more.

Of those structures, the B ring of the general formula (9) is preferably a structure represented by one of the following general formulae (27), (28), and (29) in consideration of, for example, an influence of the remaining of components that are to be eliminated with light on semiconductor characteristics:

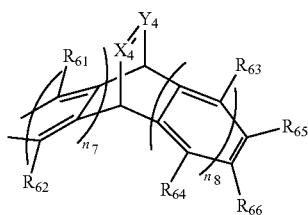

General formula (26)

where $X_4=Y_4$ is represented by $N=N$ or $CR_{67}=N$, $R_{67}$ is selected from the group consisting of a hydrogen atom, linear or branched alkyl, alkenyl, alkoxy, alkylthio, alkyl ester, and

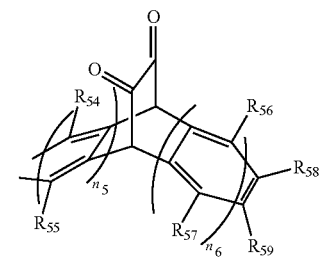

General formula (27)

where $R_{54}$ to $R_{59}$ are each independently selected from the group consisting of a hydrogen atom, an alkyl group, an alkoxy group, an aryl group, a heterocyclic group, an aralkyl group, a phenoxy group, a cyano group, a nitro group, an ester group, a carboxyl group, and a halogen atom. Examples of the alkyl group include a methyl group, an ethyl group, a propyl group, an isopropyl group, a butyl group, an isobutyl group, an s-butyl group, and a t-butyl group; examples of the alkoxy group include a methoxy group, an ethoxy group, and a propoxy group; examples of the ester group include a methyl ester group, an ethyl ester group, a propyl ester group, and a butyl ester group; examples of the aryl group include a phenyl group and naphthyl group that may have a substituent; examples of the heterocyclic ring group include a monocyclic heterocyclic ring group such as a monovalent pyridine ring, pyradine ring, pyrimidine ring, pyridazine ring, pyrrole ring, imidazole ring, pyrazole ring, furan ring, thiophene ring, oxazole ring, isoxazole ring, thiazole ring, isothiazole ring, furazan ring, and selenophene ring, and silole ring that may have a substituent, and fused heterocyclic ring group in which a monocyclic heterocyclic ring and an aromatic hydrocarbon ring are arbitrarily combined and fused; examples of the aralkyl group include a benzyl group, a phenylethyl group, and a phenethyl group. $R_{58}$ and $R_{59}$ may be coupled with each other to form a five-membered heterocyclic ring or a six-membered heterocyclic ring. Examples of the five-membered or six membered heterocyclic ring include a pyridine ring, a pyradine ring, a pyrimidine ring, a pyridazine ring, a pyrrole ring, an imidazole ring, a pyrazole ring, a furan ring, a thiophene ring, an oxazole ring, an isoxazole ring, a thiazole ring, an isothiazole ring, a furazan ring, a selenophene ring, and a silole ring. $n_5$ and $n_6$ each independently represent an integer of 0 or more.

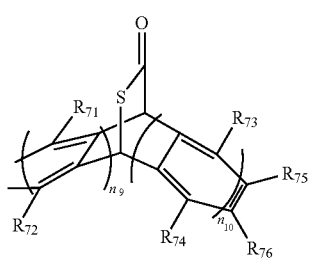

General formula (28)

where $R_{71}$ to $R_{76}$ are each independently selected from the group consisting of a hydrogen atom, an alkyl group, an alkoxy group, an aryl group, a heterocyclic group, an aralkyl group, a phenoxy group, a cyano group, a nitro group, an ester group, a carboxyl group, and a halogen atom. Examples of the alkyl group include a methyl group, an ethyl group, a propyl group, an isopropyl group, a butyl group, an isobutyl group, an s-butyl group, and a t-butyl group; examples of the alkoxy group include a methoxy group, an ethoxy group, and a propoxy group; examples of the ester group include a methyl ester group, an ethyl ester group, a propyl ester group, and a butyl ester group; examples of the aryl group include a phenyl group and naphthyl group that may have a substituent; examples of the heterocyclic ring group include a monocyclic heterocyclic ring group such as a monovalent pyridine ring, pyradine ring, pyrimidine ring, pyridazine ring, pyrrole ring, imidazole ring, pyrazole ring, furan ring, thiophene ring, oxazole ring, isoxazole ring, thiazole ring, isothiazole ring, furazan ring, and selenophene ring, and silole ring that may have a substituent, and a fused heterocyclic ring group in which a monocyclic heterocyclic ring and an aromatic hydrocarbon ring are arbitrarily combined and fused; examples of the aralkyl group include a benzyl group, a phenylethyl group, and a phenethyl group. $R_{75}$ and $R_{76}$ may be coupled with each other to form a five-membered heterocyclic ring or a six-membered heterocyclic ring. Examples of the five-membered or six membered heterocyclic ring include a pyridine ring, a pyradine ring, a pyrimidine ring, a pyridazine ring, a pyrrole ring, an imidazole ring, a pyrazole ring, a furan ring, a thiophene ring, an oxazole ring, an isoxazole ring, a thiazole ring, an isothiazole ring, a furazan ring, a selenophene ring, and a silole ring. $n_9$ and $n_{10}$ each independently represent an integer of 0 or more;

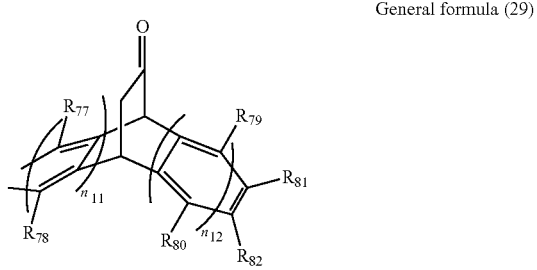

General formula (29)

where $R_{77}$ to $R_{82}$ are each independently selected from the group consisting of a hydrogen atom, an alkyl group, an alkoxy group, an aryl group, a heterocyclic group, an aralkyl group, a phenoxy group, a cyano group, a nitro group, an ester group, a carboxyl group, and a halogen atom. Examples of the alkyl group include a methyl group, an ethyl group, a propyl group, an isopropyl group, a butyl group, an isobutyl group, an s-butyl group, and a t-butyl group; examples of the alkoxy group include a methoxy group, an ethoxy group, and a propoxy group; examples of the ester group include a methyl ester group, an ethyl ester group, a propyl ester group, and a butyl ester group; examples of the aryl group include a phenyl group and naphthyl group that may have a substituent; examples of the heterocyclic ring group include a monocyclic heterocyclic ring such as a monovalent pyridine group, pyradine group, pyrimidine group, pyridazine group, pyrrole group, imidazole group, pyrazole group, furan group, thiophene group, oxazole group, isoxazole group, thiazole group, isothiazole group, furazan group, and selenophene group, and silole group that may have a substituent, and a fused heterocyclic ring group in which a monocyclic heterocyclic ring having a single ring and an aromatic hydrocarbon ring are arbitrarily combined and fused; examples of the aralkyl group include a benzyl group, a phenylethyl group, and a phenethyl group. $R_{81}$ and $R_{82}$ may be coupled with each other to form a five-membered heterocyclic ring or a six-membered heterocyclic ring. Examples of the five-membered or six membered heterocyclic ring include a pyridine ring, a pyradine ring, a pyrimidine ring, a pyridazine ring, a pyrrole ring, an imidazole ring, a pyrazole ring, a furan ring, a thiophene ring, an oxazole ring, an isoxazole ring, a thiazole ring, an isothiazole ring, a furazan ring, a selenophene ring, and a silole ring. $n_{11}$ and $n_{12}$ each independently represent an integer of 0 or more.

Of those structures, a more preferred example includes a compound in which all of $Z_1$ to $Z_4$ of the general formula (9) are represented by CH, and the B ring of the formula is represented by the general formula (27), or all of $Z_1$ to $Z_4$ of the general formula (9) are represented by a nitrogen atom, and the B ring of the formula is represented by the general formula (27).

A method of synthesizing those compounds is not limited, but the compounds can be synthesized by, for example, the following synthesis method.

A porphyrin ring in a compound in which all of $Z_1$ to $Z_4$ of the general formula (9) are represented by CH, and the B ring of the formula is represented by the general formula (27) can be formed by, for example, a method shown in reaction formulae (4) to (7), whereby a porphyrin compound having 1 to 4 B rings can be synthesized.
Reaction formula (4)
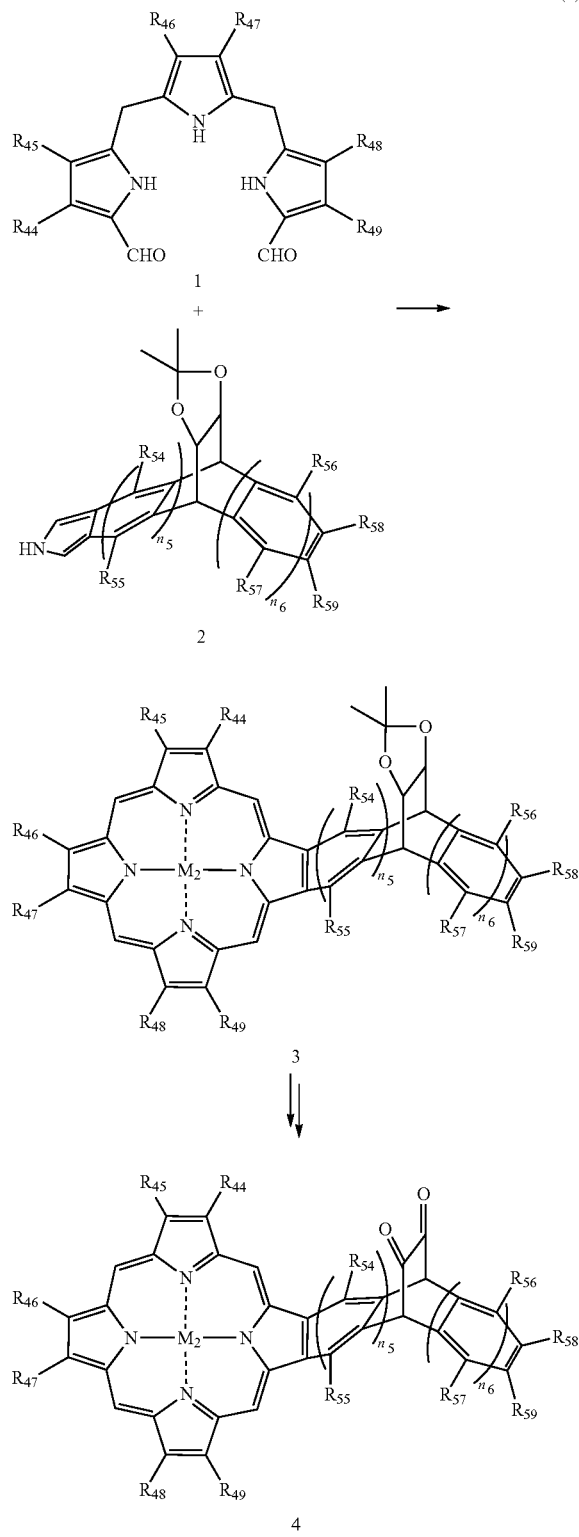
Reaction formula (5)
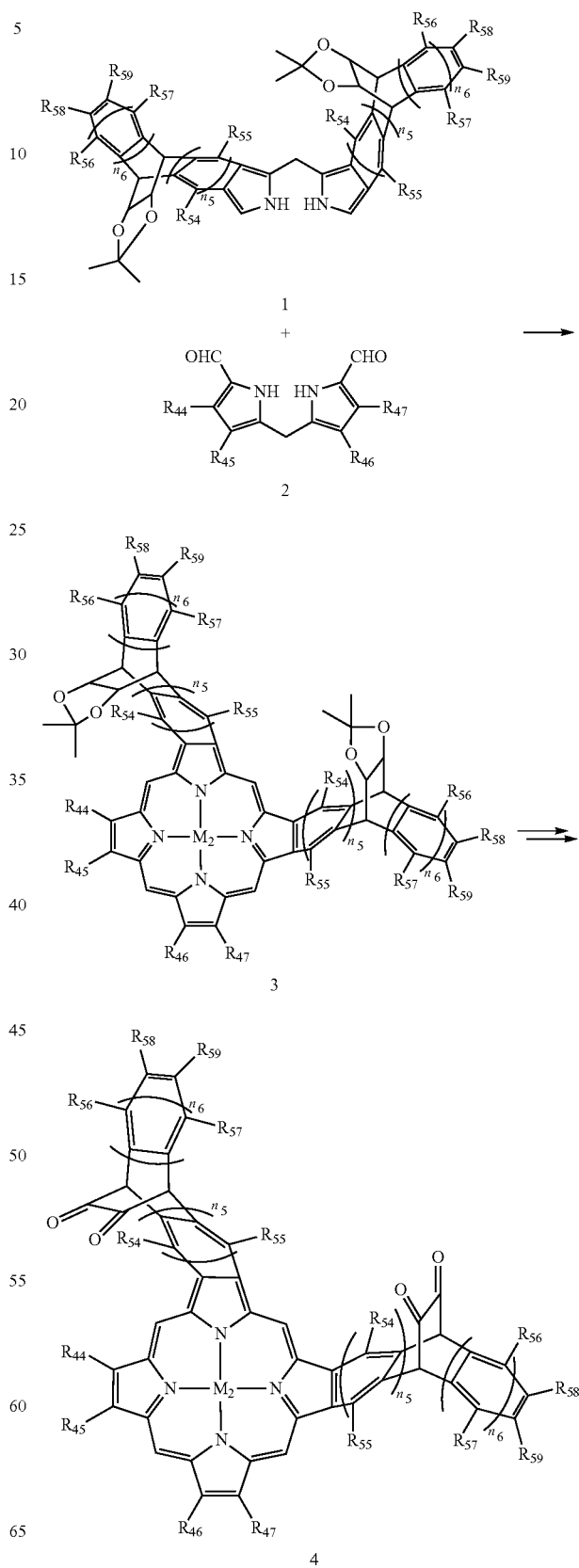

Reaction formula (6)
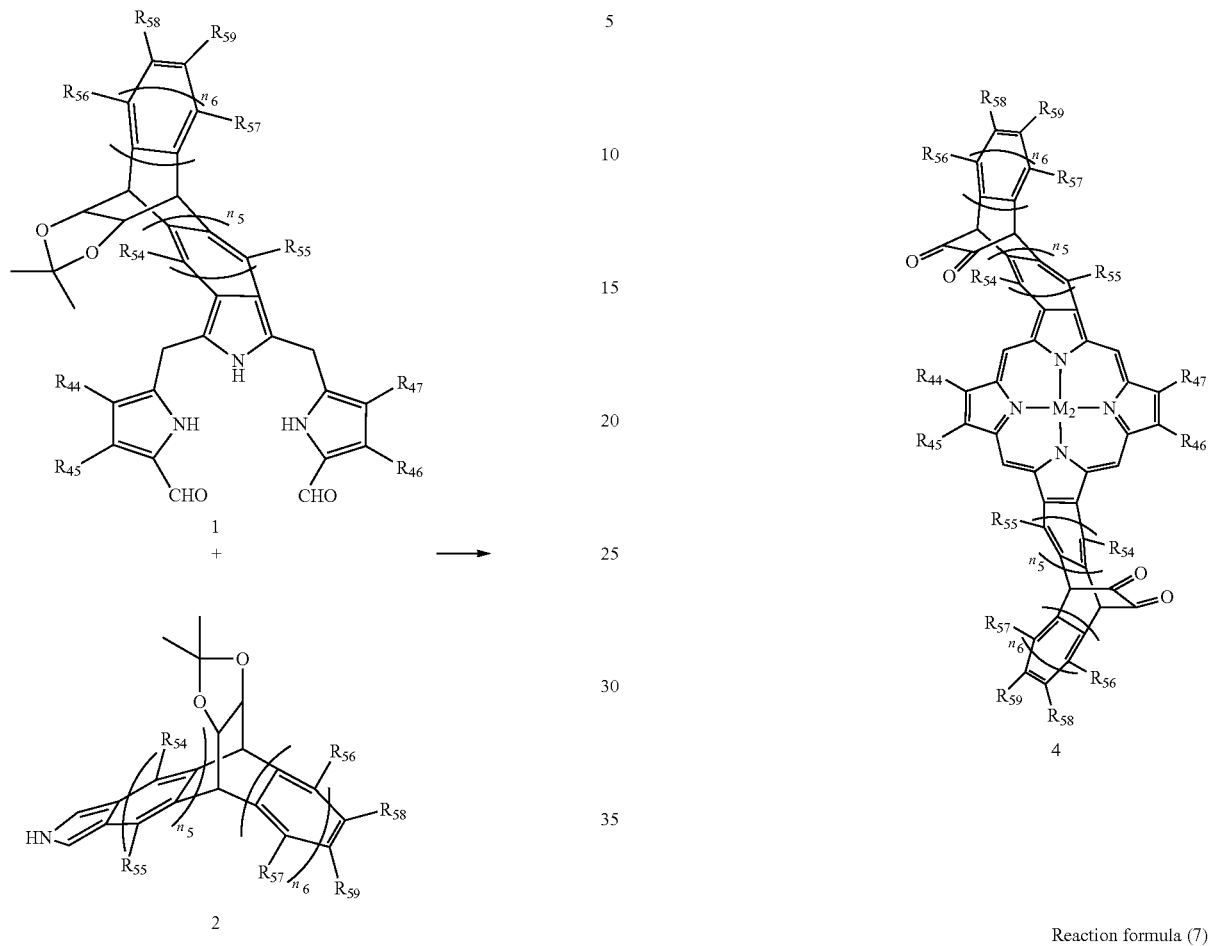
Reaction formula (7)
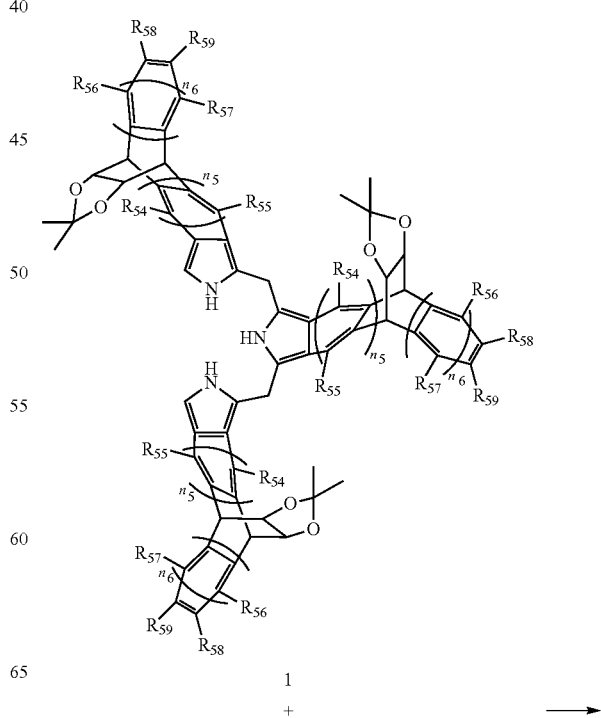

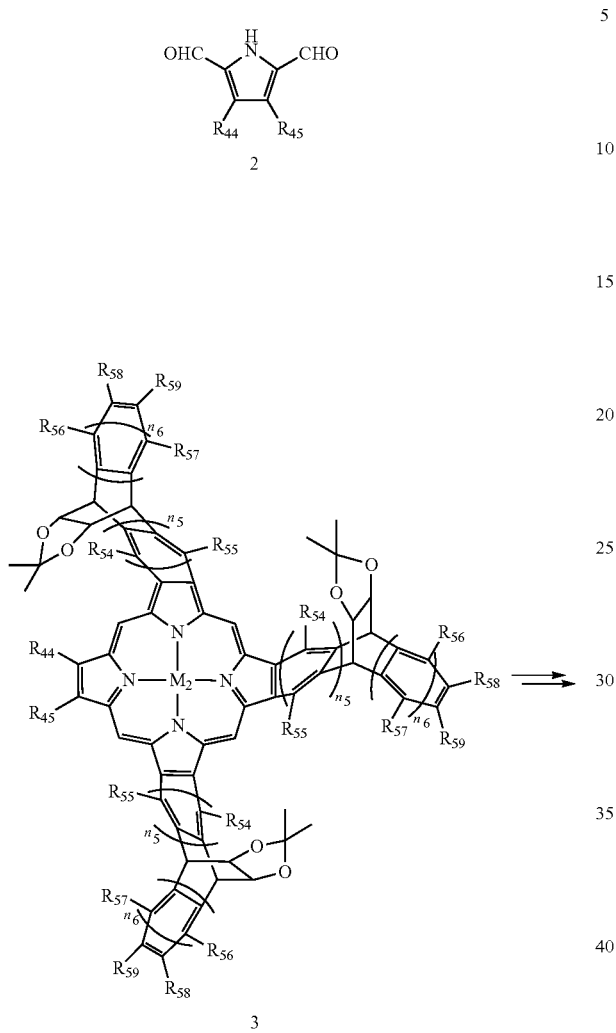

3

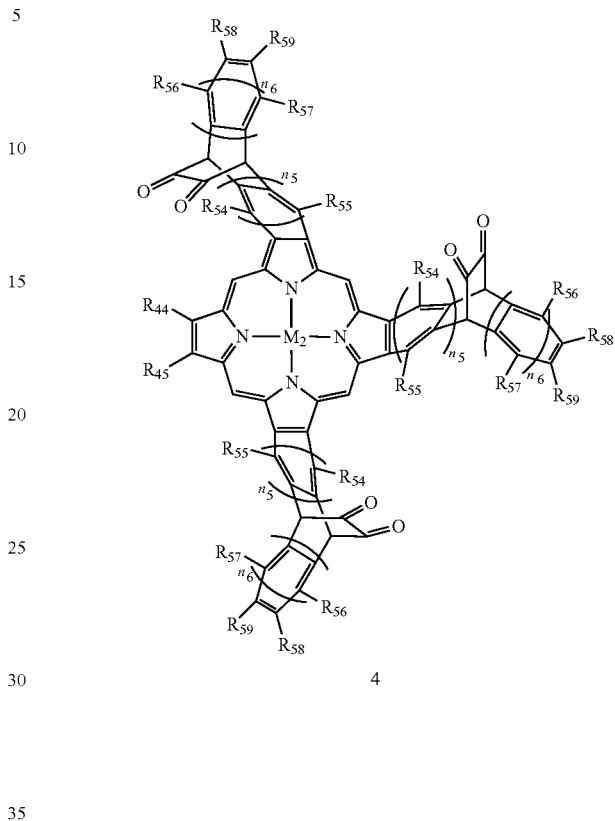

4

In each of the reaction formulae (4) to (7), Compound (4) having 1 to 3 B rings can be synthesized by: condensing Compound (1) and Compound (2) in the presence of an acid catalyst such as trichloroacetic acid; subjecting the condensate to an oxidation reaction to produce Compound (3); forming a diol body by deprotection with an acid such as hydrochloric acid; and subjecting the diol body to an oxidation reaction such as Swern oxidation.

General formula (8)

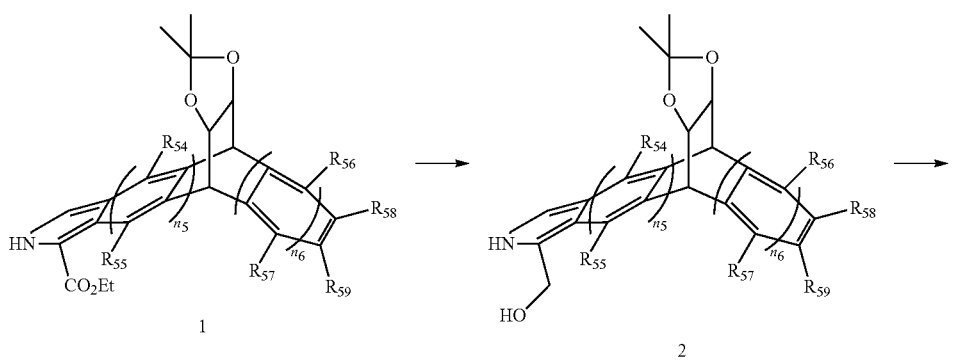

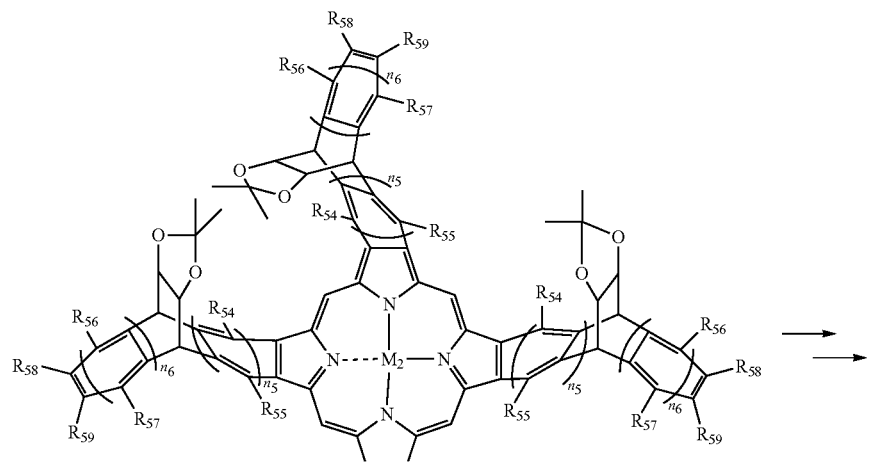
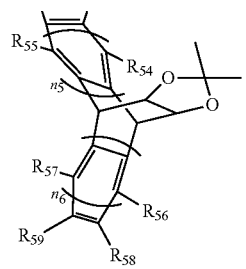
3
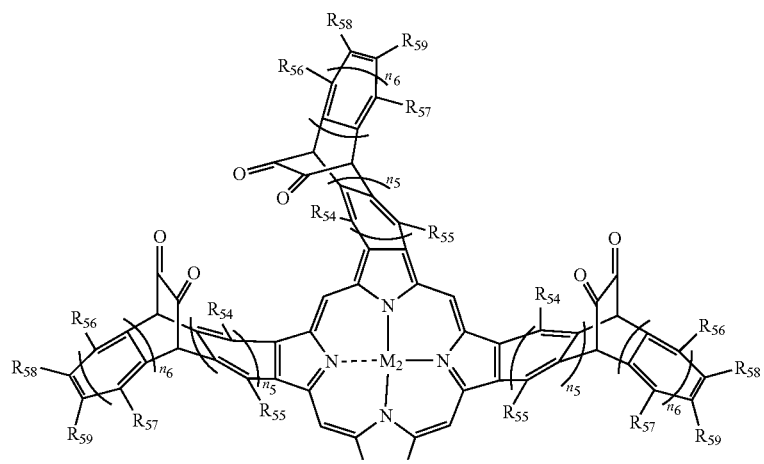
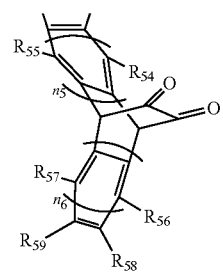
4

As shown in the reaction formula (8), Compound (3) can be obtained by: reducing Compound (1) to produce Compound (2); and turning Compound (2) into a tetrameric ring in the presence of an acid catalyst. Compound (4) having 4 B rings can be synthesized by deprotection and oxidation of Compound (3) thus obtained.

In addition, a substituent can be introduced to a meso-position by allowing a compound in which a hydrogen atom is present at α-position of pyrrole, dipyrromethane, or tripyrane at the time of a cyclization reaction to react with various aldehydes in the presence of an acid catalyst.

In addition, when a metal is coordinated at the center of the porphyrin ring, any method may be used, but a method involving causing a metal acetate or the like to act on a non-metal body is preferable.

Pyrroles having various substituents at the β-positions can be used as constitutional units of such porphyrin compound as described above. The pyrroles having various substituents at the β-positions can be synthesized by employing a method typified by a Barton-Zard method or a Knorr method. In addition, a raw material for the porphyrin compound such as dipyrromethane or tripyrane can be synthesized by appropriately combining those pyrroles.

In addition, while there is no specific limitation concerning methods of synthesizing pyrroles each having a group that can be converted into the B ring, an acetonide-protected body is suitably used as a group that can be converted into the B ring, and each pyrrole can be synthesized by, for example, such method as shown in reaction formulae (9) to (11).

As shown in the reaction formula (9), pyrrole can be synthesized by a Diels-Alder reaction of cyclohexadiene with bissulfonylethylene, and, subsequently, a Barton-Zard method. In addition, a substituent at α-position can be converted as shown in Route 1 for decarboxylation or Route 2 for reduction.

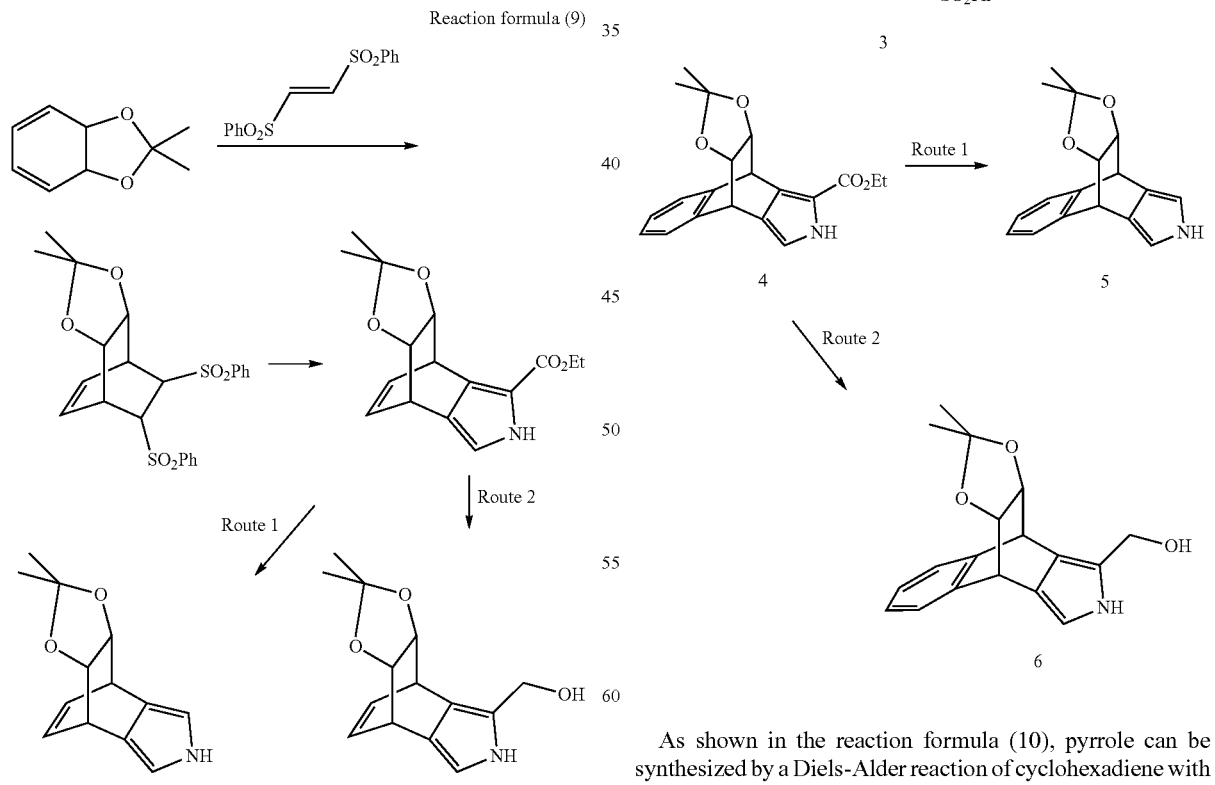

As shown in the reaction formula (10), pyrrole can be synthesized by a Diels-Alder reaction of cyclohexadiene with benzyne, and, subsequently, addition of PhSCl, an oxidation reaction, and a Barton-Zard method. In addition, a substituent at α-position can be converted as shown in Route 1 or Route 2.

Reaction formula (11)

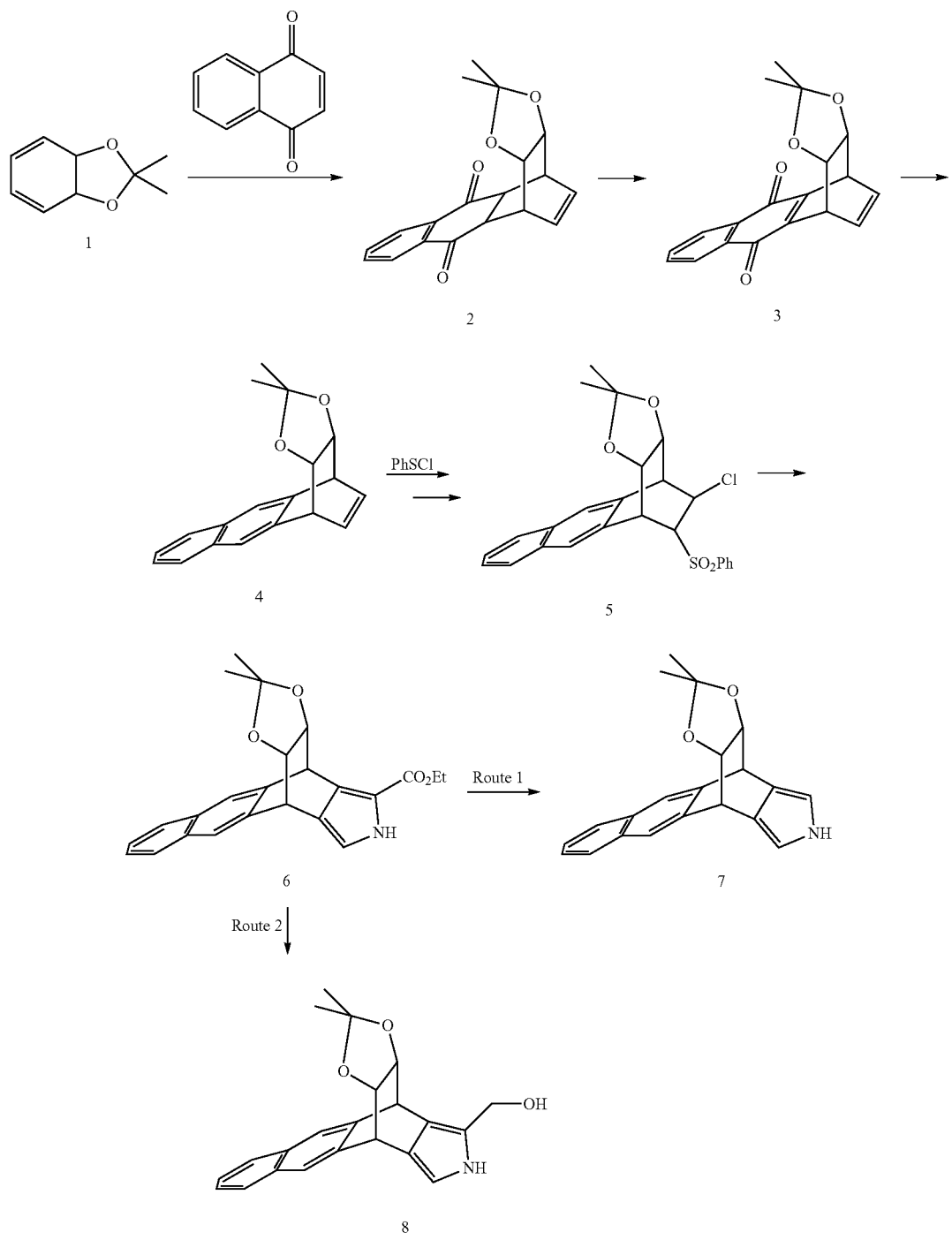

As shown in the reaction formula (11), Compound (4) is synthesized by a Diels-Alder reaction of cyclohexadiene with naphthoquinone, followed by a reaction of the resultant with a base to produce Compound (3), a reaction of the compound with hydrazine, and treatment of the resultant with a base for aromatization. Thereafter, pyrrole can be synthesized by addition of PhSCl, oxidation, and, subsequently, a Barton-Zard method. After that, a substituent at α-position can be converted as shown in Route 1 or Route 2.

In addition, an azaporphyrin compound in which all of $Z_1$ to $Z_4$ of the general formula (9) are represented by a nitrogen atom, and the B ring of the formula is represented by the general formula (27) can be synthesized by, for example, such method as shown in a reaction formula (12). The method involves: turning Dicyano Compound 1 into a tetrameric ring; and deprotecting and oxidizing the resultant to synthesize the compound.

Reaction formula (12)
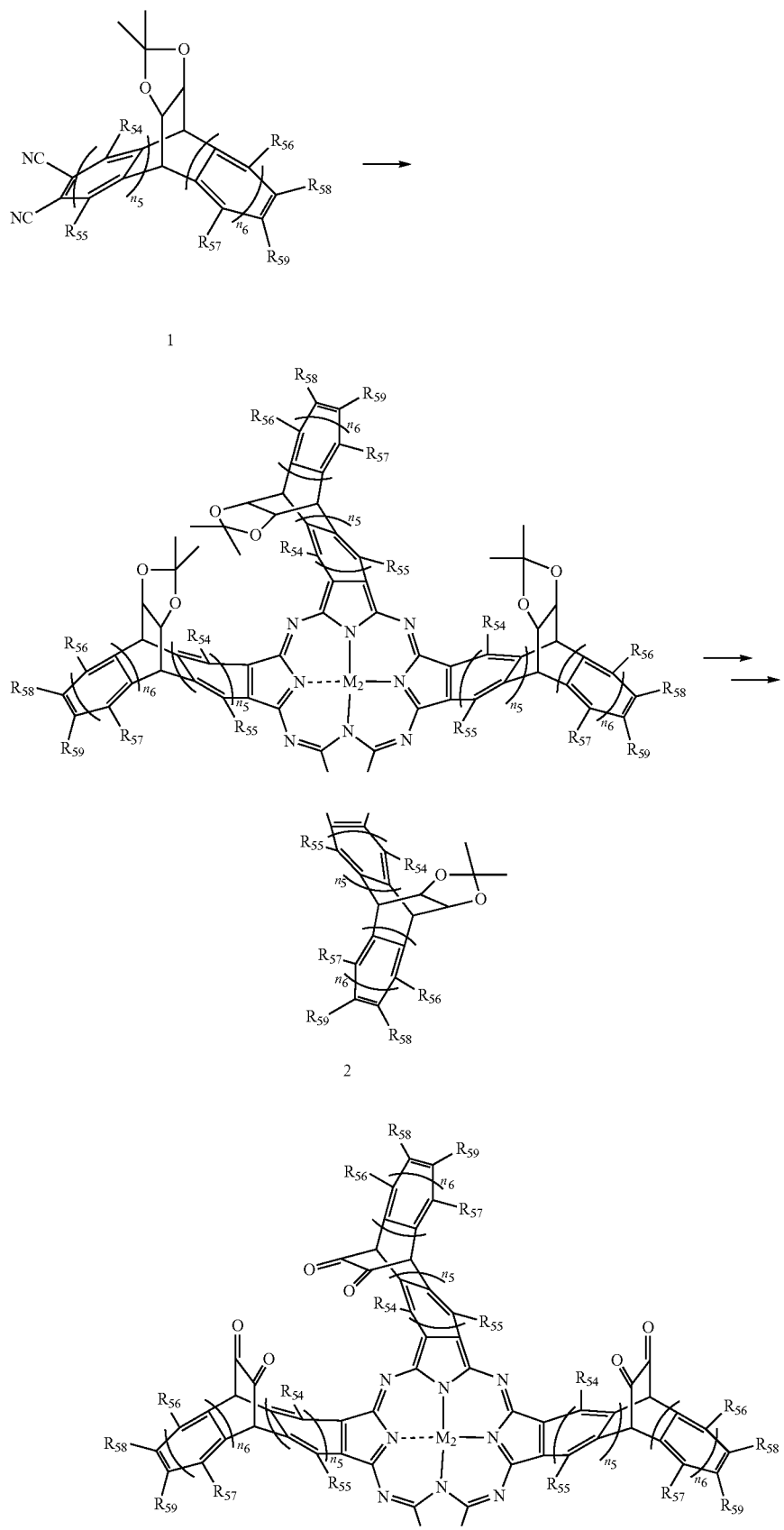

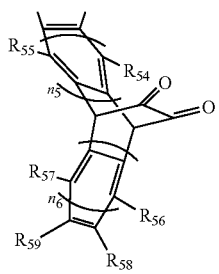

3

There is no specific limitation concerning a method of synthesizing Dicyano Compound 1 in the reaction formula (12) as a raw material for the azaporphyrin compound, but an acetonide-protected body is suitably used as a group that can be converted into the B ring, and the compound can be synthesized by, for example, such method as shown in a reaction formula (13) or (14).

Reaction formula (13)

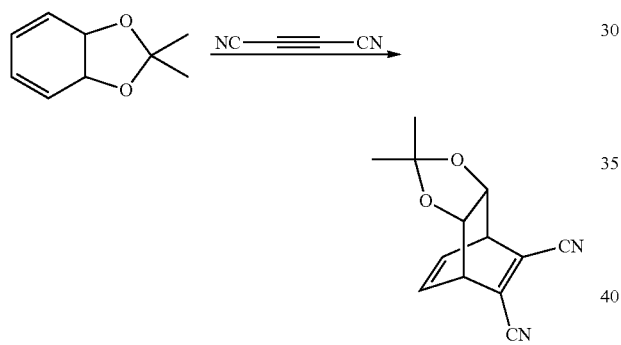

A nitrile compound can be synthesized by a Diels-Alder reaction of cyclohexadiene protected by an acetonide with dicyanoacetylene.

Reaction formula (14)

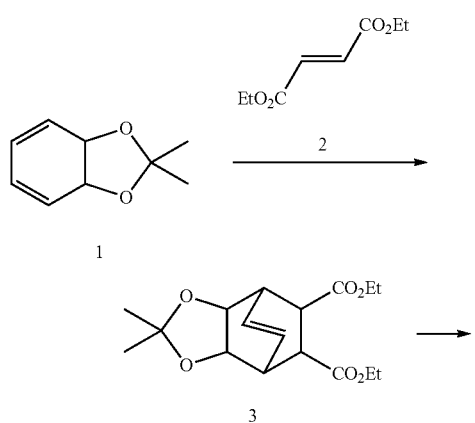

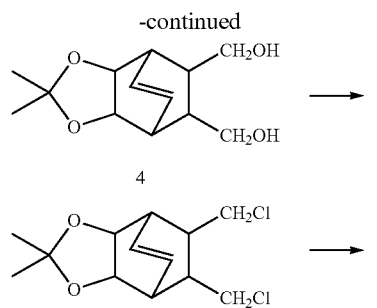

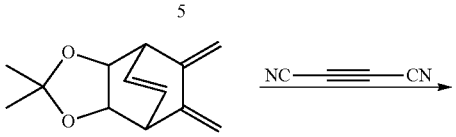

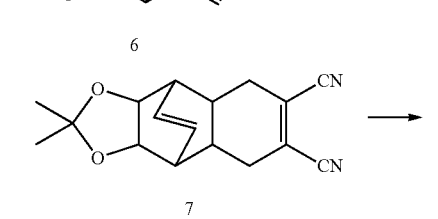

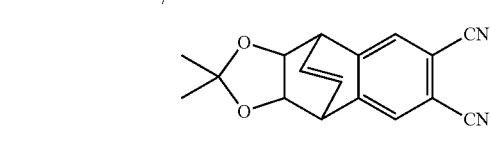

Compound 5 can be synthesized by a Diels-Alder reaction of Acetonide-protected Cyclohexadiene 1 with Ethylene Compound 2, reduction, and chlorination. After that, Dicyano Compound 8 can be synthesized by synthesis of Exomethylene 6 through dehydrochlorination, a Diels-Alder reaction of Exomethylene 6 with dicyanoacetylene, and aromatization.

The above-exemplified synthesis methods are only a few examples. Specific examples of the structure represented by the general formula (27) suitably used as the B ring are listed in Table 3. It should be noted that the substituent X in the skeletons listed in the table is selected from a hydrogen atom, a halogen atom, a cyano group, a nitro group, a linear or branched alkyl group having 1 to 12 carbon atoms, a phenyl group, and an ester group, and X's may be identical to or different from each other.

TABLE 3

| No. | B Ring |
|---|---|
| 1 | (structure) |
| 2 | (structure) |
| 3 | (structure) |
| 4 | (structure) |
| 5 | (structure) |
| 6 | (structure) |
| 7 | (structure) |
| 8 | (structure) |
| 9 | (structure) |

Of those exemplified compounds, a structure represented by a general formula (21) is particularly preferable.

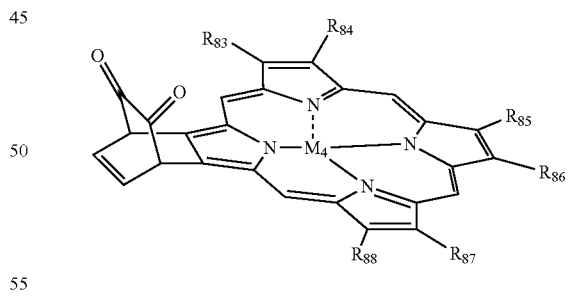

General formula (21)

where $R_{83}$ to $R_{88}$ are each independently selected from the group consisting of a hydrogen atom, a hydroxyl group, a halogen atom, an alkyl group, an alkoxy group, an alkylthio group, an ester group, an aryl group, a heterocyclic group, and an aralkyl group. Examples of the alkyl group include a methyl group, an ethyl group, a propyl group, an isopropyl group, a butyl group, an isobutyl group, an s-butyl group, and a t-butyl group; examples of the alkenyl group include a vinyl group and an allyl group; examples of the alkoxy group include a methoxy group, an ethoxy group, and a propoxy group; examples of the alkylthio group include a methylthio group and an ethylthio group; examples of the alkyl ester group include a methyl ester group, an ethyl ester group, a propyl ester group, and a butyl ester group; examples of the aryl group include a phenyl group and naphthyl group that may have a substituent; $R_{54}$ to $R_{59}$ each are selected independently from a hydrogen atom, an alkyl group, an alkoxy group, an aryl group, a heterocyclic group, an aralkyl group, a phenoxy group, a cyano group, a nitro group, an ester group, a carboxyl group, and a halogen atom; examples of the alkyl group include a methyl group, an ethyl group, a propyl group, an isopropyl group, a butyl group, an isobutyl group, an s-butyl group, and a t-butyl group; examples of the alkoxy group include a methoxy group, an ethoxy group, and a propoxy group; examples of the ester group include a methyl ester group, an ethyl ester group, a propyl ester group, and a butyl ester group; examples of the aryl group include a phenyl group and naphthyl group that may have a substituent; examples of the heterocyclic ring group include a monocyclic heterocyclic ring such as a monovalent pyridine ring, pyradine ring, pyrimidine ring, pyridazine ring, pyrrole ring, imidazole ring, pyrazole ring, furan ring, thiophene ring, oxazole ring, isoxazole ring, thiazole ring, isothiazole ring, furazan ring, selenophene group ring, and silole ring that may have a substituent, and a fused heterocyclic ring group in which a monocyclic heterocyclic ring and an aromatic hydrocarbon ring are arbitrarily combined and fused; examples of the aralkyl group include a benzyl group, a phenylethyl group, and a phenethyl group. $M_4$ represents two hydrogen atoms, a metal atom, or a metal oxide. Examples of the metal include copper, gold, silver, zinc, nickel, chromium, magnesium, and lithium. Examples of the metal oxide include TiO and VO. M4 represents particularly preferably two hydrogen atoms or a copper atom. Each pair of $R_{83}$ and $R_{84}$, $R_{85}$ and $R_{86}$, or $R_{87}$ and $R_{88}$ may be combined together to form a general formula (30).

General formula (30)

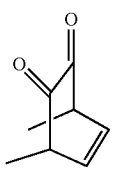

Preferable examples of the above-mentioned organic semiconductor precursor to be used in the present invention are shown below.

Unsubstituted structures are primarily shown in the examples, but the precursor may have a substituent, or a metal may coordinate at the center of the precursor. Compounds shown here are merely examples, and the compound of the present invention is by no means limited thereto.

Therefore, for example, the following general formula (32) can be rewritten into a general formula (22).

General formula (32)

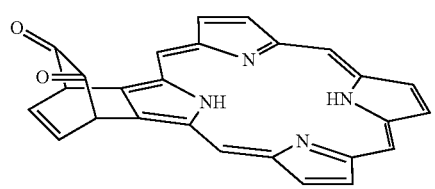

General formula (22)

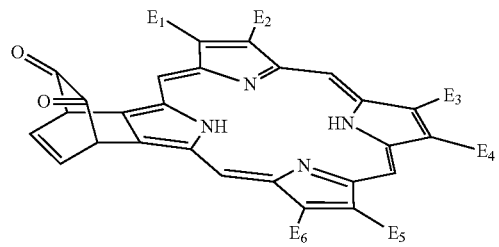

Hereinafter, specific examples of the organic semiconductor precursor are shown.

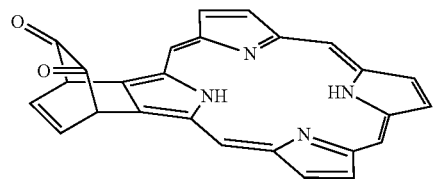

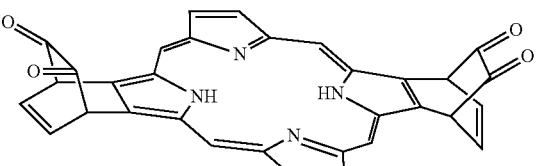

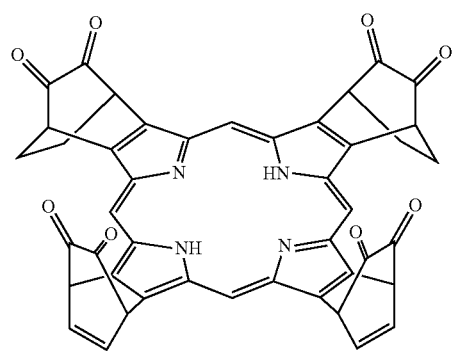

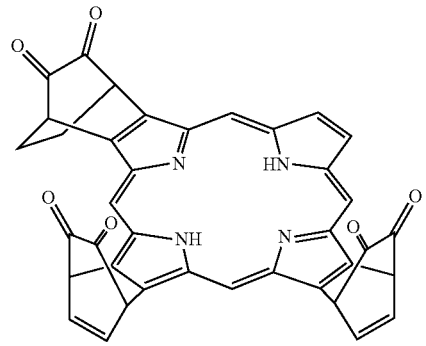

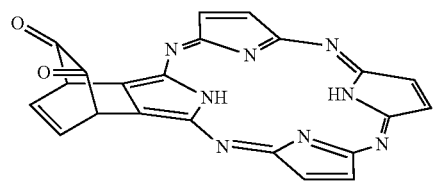

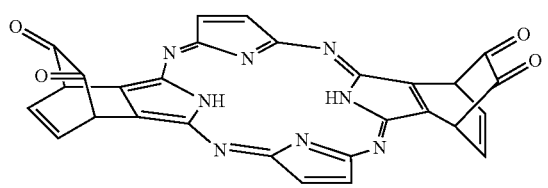
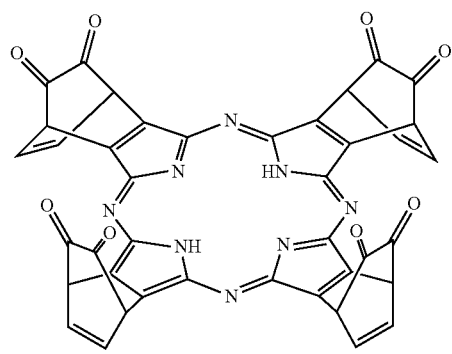
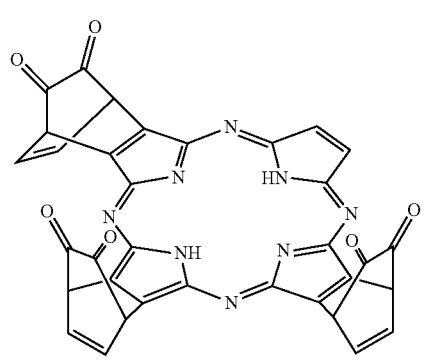
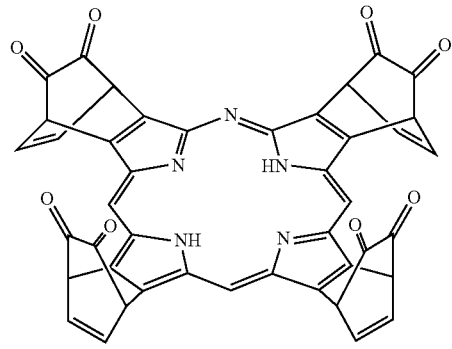
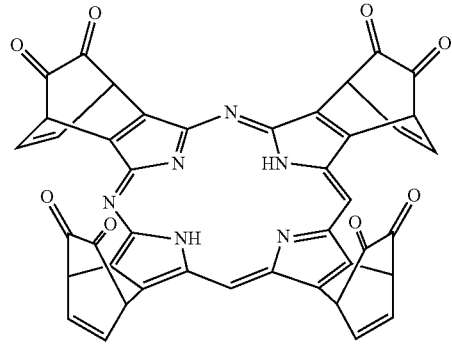
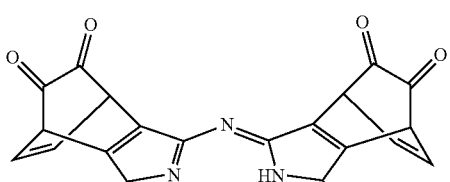
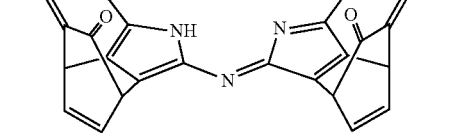
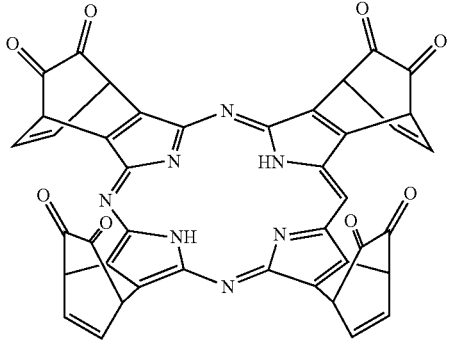
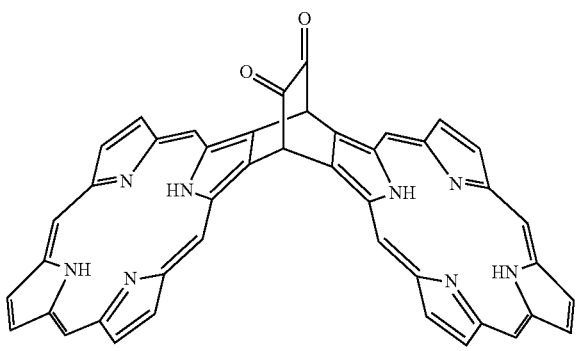
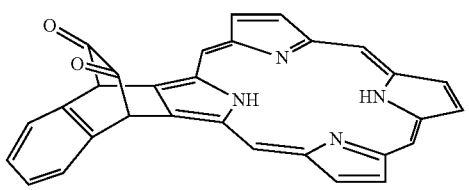
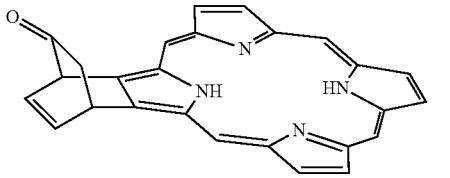
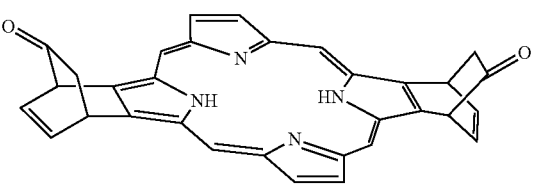

45
-continued
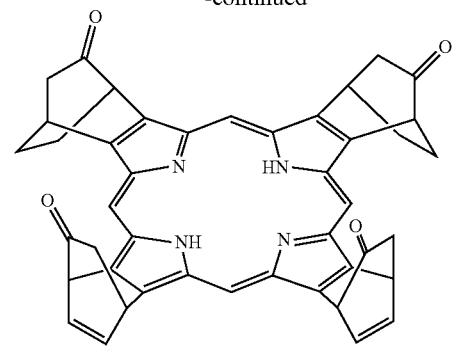
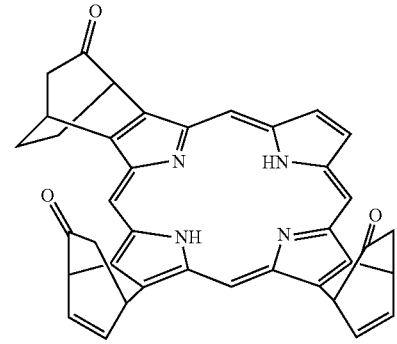
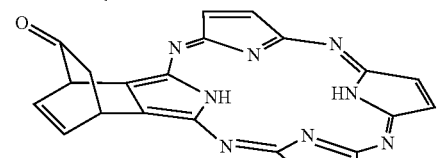
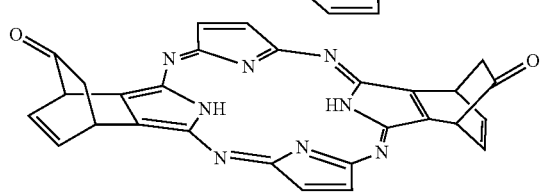
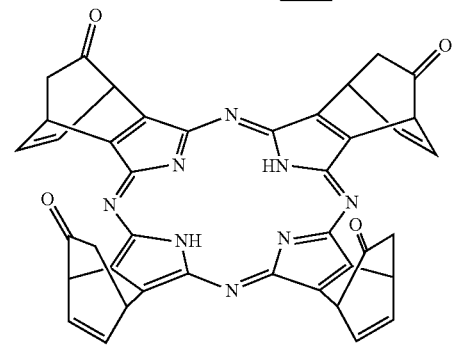
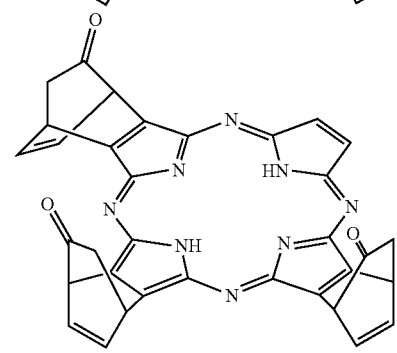
46
-continued
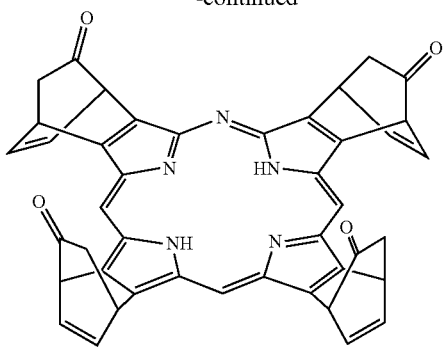
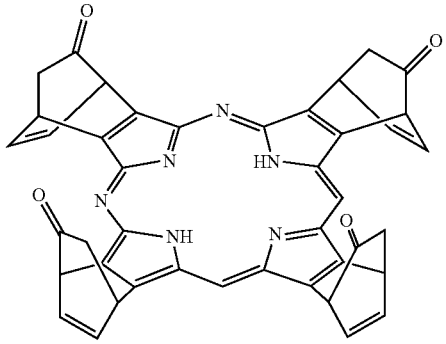
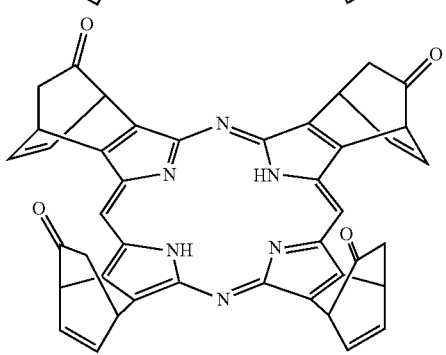
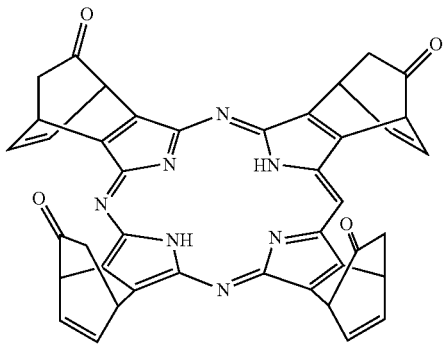
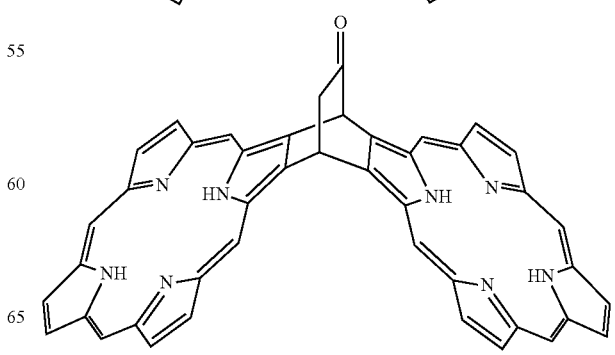

47
-continued
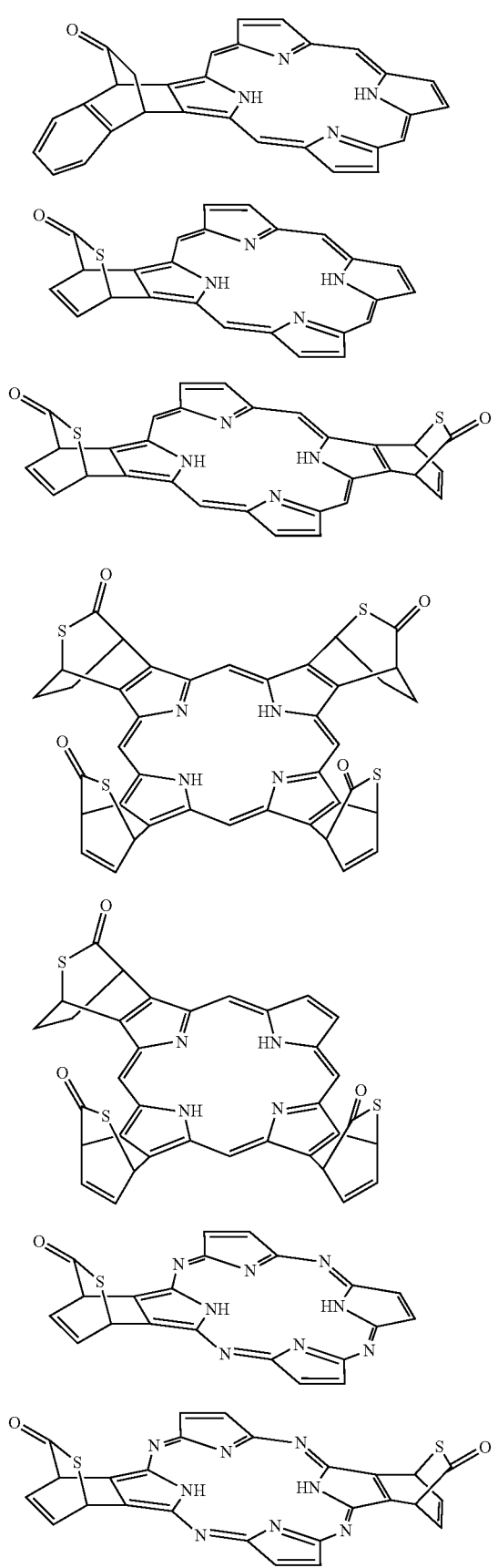
48
-continued
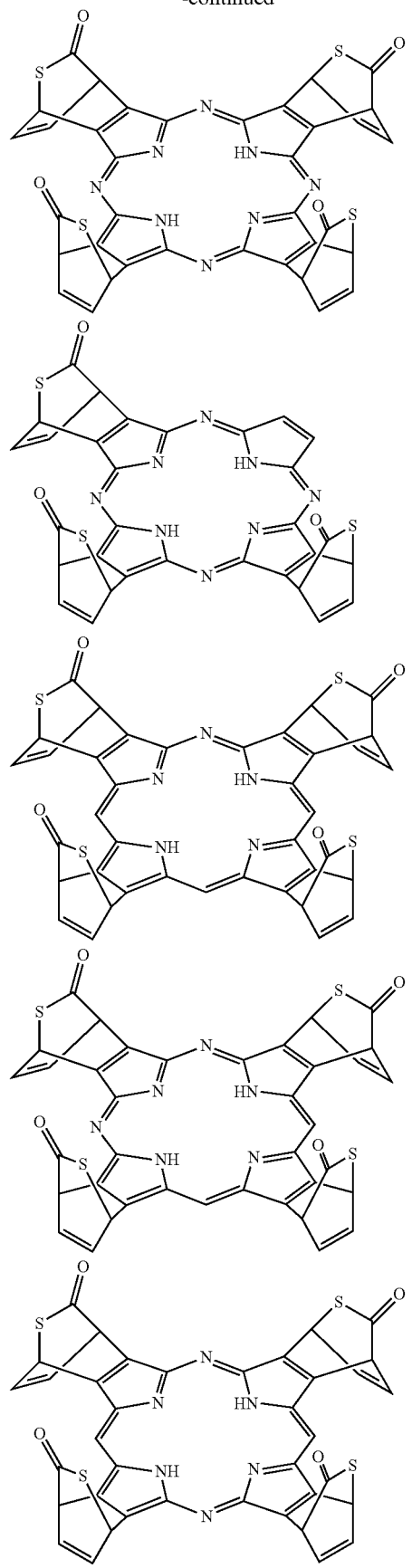

-continued

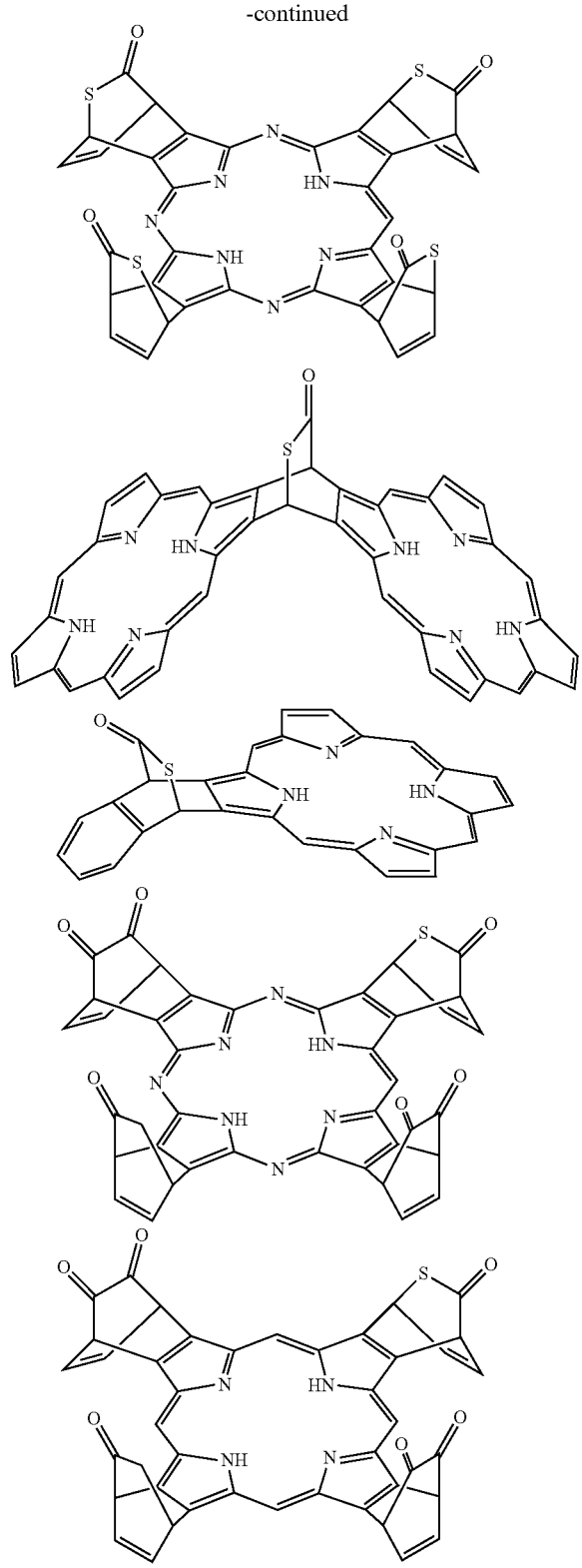

It should be noted that such a compound as the present invention is effective for solubilization of benzoporphyrin or phthalocyanine, and, furthermore, only the portion of the compound irradiated with light can be transformed into a photosensitizing dye, so the compound is sufficiently expected to have, for example, an effect of reducing damage to normal cells. Therefore, in addition to the fact that the compound can be used in a method of producing an organic semiconductor device, the compound may be developed into a photosensitizing dye for PDT. In addition, such a pigment as phthalocyanine or porphyrin can be produced by irradiation with light, so the compound has potential for application in the field of printing where light is utilized and for forming a p-n junction at the molecular level by irradiation with light, and may be applied to, for example, an organic thin-film solar cell having high sensitivity and a large area. The application of such organic semiconductor precursor onto a base body results in the formation of a layer composed of the organic semiconductor precursor. A method of forming the layer composed of the organic semiconductor precursor is preferably a method in which the organic semiconductor precursor is dissolved in an organic solvent and applied onto the base body to form the layer. An organic solvent to be used for dissolving the organic semiconductor precursor is not particularly limited as long as an organic semiconductor material neither reacts with the solvent nor precipitates. In addition, two or more types of organic solvents may be used as a mixture. In this case, taking into account the surface smoothness and thickness uniformity of a coating film, it is desirable to select the solvent.

Examples of the solvent include acetone, methylethyl ketone, methylisobutyl ketone, cyclohexanone, hexane, heptane, cyclohexane, tetrahydrofuran, dioxane, diethyl ether, isopropyl ether, dibutyl ether, toluene, xylene, 1,2-dimethoxyethane, chloroform, methylene chloride, dichloroethane, 1,2-dichloroethylene, dimethylsulfoxide, N-methyl pyrrolidone, chlorobenzene, dichlorobenzene, and trichlorobenzene. Each of them may be used alone as a solvent, or a mixture of two or more of them may be used as a solvent. The concentration of a solution comprised of the organic semiconductor precursor and the solvent, which is arbitrarily adjusted depending on a desired thickness, is preferably 0.01 wt % or more and 5 wt % or less.

A method of applying the solution comprised of the organic semiconductor precursor and the solvent onto the base body is not particularly limited. Examples of the application method include the conventional coating methods such as a spin coating method, a cast method, a spray coating method, a doctor blade method, a die coating method, a dipping method, a printing method, an inkjet method, and a dropping method. In addition, examples of the printing method include screen printing, offset printing, gravure printing, flexographic printing, and microcontact printing. Of those application methods, the spin coating method, the dipping method, the spray coating method, and the inkjet method are preferable because the application amount can be controlled so that a film having a desired thickness is formed. Further, to prevent the intrusion of dust and the like in a coating film as much as possible, it is desirable to filter the solution in advance by means of a membrane filter. This is because the intrusion of insoluble matter or dust from the outside may obstruct uniform orientation, thereby increasing an OFF current and reduction an ON/OFF ratio. In addition, the coating film of the organic semiconductor precursor can be subjected to preliminary drying.

An organic semiconductor film obtained through the foregoing operations has a thickness of preferably 10 nm or more and 500 nm or less, or more preferably 20 nm or more and 200 nm or less. The thickness can be measured with, for example, a surface roughness meter or a level difference meter.

Next, in step (ii), the formed layer composed of the organic semiconductor precursor is irradiated with light.

The irradiation of the layer composed of the organic semiconductor precursor with light bring about such reverse Diels-Alder reaction as shown in the reaction formulae (1) to (3), whereby a layer composed of an organic semiconductor is formed. The wavelength of light with which the layer composed of the organic semiconductor precursor is irradiated, is only required to fall within an absorption wavelength region of the organic semiconductor precursor, but preferably falls within a wavelength region of 190 nm or more and 500 nm or less. This is because a wavelength shorter than 190 nm may cause damage to the peripheral part of the layer or a side reaction, and a wavelength in excess of 500 nm may cause damage to the resultant organic semiconductor. A light source is selected from, for example, a tungsten lamp, a halogen lamp, a metal halide lamp, a sodium lamp, a xenon lamp, a high-pressure mercury lamp, a low-pressure mercury lamp, and various laser light beams. A method of irradiating the layer with light is not particularly limited as long as the organic semiconductor precursor is converted into the organic semiconductor, but a method of directly irradiating the organic semiconductor precursor with light is desirable in order that a photoreaction may be more effectively performed. It should be noted that, when heat generated by irradiation with light is applied to the organic semiconductor precursor, the heat is preferably cut off with a heat absorbing filter or the like. In addition, the organic semiconductor can be patterned by irradiating the layer with light through a mask. It is more preferable that light and heat be simultaneously applied to the layer composed of the organic semiconductor precursor in order that an excellent crystallized film of the organic semiconductor may be obtained. This is because, when light energy and heat energy are simultaneously applied to the layer, the organic semiconductor precursor is converted into the organic semiconductor with light, and gaps in crystal grains produced by an elimination reaction are filled with heat energy. As a result, the layer composed of the organic semiconductor can be led to such a more stable crystalline state that oxygen or moisture hardly infiltrates into the layer.

In that case, heat is applied by externally heating the base body. Any method may be employed as a heating method, but a method is preferable in which the base body is heated on a hot plate, or in an oven with internal air circulation or a vacuum oven. Of those, the method in which the base body is heated on a hot plate is more preferable. The optimum temperature at which the base body is heated varies depending on the type of organic semiconductor precursor, but the base body is preferably heated in the temperature region of 50° C. or higher and 180° C. or lower in consideration of, for example, an influence on the peripheral part of the layer.

When light and heat are simultaneously applied to the layer, the time period for which light and heat are simultaneously applied to the layer varies depending on, for example, the thickness and material of the layer to a large extent, so the time period cannot be uniquely determined. In general, however, it becomes difficult for light to permeate into a deep portion of the crystallized film of the organic semiconductor as the film grows, so the time period for which light energy and heat energy are simultaneously applied to the layer is preferably 1 second or longer and 30 minutes or shorter. In such a manner, light can be effectively utilized in converting the organic semiconductor precursor into the organic semiconductor. The time period for which light energy and heat energy are simultaneously applied to the layer is more preferably 1 minute or longer and 15 minutes or shorter. In addition, in order that a more stable crystallized film can be obtained, only heat energy may be further applied after simultaneously applying light energy and heat energy.

The layer composed of the organic semiconductor obtained through those operations has a thickness of preferably 10 nm or more and 500 nm or less, or more preferably 20 nm or more and 200 nm or less. The thickness can be measured with, for example, a surface roughness meter or a level difference meter.

In the present invention, the base body is an object on which the layer composed of the organic semiconductor precursor is to be formed.

The base body may be comprised of a single layer, or multiple layers.

When the base body is comprised of multiple layers, the outermost layer is preferably a crystallization promoting layer. When the outermost layer is a crystallization promoting layer, a ground on which the crystallization promoting layer is to be formed (in the case of a field effect transistor, the ground is generally a structure comprised of a support layer, a gate electrode, and a gate insulating layer; provided that the gate insulating layer can be omitted in some cases, the structure may be comprised only of the support layer depending on the order in which the layers are superimposed, and other layers may be formed) is referred to as a base material.

According to detailed investigation conducted by the inventors of the present invention, the simultaneous application of light energy and heat energy to the layer composed of the organic semiconductor precursor on the crystallization promoting layer to transform the layer formed of the organic semiconductor precursor into the layer formed of the organic semiconductor may be important for bringing out the crystallization promoting function to the maximum. In general, when the organic semiconductor precursor is subjected to an elimination reaction by applying light energy and heat energy to the precursor to produce the organic semiconductor, the production of a gap between crystal grains composed of the resultant compound is observed. On the other hand, when such reaction is performed on the crystallization promoting layer, the gap between the crystal grains of the layer composed of the organic semiconductor is filled, whereby uniform crystals are formed over the entire substrate.

This is probably because the crystallization promoting layer has a function of stabilizing the crystal grains of the layer composed of the organic semiconductor (the stabilization may involve the movement or rotation of the grains) and promoting the junction between the crystal grains. Therefore, the crystallization promoting layer is a layer for stabilizing crystal grains (the stabilization may involve the movement or rotation of the grains) and/or promoting junction between the crystal grains.

The inventors of the present invention consider that the crystallization promoting layer functions by virtue of an improvement in crystallinity of the layer composed of the organic semiconductor by such action of the crystallization promoting layer. The occurrence of the junction between the crystal grains is considered to be particularly preferable.

Such crystallization promoting layer is preferably a layer containing a polysiloxane compound.

Within the scope of investigation conducted by the inventors of the present invention, the polysiloxane compound may have an action of promoting the crystallization of the organic semiconductor.

Further, the inventors of the present invention have found that a method involving simultaneously applying light energy and heat energy to the layer formed of the organic semiconductor precursor after the application (lamination) of the layer composed of the organic semiconductor precursor onto the surface of the layer containing the polysiloxane compound is effective for the formation of a layer composed of the organic semiconductor with high quality. Hereinafter, the layer containing the polysiloxane compound may also be referred to simply as "polysiloxane compound layer".

According to such a method, organic semiconductor crystals can be formed which, at the interface between the layer containing the polysiloxane compound and the layer formed of the organic semiconductor, is continuously uniform and less in defect, and hardly deteriorates owing to external stimuli such as oxygen or water. Accordingly, it is considered that organic semiconductor devices can be produced in which the variation in characteristics between the devices are small and high in durability. While such a method may be useful for any organic semiconductor device, it is considered to be particularly useful for the production of an organic field effect transistor which is an example of the organic semiconductor devices.

In the present invention, the term "polysiloxane compound" refers to a polymer having a siloxane structure (—Si—O—) and an organic silane structure, and the term "layer composed of the polysiloxane compound" refers to a layer composed of a polymer having a siloxane structure (—Si—O—) and an organic silane structure. Therefore, the polysiloxane compound may be a copolymer with any other organic or inorganic polymer as long as the compound has the above structures. In the case of a copolymer with any other polymer, the siloxane structure or the organic silane structure may be present in its main chain or in its side chain due to graft polymerization or the like. It should be noted that the organic silane structure is a structure obtained by directly bonding Si and C.

Possible examples of the polysiloxane compound include compounds having various structures such as a linear structure and a cyclic structure.

The polysiloxane compound more preferably has a highly crosslinked or branched structure. The term "highly crosslinked or branched structure" as used herein comprehends network, ladder-like, cage-like, star-like, and dendritic structures. In addition, the crosslinked or branched structure does not necessarily need to be formed through the siloxane structure. The structure may contain a structure obtained by crosslinking organic groups such as a vinyl group, an acryloyl group, an epoxy group, and a cinnamoyl group, or a structure branched through an organic group which is trifunctional or more.

Examples of the polysiloxane compound include compounds each having a structure represented by the following general formula (6). The main chain of such structure is a siloxane unit, and the side chains ($R_5$ to $R_8$) of the structure are each a substituent having an organic group such as a hydrogen atom or a carbon atom.

General formula (6)

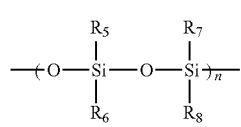

In the formula, $R_5$ to $R_8$ each represent a substituted or unsubstituted alkyl or alkenyl group having 1 to 8 carbon atoms, a substituted or unsubstituted phenyl group, or a siloxane unit, and $R_5$ to $R_8$ may be identical to or different from one another.

Examples of the substituted alkyl group include an alkyl group in which a hydrogen atom is substituted by a halogen atom, a hydroxyl group, a cyano group, a phenyl group, a nitro group, a mercapto group, or a glycidyl group. In addition, a methyl group and a methylene group may be substituted by an amino group. Further, examples of the substituted phenyl group include a phenyl group in which a hydrogen atom is replaced by a halogen atom, a hydroxyl group, a cyano group, a nitro group, a mercapto group, or a glycidyl group. Of course, the substituent is not limited to them. It should be noted that those examples hold true for all of R's and $R_n$'s (n represents a natural number) in siloxane compounds described below except for a logically improbable exception.

The substituents $R_5$ to $R_8$ may each independently be one of such siloxane units as shown below:

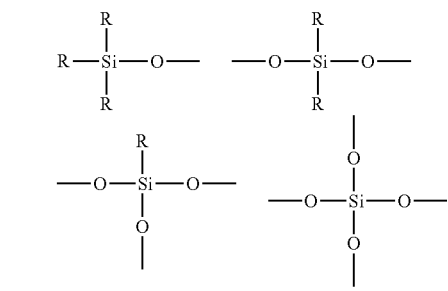

where R's are each independently a substituted or unsubstituted alkyl group having 1 to 8 carbon atoms, a substituted or unsubstituted phenyl group, or any one of the siloxane units shown above, and the respective R's may be the same functional group, or may be functional groups different from each other.

The shape of polysiloxane may include, for example, linear, cyclic, network, ladder-like, or cage-like structures depending on the types of substituents in the general formula (6), and polysiloxane to be used in the present invention may take any one of these structures.

Other examples of the polysiloxane compound to be used in the present invention include compounds each having such a structure as represented by the following general formula (8).

General formula (8)

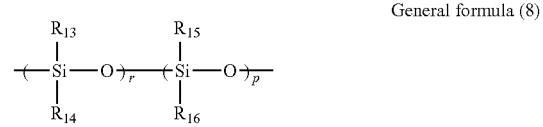

In the formula, $R_{13}$ to $R_{16}$ each represent a substituted or unsubstituted alkyl or alkenyl group having 1 to 8 carbon atoms, or a substituted or unsubstituted phenyl group, $R_{13}$ to $R_{16}$ may be identical to or different from one another, r and p each independently represent an integer of 0 or more, and the sum of r and p represents an integer of 1 or more.

The polysiloxane compound to be used in the present invention particularly preferably has at least such a specific silsesquioxane skeleton as represented by the following general formula (7).

General formula (9)

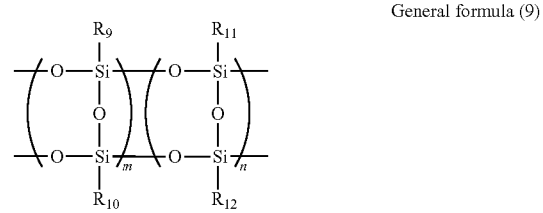

In the formula, $R_9$ to $R_{12}$ each represent a substituted or unsubstituted alkyl or alkenyl group having 1 to 8 carbon atoms, or a substituted or unsubstituted phenyl group, $R_9$ to $R_{12}$ may be identical to or different from one another, m and n each independently represent an integer of 0 or more, and the sum of m and n represents an integer of 1 or more. The compound may be a random copolymer or a block copolymer. Extremely specific examples of $R_9$ to $R_{12}$ include: an unsubstituted alkyl group such as a methyl group or an ethyl group; an unsubstituted phenyl group; and a substituted phenyl group such as a dimethylphenyl group or a naphthyl group. In addition, the substituents $R_9$ to $R_{12}$ may contain various atoms such as an oxygen atom, a nitrogen atom, and a metal atom as well as a carbon atom and a hydrogen atom.

The silsesquioxane skeleton in the present invention will be described. The general formula (7) shows a structure in which m repeating silsesquioxane units each having the substituents $R_9$ and $R_{10}$ (hereinafter referred to as "first units") and n repeating silsesquioxane units each having the substituents $R_{11}$ and $R_{12}$ (hereinafter referred to as "second units") are connected to each other. m and n each independently represent an integer of 0 or more, and m+n is an integer of 1 or more. However, the foregoing does not mean that the repetition of the first units and the repetition of the second units are separated from each other. Both the units may be connected to each other in a separate manner or in a randomly intermingled manner.

In addition, a siloxane compound having both a structure represented by the general formula (7) and a structure represented by the general formula (8) can also be used as a polysiloxane compound in the present invention.

As for a method of forming the crystallization promoting layer in the present invention composed mainly of a compound having such specific silsesquioxane skeleton as represented by the general formula (7) on the base material, the following method is exemplified. That is, a solution containing polyorganosilsesquioxane compounds represented by at least one of the following general formulae (10) and (11) is applied onto the base material and is heated and dried, whereby the base body can be obtained.

In this case, heating is carried out at a temperature of preferably 140° C. or higher and 300° C. or lower, or more preferably 150° C. or higher and 230° C. or lower. When heating is carried out at lower than 140° C., the hydrolysis reaction of the solution may be insufficient.

General formula (10)

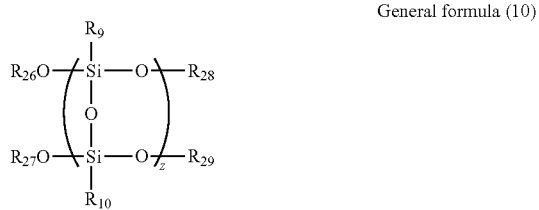

In the formula, $R_9$ and $R_{10}$ each represent a substituted or unsubstituted alkyl or alkenyl group having 1 to 8 carbon atoms, or a substituted or unsubstituted phenyl group, $R_9$ and $R_{10}$ may be the same functional group, $R_{26}$ to $R_{29}$ each independently represent an alkyl group having 1 to 4 carbon atoms, or a hydrogen atom, and z represents an integer of 1 or more.

General formula (11)

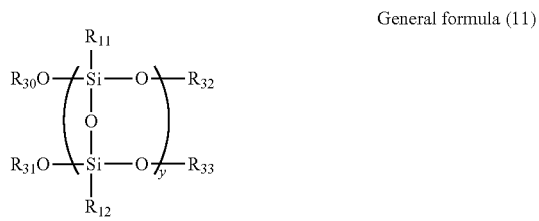

In the formula, $R_{11}$ and $R_{12}$ each represent a substituted or unsubstituted alkyl or alkenyl group having 1 to 8 carbon atoms, or a substituted or unsubstituted phenyl group, $R_{11}$ and $R_{12}$ may be the same functional group, $R_{30}$ to $R_{33}$ each independently represent an alkyl group having 1 to 4 carbon atoms, or a hydrogen atom, and y represents an integer of 1 or more.

A hydrolysis reaction is induced at the terminal of each compound by such heating and drying, whereby the silsesquioxane compounds as raw materials are connected to each other in ladder form so as to be densified, provided that the temperature at which the raw material compounds are heated and dried is not so high that organic matter completely disappears, so the raw material compounds can be turned into not a complete silica structure but a silsesquioxane skeleton in which most of substituents remain.

In addition, at the time of the drying step, a small amount of an acid such as formic acid may be added to the solution to be applied for the purpose of aiding a reaction in which the silsesquioxane compounds as oligomers mutually crosslink.

The addition amount of the acid is not particularly limited. When formic acid is used as the acid, the acid is preferably added in an amount in the range of 1 wt % to 30 wt % with respect to the solid content weight of the polyorganosilsesquioxane compounds in the solution to be applied because crosslinking reaction is promoted. When the addition amount is smaller than 1 wt %, the effect of promoting crosslinking reaction may be insufficient. In contrast, when the addition amount is larger than 30 wt %, the properties of the film having been dried may be impaired.

In the process of the crosslinking reaction and the removal of the solvent of the solution, a stabilizer that does not evaporate, volatilize, or burn off in the system is removed from the solution system as much as possible.

Any one of arbitrary solvents including alcohols and esters can be used as the solvent of the solution to be applied. The solvents are selected in consideration of, for example, wettability for a substrate.

A method of applying a raw material solution for the crystallization promoting layer onto the base material is not particularly limited. As the application method, the conventional coating methods can be employed, such as a spin coating method, a cast method, a spray coating method, a doctor blade method, a die coating method, a dipping method, a printing method, an inkjet method, and a dropping method. Examples of the printing method include screen printing, offset printing, gravure printing, flexographic printing, and microcontact printing. Of those application methods, the spin coating method, the dipping method, the spray coating method, and the inkjet method are preferable because the application amount can be controlled so that a film having a desired thickness is formed. In addition, it is important that dust and the like are mixed into an application solution to the extent possible to retain the insulation properties of the obtained film, so it is desirable that a raw material solution be filtrated with a membrane filter in advance.

The concentration of the solution is preferably adjusted so that the crystallization promoting layer has a thickness of 10 nm or more. The concentration is more preferably adjusted so that the layer has a thickness of 15 nm or more and 500 nm or less. This is because, when the thickness is less than 10 nm, it may become difficult to obtain a uniform film.

Prior to the application of the raw material solution for the crystallization promoting layer, the surface of the base material may be modified by, for example, ultrasonic treatment with an alkali liquid or irradiation with UV for the purpose of improving wettability of the surface of the base material.

The organic semiconductor precursor is applied onto the base body on which the crystallization promoting layer has been formed. Thus, the layer composed of the organic semiconductor precursor is formed. In this case, it is desirable that the crystallization promoting layer and the layer composed of the organic semiconductor precursor are superimposed in close contact with each other. The term "close contact" refers to a state that at least part of the crystallization promoting layer and at least part of the layer composed of the organic semiconductor precursor are in contact with each other without the intervention of any other layer.

As described above, the layer composed of the organic semiconductor precursor is formed on the crystallization promoting layer. After that, the simultaneous application of light and heat results in the conversion of a bicyclo skeleton into an aromatic ring (conversion of the precursor into the organic semiconductor). Crystal growth due to the stacking of organic semiconductor molecules occurs simultaneously with the conversion into the aromatic ring, whereby the crystallized film of the organic semiconductor is formed. Thus, the layer composed of the organic semiconductor is formed.

FIG. 1 shows the schematic sectional view of an organic field effect transistor where the organic field effect transistor is obtained through the above steps. The field effect transistor shown in FIG. 1 is made up of a gate electrode 1, an insulating layer 2, an A layer (crystallization promoting layer) 3, a source electrode 4, a drain electrode 5, and a B layer (layer composed of an organic semiconductor) 6.

Description is given here on the assumption that a base material is comprised of the gate electrode 1 and the insulating layer 2, and a base body is comprised of the gate electrode 1, the insulating layer 2, and the A layer (crystallization promoting layer) 3.

The gate electrode 1, the source electrode 4, and the drain electrode 5 are not particularly limited as long as they are made of conductive materials. Examples of the materials include: platinum, gold, silver, nickel, chromium, copper, iron, tin, antimonial lead, tantalum, indium, aluminum, zinc, magnesium, and alloys of those metals; conductive metal oxides such as an indium-tin oxide; and inorganic and organic semiconductors with increased conductivity through doping and the like, such as a silicon single crystal, polysilicon, amorphous silicon, germanium, graphite, polyacetylene, polyparaphenylene, polythiophene, polypyrrole, polyaniline, polythienylenevinylene, and polyparaphenylenevinylene. Examples of a method of producing an electrode include a sputtering method, an evaporation method, a printing method from a solution or a paste, an inkjet method, and a dipping method. In addition, an electrode material is preferably any of the above materials that have low electrical resistance at a contact surface with the organic semiconductor layer.

The insulating layer 2 is not limited as long as the A layer 3 can be uniformly applied to the layer, but the insulating layer is preferably one having a high dielectric constant and low conductivity. Examples of a material for the insulating layer include: inorganic oxides and nitrides such as silicon oxide, silicon nitride, aluminum oxide, titanium oxide, and tantalum oxide; and polyacrylate, polymethacrylate, polyethylene terephthalate, polyimide, and polyether. Of the above insulating materials, an insulating material having high surface smoothness is preferable. In addition, the A layer itself is excellent in insulating property, and hence, the A layer itself may be used as a gate insulating layer by adjusting the thickness of the A layer to such a thickness that the layer exerts the insulating property.

A field effect transistor structure in the present invention may be any one of a top contact electrode type, a bottom contact electrode type, and a top gate electrode type. In addition, the structure is not limited to a horizontal type structure, and may be a vertical type structure (structure in which one of a source electrode and a drain electrode is present on the surface of an organic semiconductor layer on the side of a base material and the other is present on the surface of the organic semiconductor layer on the side opposite to the base material).

The third embodiment of the present invention is a method of producing an organic semiconductor device having a layer composed of an organic semiconductor, including: (I) forming a layer composed of an organic semiconductor precursor on a base body; and (II) subjecting the organic semiconductor precursor heating and irradiating with light; and (III) the layer composed of the organic semiconductor precursor contains, as the organic semiconductor precursor, a compound having in its molecule at least one of a structure represented by the following general formula (5).

General formula (5)

The organic semiconductor precursor to be used in the present invention contains an acene compound containing in its molecule at least one SCO skeleton represented by the general formula (5) as a partial structure. Such acene compound has preferably a structure represented by a general formula (13), or more preferably a pentacene precursor.

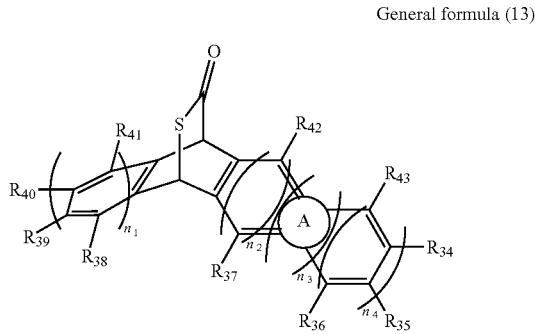

General formula (13)

In the formula, A is a cyclic structure, and represents an SCO skeleton represented by the general formula (12), or a five- or six-membered heterocyclic ring. Examples of the five- or six-membered heterocyclic ring include a pyridine ring, a pyrazine ring, a pyrimidine ring, a pyridazine ring, a pyrrole ring, an imidazole ring, a pyrazole ring, a furan ring, a thiophene ring, an oxazole ring, an isoxazole ring, a thiazole ring, an isothiazole ring, a furazan ring, a selenophene ring, and a silole ring. $R_{37}$ and $R_{42}$ each independently represent a hydrogen atom, an alkyl group, an alkoxyl group, an ester group, or a phenyl group. $R_{34}$ to $R_{36}$, $R_{38}$ to $R_{41}$, and $R_{43}$ each independently represent a hydrogen atom, an alkyl group, an alkoxyl group, an aryl group, a heterocyclic group, an aralkyl group, a phenoxy group, a cyano group, a nitro group, an ester group, a carboxyl group, or a halogen atom. The term "aryl group" as used herein refers to a monovalent, monocyclic or polycyclic aromatic hydrocarbon group, and examples of the polycyclic aromatic hydrocarbon include hydrocarbons each obtained by condensing two to fifteen aromatic hydrocarbon rings, such as naphthalene, anthracene, azulene, heptalene, biphenylene, indacene, acenaphthylene, phenanthrene, triphenylene, pyrene, chrysene, picene, perylene, pentaphene, rubicene, coronene, pyranthrene, and ovalene. Positions at which the two to fifteen rings are condensed are not limited to those of the examples, and the rings may be condensed at any positions. In addition, examples of the heterocyclic ring include monocyclic heterocyclic rings such as monovalent pyridine, pyrazine, pyrimidine, pyridazine, pyrrole, imidazole, pyrazole, furan, thiophene, oxazole, isoxazole, thiazole, isothiazole, furazan, selenophene, and silole rings, and condensed heterocyclic groups each obtained by condensing an arbitrary combination of a monocyclic heterocyclic ring and an aromatic hydrocarbon ring. The aryl group or the heterocyclic group may have a substituent(s), and may be substituted by the substituent(s) at any position(s) as long as the group can be substituted by the substituent(s) at the position(s). Further, aryl groups, heterocyclic groups, or an aryl group and a heterocyclic group may be combined with each other to form an oligomer. $R_{34}$ to $R_{36}$, $R_{38}$ to $R_{41}$, and $R_{43}$ may be identical to or different from one another. Each pair of $R_{34}$ and $R_{38}$, and $R_{39}$ and $R_{40}$ may be combined together to form an SCO skeleton, or a five- or six-membered heterocyclic ring. Here, examples of the five- or six-membered heterocyclic ring include a pyridine ring, a pyrazine ring, a pyrimidine ring, a pyridazine ring, a pyrrole ring, an imidazole ring, a pyrazole ring, a furan ring, a thiophene ring, an oxazole ring, an isoxazole ring, a thiazole ring, an isothiazole ring, a furazan ring, a selenophene ring, and a silole ring. The sum of $n_1$ to $n_4$ represents an integer of 1 or more. Of those, a structure to be converted into an acene-type compound with light, a structure to be converted into an oligomer obtained by coupling two to six identical or different acene-type compounds as described above with light, or a structure to be converted into a structure obtained by coupling the acene-type compound with a heterocyclic ring with light is more preferable. The term "acene-type compound" refers to a compound obtained by linearly condensing three or more rings selected from aromatic hydrocarbon rings and heterocyclic rings, such as anthracene, tetracene, pentacene, acridine, and thianthrene.

Examples of a preferable compound as the organic semiconductor precursor to be used in the present invention are shown below. It should be noted that only a few examples are shown herein, and the compound of the present invention is not limited to them.

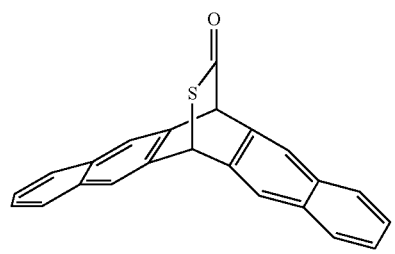 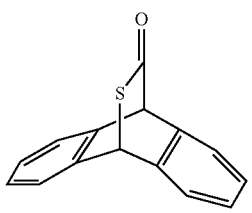

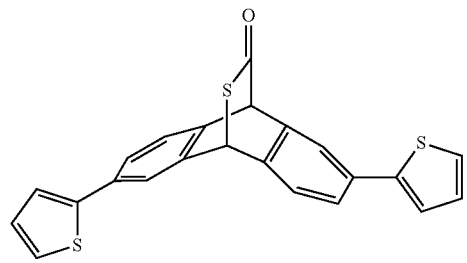 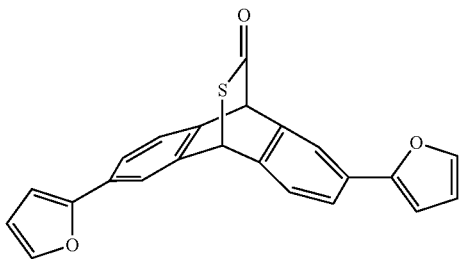

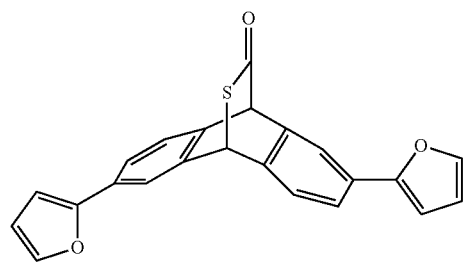 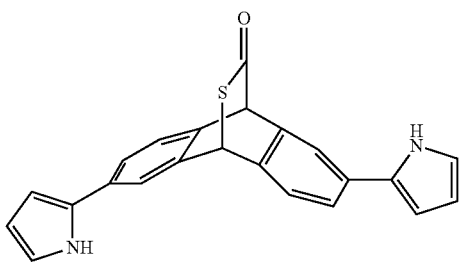

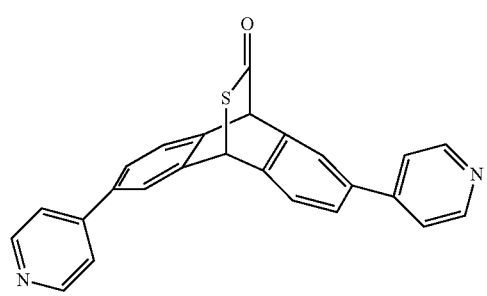 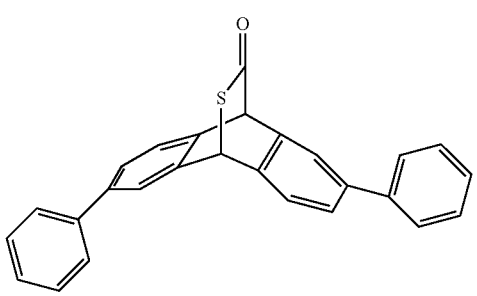

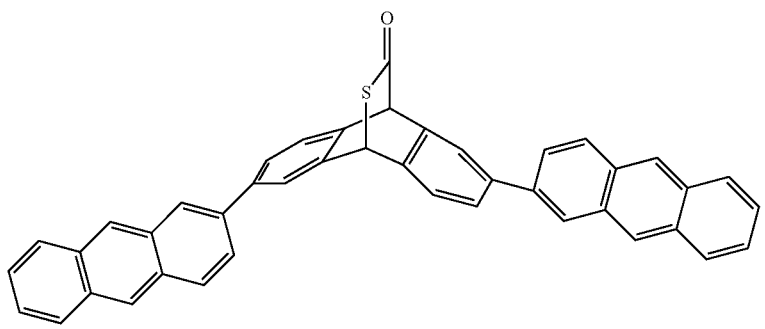
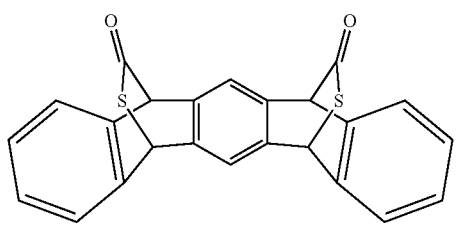
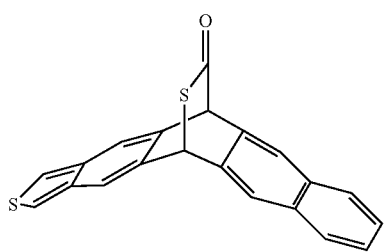
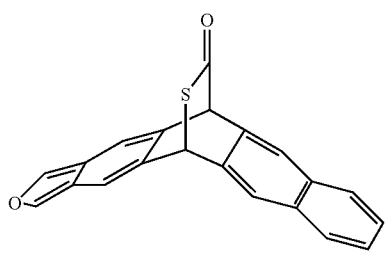
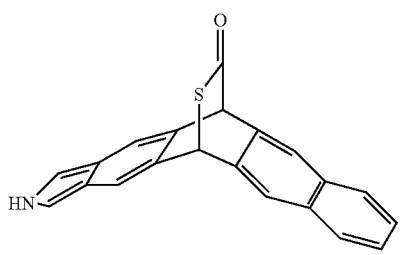
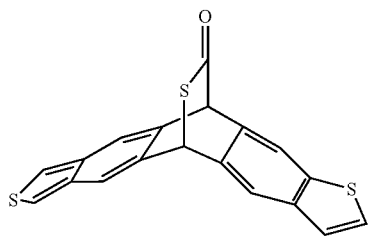
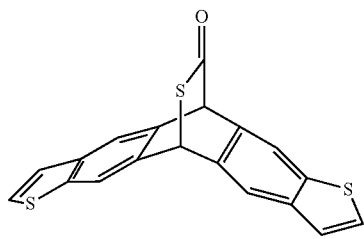
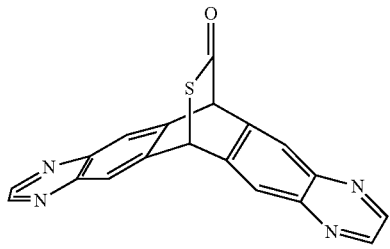
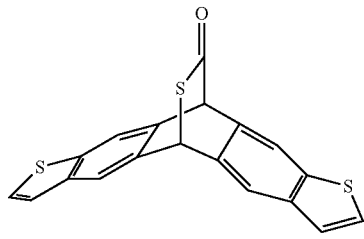
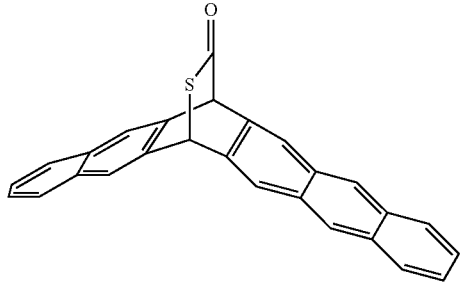
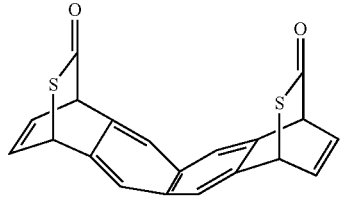

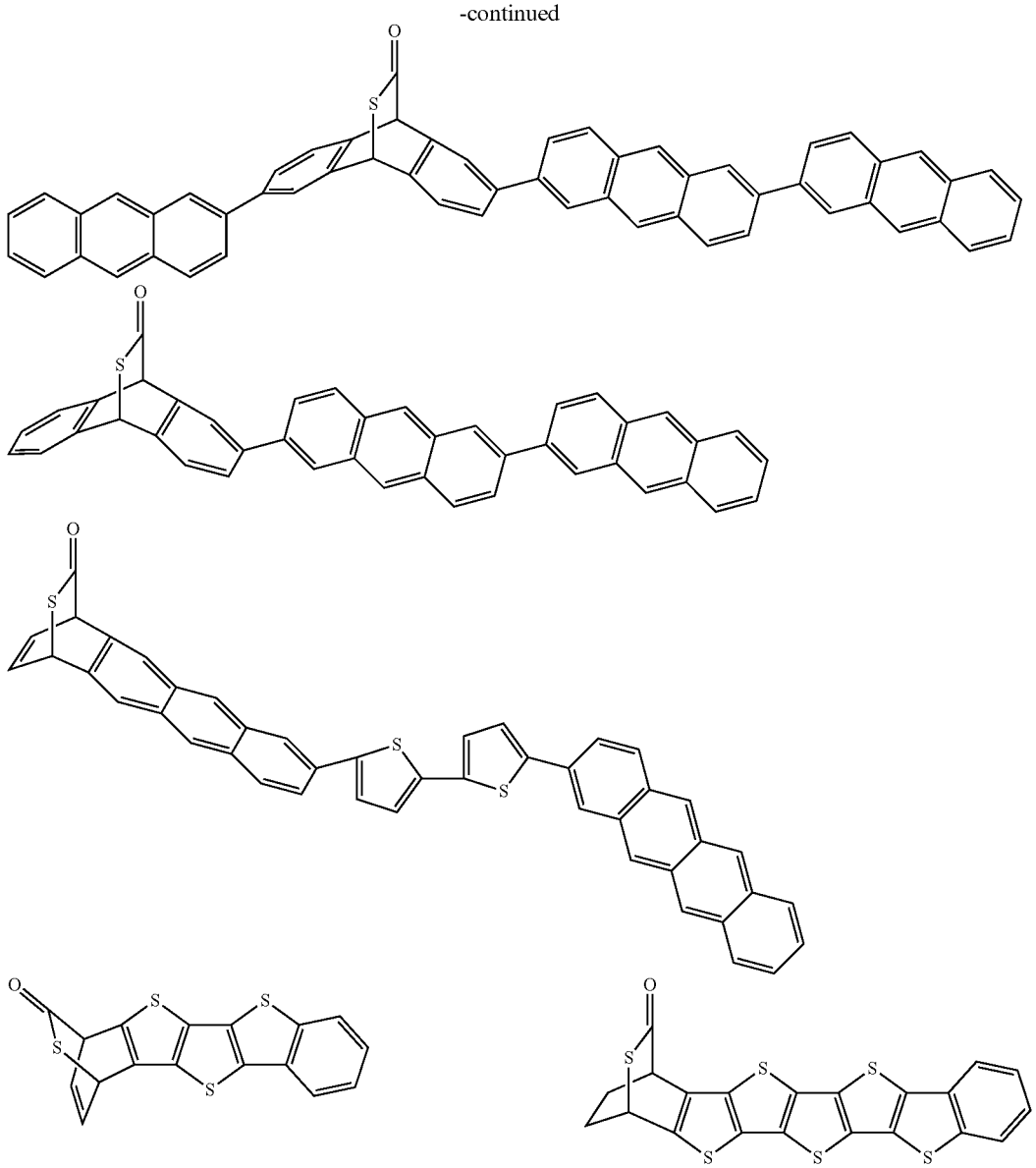

Any one of those organic semiconductor precursors is applied to the base body in step (I), whereby the layer composed of the organic semiconductor precursor is formed. A method of forming the layer composed of the organic semiconductor precursor is preferably a method in which the organic semiconductor precursor is dissolved in an organic solvent and applied. An organic solvent to be used for dissolving the organic semiconductor precursor is not particularly limited as long as an organic semiconductor material neither reacts with the solvent nor precipitates. Examples of the solvent include acetone, methylethyl ketone, methylisobutyl ketone, cyclohexanone, hexane, heptane, cyclohexane, tetrahydrofuran, dioxane, diethyl ether, isopropyl ether, dibutyl ether, toluene, xylene, 1,2-dimethoxyethane, chloroform, methylene chloride, dichloroethane, 1,2-dichloroethylene, dimethylsulfoxide, N-methyl pyrrolidone, chlorobenzene, dichlorobenzene, and trichlorobenzene. The concentration of the solution is arbitrarily adjusted depending on a desired thickness, and is preferably 0.01 wt % or more and 5 wt % or less. Taking into account the surface smoothness and thickness uniformity of a coating film, a solvent is desirably selected. In addition, two or more kinds of organic solvents may be used as a mixture, and a polar solvent is particularly preferably mixed in the mixture. This is because the mixing of the polar solvent is expected to alleviate orientation resulting from the dipole of the SCO skeleton to lead the skeleton to a better orientation state, whereby the semiconductor characteristic of the precursor improves, though the reason for the expectation is unclear. Examples of the polar solvent to be mixed include nitrile-, ester-, alcohol-, and cyclic ether-type solvents such as acetonitrile, ethyl acetate, acetone, methyl ethyl ketone, acetylacetone, tetrahydrofuran, dioxane, methanol, ethanol, n-propanol, isopropanol, n-butanol, and N-methylpyrrolidone. Of those, an alcohol-type solvent such as methanol, ethanol, 1-propanol, isopropanol, or n-butanol is particularly preferably mixed. The ratio at which the polar solvent is mixed, which is not particularly limited as long as the organic semiconductor precursor neither reacts with the solvent nor precipitates, is preferably such that the molar ratio of the organic semiconductor precursor and the polar solvent (polar solvent/organic semiconductor precursor) is 2 or more and 30 or less.

A method of forming layer composed of the organic semiconductor precursor is not particularly limited. The formation method is performed by means of any one of the conventional coating methods such as a spin coating method, a cast method, a spray coating method, a doctor blade method, a die coating method, a dipping method, a printing method, an inkjet method, and a dropping method. Examples of the printing method include screen printing, offset printing, gravure printing, flexographic printing, and microcontact printing. Of those application methods, the spin coating method, the dipping method, the spray coating method, and the inkjet method are preferable because the application amount can be controlled so that a film having a desired thickness is formed. To prevent the intrusion of dust and the like in a coating film as much as possible, it is desirable to filter the solution in advance by means of a membrane filter. This is because the intrusion of insoluble matter or dust from the outside may obstruct uniform orientation, thereby increasing an OFF current and reducing an ON/OFF ratio. In addition, the coating film of the organic semiconductor precursor can be subjected to preliminary drying.

The layer formed of the organic semiconductor precursor thus formed is heated or irradiated with light in step (II), whereby such reverse Diels-Alder reaction as shown in the reaction formula (3) is brought about, and the layer composed of the organic semiconductor is formed. When the layer formed of the organic semiconductor is formed by heating, heat to be applied to the layer composed of the organic semiconductor precursor, which is only required to have such a temperature that the precursor is converted into the organic semiconductor, is preferably heat at 100° C. or higher and 250° C. or lower. In addition, when the layer composed of the organic semiconductor is formed by irradiation with light, the wavelength of light with which the layer composed of the organic semiconductor precursor is irradiated, is only required to fall within an absorption wavelength region of the organic semiconductor precursor, and falls within a wavelength region of preferably 190 nm or more and 350 nm or less, or more preferably 220 nm or more and 280 nm or less. When the wavelength falls within the above region, the precursor can be efficiently converted into the organic semiconductor. A light source is selected from, for example, a tungsten lamp, a halogen lamp, a metal halide lamp, a sodium lamp, a xenon lamp, a high-pressure mercury lamp, a low-pressure mercury lamp, and various laser light beams. A method of irradiating the layer with light is not particularly limited as long as the organic semiconductor precursor is changed to the organic semiconductor, but a method of directly irradiating the organic semiconductor precursor with light is desirable in order that a photoreaction may be more effectively performed. When heat generated by the irradiation with light is applied to the organic semiconductor precursor, the heat is preferably cut off with a heat absorbing filter or the like. In addition, the organic semiconductor can be patterned by irradiating the layer with light through a mask. It is more preferable that light and heat be simultaneously applied to the layer composed of the organic semiconductor precursor in order that an excellent crystallized film of the organic semiconductor may be obtained. In this case, heat is applied by heating the base body from the outside of the body. Any method may be employed as a heating method, but a preferable method is a method involving heating the base body on a hot plate, or in an oven with hot air circulation or a vacuum oven. Of those, in the present invention, a method involving heating the base body on a hot plate is more preferable. While the optimum temperature at which the base body is heated varies depending on the type of organic semiconductor precursor, the base body is preferably heated in the temperature region of 50° C. or higher and 180° C. or lower in consideration of, for example, an influence on the peripheral part of the layer.

As describe above, the concept of the term "or" includes "and", and the heat and irradiation with light may be performed simultaneously. When light and heat are simultaneously applied to the layer, the time period for which light and heat are simultaneously applied to the layer varies depending on, for example, the thickness and material of the layer to a large extent, so the time period cannot be uniquely determined. In general, however, it becomes difficult for light to permeate into a deep portion of the crystallized film of the organic semiconductor as the film grows, so the time period for which light energy and heat energy are simultaneously applied to the layer is preferably 1 second or longer and 30 minutes or shorter. In such a manner, light can be effectively utilized in converting the organic semiconductor precursor into the organic semiconductor. The time period for which light energy and heat energy are simultaneously applied to the layer is more preferably minute or longer and 15 minutes or shorter. In addition, in order to obtain a more stable crystallized film, only heat energy may be further applied after simultaneously applying light energy and heat energy.

The layer formed of the organic semiconductor obtained through those operations has a thickness of preferably 10 nm or more and 500 nm or less, or more preferably 20 nm or more and 200 nm or less. The thickness can be measured with, for example, a surface roughness meter or a level difference meter.

Figure 2:
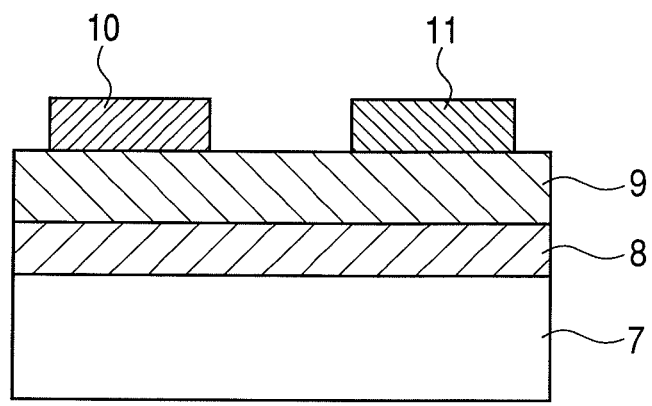
FIG. 2 is a schematic sectional view showing a structure of a top electrode type field effect transistor in an example of the present invention.

FIG. 2 shows the schematic sectional view of an organic field effect transistor when the organic field effect transistor is obtained through the above steps. The field effect transistor shown in FIG. 2 is made up of a gate electrode 7, an insulating layer 8, a layer 9 composed of an organic semiconductor, a source electrode 10, and a drain electrode 11. Description is given here on the assumption that a base body is comprised of the gate electrode 7 and the insulating layer 8.

The gate electrode 7, the source electrode 10, and the drain electrode 11 are not particularly limited as long as they are made of conductive materials. Examples of the materials include: platinum, gold, silver, nickel, chromium, copper, iron, tin, antimonial lead, tantalum, indium, aluminum, zinc, magnesium, and alloys of those metals; conductive metal oxides such as an indium-tin oxide; and inorganic and organic semiconductors with increased conductivity through doping and the like, such as a silicon single crystal, polysilicon, amorphous silicon, germanium, graphite, polyacetylene, polyparaphenylene, polythiophene, polypyrrole, polyaniline, polythienylenevinylene, and polyparaphenylenevinylene. Examples of a method of producing an electrode include a sputtering method, an evaporation method, a printing method from a solution or a paste, an inkjet method, and a dipping method. In addition, an electrode material is preferably any of the above materials that have low electrical resistance at a contact surface with the semiconductor layer.

The insulating layer 8 is not limited as long as the layer formed of the organic semiconductor can be uniformly applied to the layer, but the insulating layer is preferably one having a high dielectric constant and low conductivity. Examples of a material for the insulating layer include: inorganic oxides and nitrides such as silicon oxide, silicon nitride, aluminum oxide, titanium oxide, and tantalum oxide; polyacrylate; polymethacrylate; polyethylene terephthalate; polyimide; and polyether. Of those materials for the insulting layer, a material having high surface smoothness is preferable.

A field effect transistor structure in the present invention may be any one of a top contact electrode type, a bottom contact electrode type, and a top gate electrode type. In addition, the structure is not limited to a horizontal type structure, and may be a vertical type structure (structure in which one of a source electrode and a drain electrode is present on the surface of an organic semiconductor layer on the side of a base material and the other is present on the surface of the organic semiconductor layer on the side opposite to the base material).

EXAMPLES

Synthesis Example 1

Step (1)
2,4-pentanedione (205.4 ml, 2.0 mol), acetone (100 ml), n-butyl bromide (54 ml, 0.5 mol), and potassium carbonate (34.55 g, 0.25 mol) were fed into a reaction vessel, air in the vessel was replaced with nitrogen, and reflux was carried out for 48 hours. The resultant solid was filtered out, and the solvent was distilled off by means of an evaporator. After that, unreacted 2,4-pentanedione was distilled off under reduced pressure by means of a diaphragm. Then, the remainder was distilled in a vacuum to yield 3-n-butyl 2,4-petanedione (43.25 g, 55% yield).

Step (2)
Benzyl acetoacetate (97 ml, 560 mmol) and acetic acid (81 ml) were fed into a reaction vessel. Then, a solution of sodium nitrite (37.8 g) in water (115 ml) was dropwise added into the mixture at 10° C. or lower. After the dropping, the mixture was stirred for 3 hours at room temperature. A solution of 3-n-butyl 2,4-pentanedione (43.16 g, 280 mmol) obtained in Step (1) in acetic acid (45 ml), a mixture of zinc powder (36.6 g) and sodium acetate (25.9 g), and the above solution were fed into another vessel at 60° C. or lower, and was stirred at 80° C. for 1 hour. After that, the reaction solution was poured into ice water (1.12 L), and the resultant precipitate was filtered and washed with water. The precipitate was dissolved in chloroform and washed with water, a saturated aqueous solution of sodium bicarbonate, and a saturated salt solution. The organic layer was dried over anhydrous sodium sulfate, concentrated, and distilled under reduced pressure by means of a diaphragm to remove an excess liquid. The remainder was purified by means of silica gel column chromatograghy (EtOAc/Hexane) and recrystallized (MeOH) to yield 4-n-butyl-3,5-dimethylpyrrole benzylester (22.92 g, 24% yield).

Step (3)
Acetic acid (200 ml) and acetic anhydride (3.09 ml) were fed into a reaction vessel. 4-n-butyl-3,5-dimethylpyrrole benzylester (8.56 g, 30 mmol) was dissolved into the mixture, and then lead tetraacetate (15.38 g, 31.5 mmol) was slowly added to the solution. After the mixture had been stirred for 2 hours, and the reaction solution was poured into the ice water. The produced precipitate was filtered, and was thoroughly washed with water. The precipitate was dissolved into chloroform, and was washed with water, a saturated aqueous solution of sodium bicarbonate, and a saturated salt solution. The organic layer was dried over anhydrous sodium sulfate, concentrated under reduced pressure, and subjected to trituration with hexane to yield benzyl 5-acetoxymethyl-4-n-butyl-3-methylpyrrole-2-carboxylate (8.93 g, 87% yield).

Step (4)
Air in a reaction vessel was replaced with nitrogen, and 1-nitropropane (8.93 ml, 100 mmol) and dehydrated tetrahydrofuran (dry-THF) (50 ml) were added to the vessel. Then, 1,8-diazabicyclo[5.4.0]undec-7-ene (DBU) (1.5 ml, 10 mmol) was added to the mixture. After that, propionaldehyde (4.68 ml, 100 mmol) was added to the mixture while being was cooled on an ice bath. After the mixture had been stirred at room temperature for 10 hours, ethyl acetate (100 ml) was added to the mixture, and was washed with dilute hydrochloric acid, water, and a saturated salt solution, and the organic layer was dried over anhydrous sodium sulfate and concentrated under reduced pressure, whereby 4-hydroxy-3-nitrohexane was obtained (12.33 g, 84% yield).

Step (5)
4-hydroxy-3-nitrohexane (14.7 g, 100 mmol), acetic anhydride (14.8 ml, 157.3 mmol), chloroform (50 ml), and several drops of concentrated sulfuric acid were fed into a reaction vessel, and the mixture was stirred at room temperature for 10 hours. After the completion of the reaction, chloroform (50 ml) was added, and washed with water, a 5% aqueous solution of sodium bicarbonate, and a saturated salt solution. The organic layer was dried over anhydrous sodium sulfate and concentrated under reduced pressure to yield 4-acetoxy-3-nitrohexane (16.3 g, 86% yield).

Step (6)
After 4-acetoxy-3-nitrohexane (11.34 g, 60 mmol) had been added to a reaction vessel, air in the vessel was replaced with nitrogen, and dry-THF (150 ml) and ethyl isocyanoacetate (7.28 ml, 66 mmol) were added. Then, DBU (20.76 ml, 144 mmol) was slowly dropwise added while being cooled on an ice bath, and stirred at room temperature for 12 hours. After the completion of the reaction, 1N hydrochloric acid was added, and extracted with chloroform, and the extract was washed with water and a saturated salt solution. The organic layer was dried over anhydrous sodium sulfate and concentrated under reduced pressure. After that, the concentrated product was purified by means of silica gel column chromatography to yield ethyl 3,4-diethylpyrrole-2-carboxylate (10.97 g, 94% yield).

Step (7)
Ethyl 3,4-diethylpyrrole-2-carboxylate obtained in Step (6) (2.056 g, 10.53 mmol), ethylene glycol (100 ml), and potassium hydroxide (3.5 g) were placed in a light-shielded reaction vessel equipped with a reflux condenser. Then, the inside of the reaction vessel was replaced with nitrogen and the mixture was stirred at 160° C. for 2.5 hours. After that, the reaction solution cooled to room temperature was poured into ice water, and extracted with ethyl acetate, and the extract was washed with an aqueous solution of sodium bicarbonate, water, and a saturated salt solution. The organic layer was dried over anhydrous sodium sulfate and concentrated under reduced pressure, thereby to obtain 3,4-diethylpyrrole. Again, 3,4-diethylpyrrole obtained by this reaction, benzyl-5-acetoxymethyl-4-n-butyl-3-methylpyrrole-2-carboxylate obtained in Step (3) (7.21 g, 21 mmol), acetic acid (10 ml), and ethanol (150 ml) were fed into a light-shielded reaction vessel equipped with a reflux condenser, and was refluxed for 18 hours. After the reflux, the resultant was cooled to room temperature, ethanol (50 ml) was added, and was left standing at 0° C. for 5 hours. The precipitated crystal was filtered out and thoroughly washed with ethanol to yield 2,5-bis(5-benzylcarbonyl-3-n-butyl-4-methyl-2-pyrroylmethyl)-3,4-dimethyl-1H-pyrrole (5.25 g, 72% yield).

Step (8)
Palladium carbon (Pd/C) (0.5 g) and dry-THF (20 ml) were fed into a three-necked flask, and air in the flask was replaced with hydrogen, and stirring was carried out for 30 minutes. A solution prepared by dissolving 2,5-bis(5-benzylcarbonyl-3-n-butyl-4-methyl-2-pyrroylmethyl)-3,4-dimethyl-1H-pyrrole (2.09 g, 3.03 mmol) in dry-THF (30 ml) was slowly dropwise added into the mixture, and was stirred at room temperature overnight. After the stirring, the solution was subjected to Celite filtration. The filtrate was concentrated under reduced pressure, shielded from light, and cooled on an ice bath in a nitrogen atmosphere. Trifluoro acetate (TFA) (5 ml) was dropwise added, and was stirred for 10 minutes. After that, trimethyl orthoformate ($CH(OMe)_3$) (10 ml) was slowly dropwise added, and was stirred at 0° C. for 1 hour. After the solution had been neutralized with 1M NaOH (which had been diluted with a solution of $MeOH/H_2O=1/1$), the resultant was poured into ice water. As a result, a brown solid precipitated. The solid was filtered out, washed with water, and rinsed with hexane to yield 2,5-bis(5-formyl-3-n-butyl-4-methyl-2-pyrroylmethyl)-3,4-diethyl-1H-pyrrole (1.94 g, 60% yield).

Step (9)

1,4-cyclohexadiene (73.77 ml, 0.78 mmol) was placed in a three-necked flask, stirred, and cooled to −45° C. A solution of bromine (122.5 g, 0.77 mmol) in hexane (350 ml) was slowly dropwise added to the flask over 4 hours or longer. After the completion of the dropping, the reaction solution was returned to room temperature and filtrated, and the filtrate was concentrated and dried under reduced pressure, whereby 4,5-dibromo-1-cyclohexene was obtained (146.5 g, 79%).

Step (10)

The compound obtained in Step (9) (80.5 g, 338 mmol), water (500 ml), acetone (250 ml), and N-methylmorpholine (45.5 g, 389 mmol) were placed in a reaction vessel, and was stirred. $OsO_4$ (1 g) was added to the mixture, and was vigorously stirred for 24 hours. After the completion of the reaction, a suspension of $NaHSO_3$ (50 g) and Florisil (250 g) in water (100 ml) was added to the reaction solution, and was stirred for 10 minutes. After that, insoluble matter was removed by celite filtration, and 5% HCl was added to the filtrate until the pH of the filtrate became 3. Upon confirming that the pH had reached 3, and acetone was removed under reduced pressure. Organic matter was extracted from the remainder with ethyl acetate, dried over sodium sulfate, and concentrated under reduced pressure. The precipitated crystals were filtrated, and was then recrystallized with methylene chloride, whereby 4,5-dibromo-1,2-cyclohexanediol was obtained (64.6 g, 70%).

Step (11)

The compound obtained in Step (10) (20.6 g, 75.62 mmol) was placed in a reaction vessel, and air in the vessel was replaced with nitrogen. 2,2-dimethoxypropane (12.92 ml) and p-toluenesulfonic acid (0.9 g) were added to the vessel, and the mixture was stirred for 3 hours. After the completion of the reaction had been confirmed, the mixture was filtrated through activated alumina, and the filtrate was concentrated under reduced pressure, whereby 5,6-dibromo-2,2-dimethyl-hexahydro-1,3-benzodioxol was obtained (17.1 g, 72%).

Step (12)

The compound obtained in Step (11) was placed in a reaction vessel, and air in the vessel was replaced with nitrogen. After that, the compound was dissolved in dehydrated toluene (116 ml). Distilled DBU (6.0 ml, 40.1 mmol) was added to the solution, and the mixture was refluxed for 6 hours. After the reaction product had been filtrated, sodium hydrogen carbonate was added to the filtrate, and the organic layer was dried over magnesium sulfate, whereby 2,2-dimethyl-3a,7a-dihydrobenzo[1.3]dioxol was obtained. The compound was used in the next reaction without being further purified.

Step (13)

Trans-1,2-bis(phenylsulfonyl)ethylene (1.37 g, 4.45 mmol) was added to a solution of the compound obtained in Step (12) in toluene, and air in a vessel containing the mixture was replaced with nitrogen. After having been refluxed for 8 hours, the mixture was concentrated under reduced pressure. The resultant reaction product was purified by silica gel chromatography (50% EtOAc/Hexane), whereby 10,11-bis(phenylsulfonyl)-4,4-dimethyl-3,5-dioxa-tricyclo[5.2.2.0$^{2.6}$]undec-8-ene was obtained (2.0 g, 98%).

Step (14)

The compound obtained in Step (13) (4.0 g, 8.7 mmol) was placed in a reaction vessel, and air in the vessel was replaced with nitrogen. After that, the compound was dissolved in tetrahydrofuran (24 ml). Ethyl isocyanoacetate (1.3 ml, 12.2 mmol) and 1M t-BuOK (tetrahydrofuran solution) (21.7 ml, 21.7 mmol) were added to the solution on an ice bath. Thereafter, the mixture was stirred at room temperature for 18 hours. A 10% HCl aqueous solution (24.4 ml) and 160 ml of water were added to the reaction solution, and then the mixture was extracted with ethyl acetate, washed with a saturated salt solution, dried over anhydrous sodium sulfate, and concentrated under reduced pressure. The resultant reaction product was purified by silica gel chromatography, whereby a target product represented by a general formula (a) was obtained (2.4 g, 95%).

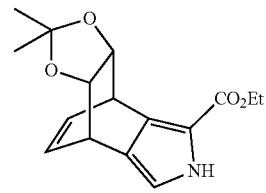

General formula (a)

Step (15)

The compound obtained in Step (14) (1 g, 3.45 mmol), ethylene glycol (50 ml), and potassium hydroxide (0.8 g) were placed in a reaction vessel, and air in the vessel was replaced with nitrogen. After that, the mixture was stirred at 175° C. for 5 hours. Thereafter, the reaction solution was returned to room temperature and poured into water, and was then extracted with ethyl acetate, washed with water and a saturated salt solution, and purified by silica gel chromatography, whereby a target product represented by a general formula (b) was obtained (0.52 g, 70%).

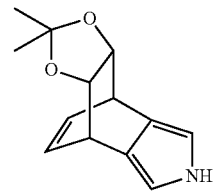

General formula (b)

Step (16)

Methylene chloride (300 ml) and trichloroacetic acid (8.43 g) were placed into a reaction vessel, and air in the vessel was replaced with nitrogen. A liquid prepared by dissolving the compound synthesized in Step (8) (0.79 g, 1.7 mmol) and the compound synthesized in Step (15) (0.37 g, 1.7 mmol) in methylene chloride (125 ml) was dropwise added to the mixture over 15 minutes. After that, the mixture was stirred at room temperature for 20 hours, and was then neutralized with triethylamine. Chloranil was added to the neutralized product, and the mixture was stirred for 2.5 hours. The reaction solution was poured into water, and the mixture was extracted with methylene chloride, washed with a saturated sodium bicarbonate solution and water, dried over anhydrous sodium sulfate, concentrated under reduced pressure, and purified by alumina column chromatography, whereby a compound represented by a general formula (c) was obtained (0.18 g, 16%).

General formula (c)

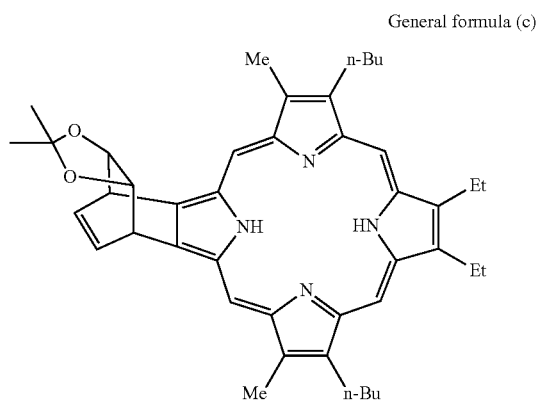

Step (17)

The compound obtained in Step (16) was placed in a reaction vessel and dissolved in tetrahydrofuran, and 6N HCl was added to the solution. After that, the mixture was stirred at room temperature. Thereafter, the reaction solution was poured into water, and the mixture was extracted with ethyl acetate, washed with water, dried over anhydrous sodium sulfate, and concentrated under reduced pressure, whereby a compound represented by a general formula (d) was obtained.

General formula (d)

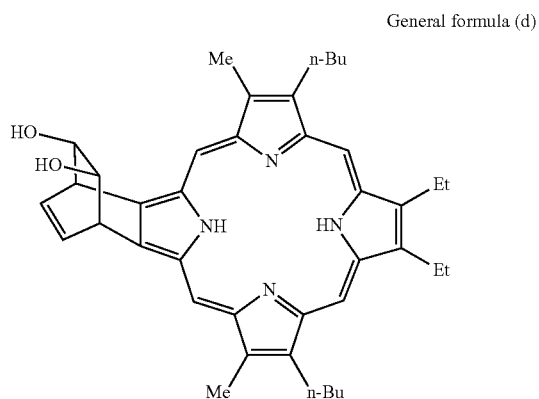

Step (18)

Air in a reaction vessel was replaced with nitrogen, and dimethyl sulfoxide (0.8 ml) and methylene chloride (2.1 ml) were added to the vessel. After that, trifluoroacetic anhydride (1.0 ml) was dropwise added to the mixture at −60° C., and was stirred for 10 minutes. Thereafter, a solution of the compound represented by the general formula (d) obtained in Step (17) (39 mg, 0.063 mmol) in dimethyl sulfoxide was dropwise added to the mixture at −60° C., and was stirred for 1.5 hours. Then, triethylamine (2.5 ml) was added to the mixture at −60° C., and was stirred for an additional 1.5 hours. After that, the reaction solution was returned to room temperature and poured into a 10% HCl aqueous solution, and the mixture was extracted with methylene chloride, washed with water, dried over anhydrous sodium sulfate, concentrated under reduced pressure, and purified by silica gel chromatography, whereby a compound represented by a general formula (e) was obtained (24 mg, 62% yield). $^1$H NMR (CDCl$_3$) δ=10.13, 7.39, 6.14, 4.15, 4.01, 3.71, 2.31, 1.90, 1.73, 1.11, −3.89

Infrared absorption spectrum (ATR) cm$^{-1}$: 1,739 (CO)
Mass spectrum (MALDI-TOF-MS) m/z: 556.358, 613.441

General formula (e)

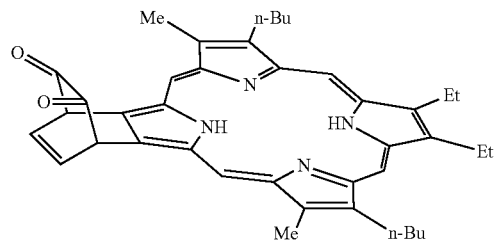

Synthesis Example 2

Step (1)

The compound represented by the general formula (a) synthesized in Step (14) of Synthesis Example 1 (0.29 g, 1.0 mmol) was placed in a reaction vessel, and air in the vessel was replaced with nitrogen. The compound was dissolved in anhydrous tetrahydrofuran (5.0 ml), and the reaction vessel was immersed in an ice bath. Lithium aluminum hydride (0.11 g, 3.0 mmol) was added to the solution, the ice bath was removed, and the mixture was stirred at room temperature for 1 hour. After the completion of the reduction, a saturated salt solution (20 ml) was added to the mixture, insoluble matter was subjected to celite filtration, and the remainder was extracted with chloroform and dried over anhydrous sodium sulfate. p-toluenesulfonic acid (0.08 g) was added to the solution, and the mixture was stirred for 1 day. Further, chloranil (0.22 g, 0.91 mmol) was added to the mixture, and was stirred for an additional 1 day. After the completion of the reaction, the reaction solution was washed with a 1% sodium thiosulfate aqueous solution and a saturated salt solution, dried over anhydrous sodium sulfate, concentrated under reduced pressure, purified by silica gel column chromatography, and recrystallized, whereby a compound represented by a general formula (f) was obtained (0.05 g, 21%).

General formula (f)

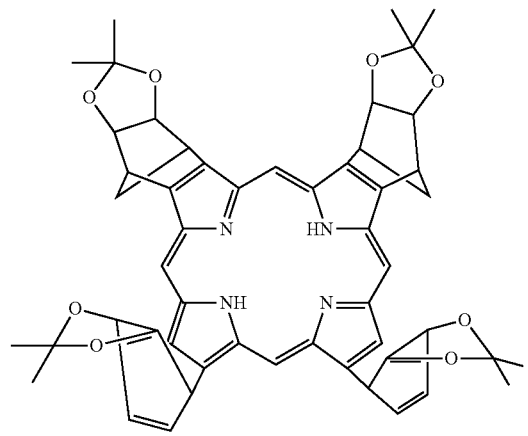

Step (2)

The compound represented by the general formula (f) synthesized in Step (1) of Synthesis Example 2 was placed into a reaction vessel, and air in the vessel was replaced with nitrogen. After that, the compound was dissolved in tetrahydrofuran. A 1M HCl aqueous solution was added in an amount equal to that of tetrahydrofuran to the solution, and the mixture was stirred for 4 hours. After the completion of the reaction, the mixture was extracted with ethyl acetate, washed with water and a saturated salt solution, dried over anhydrous sodium sulfate, concentrated under reduced pressure, purified by silica gel chromatography, and recrystallized, whereby a compound represented by a general formula (g) was obtained (84%).

General formula (g)

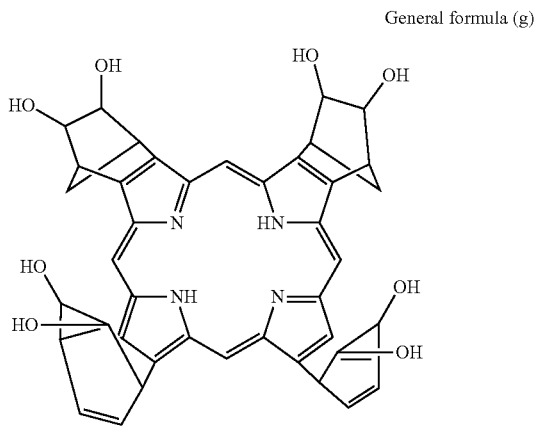

Step (3)

Air in a reaction vessel was replaced with nitrogen, and dimethyl sulfoxide (0.8 ml) and methylene chloride (5.0 ml) were added to the vessel. After that, trifluoroacetic anhydride (1.2 ml) was dropwise added to the mixture at −60° C., and was stirred for 10 minutes. Thereafter, a solution of the compound represented by the general formula (g) obtained in Step (2) of Synthesis Example 2 (50 mg, 0.067 mmol) in dimethyl sulfoxide (0.5 ml) was dropwise added to the mixture at −60° C., and was stirred for 1.5 hours. Then, triethylamine (2.7 ml) was added to the mixture at −60° C., and was stirred for an additional 1.5 hours. After that, the reaction solution was returned to room temperature and poured into a 10% HCl aqueous solution, and was extracted with methylene chloride, washed with water and a saturated salt solution, dried over anhydrous sodium sulfate, concentrated under reduced pressure, and triturated with ethyl acetate, whereby a compound represented by a general formula (h) was obtained (15 mg, 30%).

$^1$H NMR (CDCl$_3$) δ=9.99, 7.51, 6.20

Infrared absorption spectrum (ATR) cm$^-$: 1,728 (CO)

Mass spectrum (MALDI-TOF-MS) m/z: 510.291 (only the mass of a benzo body was observed because a carbonyl group was eliminated during ionization).

General formula (h)

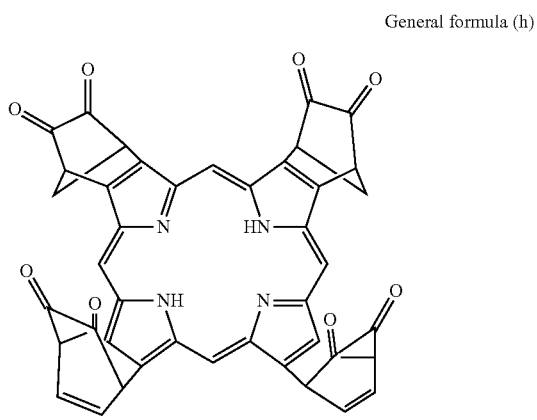

Step (4)

The compound represented by the general formula (f) and zinc acetate were allowed to react with each other, whereby a zinc complex was obtained. The resultant compound (1.0 g), THF (100 ml), and 1N HCl (100 ml) were mixed, and air in a reaction vessel containing the mixture was replaced with nitrogen. After that, the mixture was stirred at 65° C. for 3 hours and returned to room temperature. The reaction solution was concentrated, and then the concentrate was dissolved in ethanol. The solution was passed through sodium hydrogen carbonate so as to be concentrated again. After that, the resultant compound was purified by silica gel column chromatography, whereby a zinc complex of the compound represented by the general formula (g) was quantitatively obtained.

Step (5)

Air in a reaction vessel was replaced with nitrogen, and dimethyl sulfoxide (0.93 ml) and methylene chloride (5.4 ml) were added to the vessel. After that, trifluoroacetic anhydride (1.3 ml) was dropwise added to the mixture at −60° C., and was stirred for 10 minutes. After that, a solution of the zinc complex of the compound represented by the general formula (g) obtained in Step (4) of Synthesis Example 2 (59 mg, 0.072 mmol) in dimethyl sulfoxide (1.0 ml) was dropwise added to the mixture at −60° C., and was stirred for 1.5 hours. After that, triethylamine (3.0 ml) was added to the mixture at −60° C., and was stirred for an additional 1.5 hours. After that, the reaction solution was returned to room temperature and poured into a 10% aqueous solution of HCl, and the mixture was extracted with methylene chloride, washed with water and a saturated salt solution, dried over anhydrous sodium sulfate, concentrated under reduced pressure, and triturated with ethyl acetate, whereby a zinc complex of the compound represented by the general formula (h) was obtained (16 mg, 28%).

$^1$H NMR (CDCl$_3$) δ=10.17 (4H, m), 7.45 (8H, m), 6.18 (8H, m)

Infrared absorption spectrum (ATR) cm$^{-1}$: 1,728 (CO)

Mass spectrum (MALDI-TOF-MS) m/z: 510.329 (only the mass of a benzo body was observed because a carbonyl group and zinc as a central metal were eliminated during ionization).

Step (6)

The compound represented by the general formula (h) and copper acetate were allowed to react with each other, whereby a copper complex was quantitatively obtained.

Infrared absorption spectrum (ATR) cm$^{-1}$: 1,728 (CO)

Mass spectrum (MALDI-TOF-MS) m/z: 510.303 (only the mass of a benzo body was observed because a carbonyl group and copper as a central metal were eliminated during ionization).

Synthesis Example 3

Step (1)

Phosphorus pentoxide (17 g, 60 mmol) was placed in a three-necked flask, and air in the flask was replaced with nitrogen. In the presence of P$_2$O$_5$, sulfolane distilled under reduced pressure (70 ml) was placed in the flask. Acetylene dicarboxyamide (5 g, 45 mmol) suspended in sulfolane was dropwise added to the mixture at 110° C. and 12 Torr over 30 minutes or more.

After the completion of the dropping, the temperature of the reaction liquid was set at 120° C., where produced dicyanoacetylene was vaporized, and hence, was recovered while being cooled in a dry ice-acetone bath (0.85 g, 25%).

Step (2)

Air in an egg plant flask containing dicyanoacetylene (0.38 g, 5.0 mmol) was replaced with nitrogen, and toluene was added to dissolve dicyanoacetylene. 2,2-dimethyl-3a,7a-dihydrobenzo[1.3]dioxol (0.31 g, 2.0 mmol) was added to the solution, and was stirred at room temperature overnight. After that, the resultant was washed with water and a saturated salt solution, dried over anhydrous sodium sulfate, concentrated under reduced pressure, and purified by silica gel column chromatography, whereby a compound represented by a general formula (i) was obtained (0.46 g, 40%).

General formula (i)

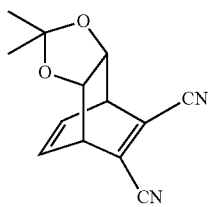

Step (3)

Magnesium (3.1 mg), dehydrated butanol (4.4 ml), and a slight amount of iodine were placed in a reaction vessel whose inside had been replaced with nitrogen, and stirred at 120° C. for 3 hours. The resultant solution (1.2 ml) was added to a reaction vessel which contained the compound represented by the general formula (i) obtained in Step (2) of Synthesis Example 3 (20 mg, 0.08 mmol) and whose inside had been replaced with nitrogen, and the mixture was stirred at 120° C. for 2 days. The reaction solution was poured into a solution containing water and methanol in a ratio of 1:1, and was extracted with chloroform. The organic layer was washed with water and a saturated salt solution, dried over anhydrous sodium sulfate, concentrated under reduced pressure, and separated by alumina column chromatography, whereby a compound represented by a general formula (j) was obtained (7% yield).

General formula (j)

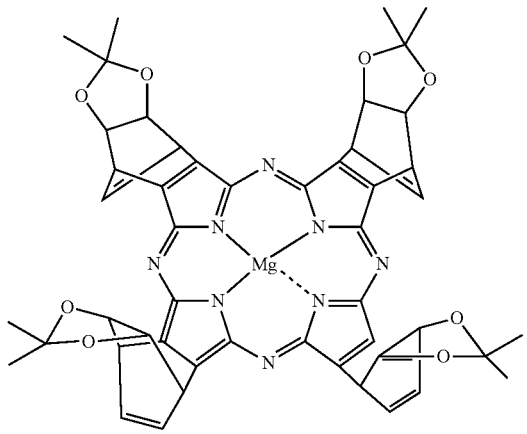

Step (4)

The compound represented by the general formula (j) obtained in Step (3) of Synthesis Example 3 is placed in a reaction vessel, air in the vessel is replaced with nitrogen, and the compound is dissolved in tetrahydrofuran. 1N hydrochloric acid is added to the solution, and the mixture is stirred at room temperature. After the completion of the reaction, the mixture is washed with a saturated salt solution, and the organic layer is dried over anhydrous sodium sulfate, concentrated under reduced pressure, purified by silica gel column chromatography, and recrystallized, whereby a compound represented by a general formula (k) can be obtained.

General formula (k)

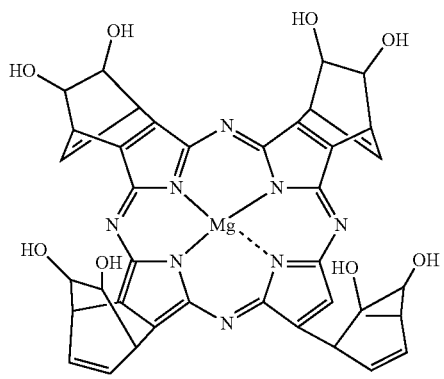

Step (5)

Air in a reaction vessel is replaced with nitrogen, and dimethyl sulfoxide and methylene chloride are added to the vessel. After that, trifluoroacetic anhydride is dropwise added to the mixture at −60° C., and stirred for 10 minutes. After that, a solution of the compound represented by the general formula (k) obtained in Step (4) of Synthesis Example 3 in dimethyl sulfoxide is dropwise added to the mixture at −60° C., and stirred for 1.5 hours. Thereafter, triethylamine is added to the mixture at −60° C., and stirred for an additional 1.5 hours. Then, the reaction solution is returned to room temperature, poured into a 10% HCl aqueous solution, extracted with methylene chloride, washed with water and a saturated salt solution, dried over anhydrous sodium sulfate, concentrated under reduced pressure, and purified by silica gel chromatography, whereby a compound represented by a general formula (l) can be obtained.

General formula (l)

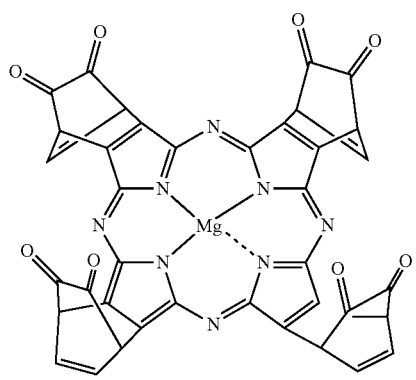

Synthesis Example 4

A reaction solution containing pentacene (0.46 g, 1.6 mmol) and thiophosgene (2 ml) was subjected to reaction at 65° C. for 6 hours. The reaction solution was cooled to room temperature, and dichloromethane (2 ml) was added to the reaction solution. After that, the mixture was filtrated so that unreacted pentacene was removed, and the filtrate was concentrated under reduced pressure. After the concentration, 40 ml of toluene were added to the concentrate, and the mixture was concentrated under reduced pressure so that unreacted thiophosgene was removed. The resultant product was purified by silica gel column chromatography, whereby a compound represented by a general formula (16) was obtained (40% yield).

General formula (16)

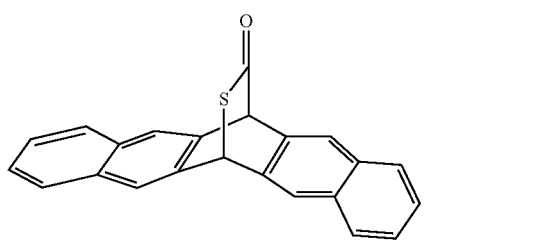

Preparation of Resin Solution a

Resin Solution a was prepared by dissolving 1.0 g of commercially available flaky methyl silsesquioxane (MSQ) (manufactured by SHOWA DENKO K.K.; trade name: GR650) in a mixed solvent composed of 49.5 g of ethanol and 49.5 g of 1-butanol.

Preparation of Resin Solution b 1.0 g of methyltrimethoxysilane was completely dissolved in a mixed solvent composed of 49.5 g of ethanol and 49.5 g of 1-butanol. 0.83 g of distilled water and 0.05 g of formic acid were added to the solution, and stirred at room temperature for 48 hours, whereby Silica Sol (Resin Solution) b was prepared.

Example 1

FIG. 1 shows the structure of a top electrode type field effect transistor in this example.

First, a highly doped N-type silicon substrate was defined as the gate electrode 1. A silicon oxide film having a thickness of 500 nm (5,000 Å) obtained by thermally oxidizing the surface layer of the silicon substrate was defined as the gate insulating layer 2. Next, Resin Solution a was applied to the surface of the insulating layer by a spin coating method (at the number of revolutions of 5,000 rpm). Next, the coating film was transferred to a hot plate, and was heated at 100° C. for 5 minutes and at 220° C. for 30 minutes. Thus, the A layer 3 (polysiloxane layer) was formed.

Next, a 1.0 wt % solution of the compound represented by the general formula (e) synthesized in Synthesis Example 1 in chloroform was applied onto the substrate on which the A layer 3 had been thus formed by a spin coating method at the number of revolutions of 900 rpm. Thus, a coating film was formed. Further, the substrate on which the coating film had been thus formed was mounted on a hot plate set at 150° C., and was irradiated with light from a metal halide lamp manufactured by NIPPON P.I. CO., LTD. (PCS-UMX250) through a heat absorbing filter and a blue filter for 5 minutes. Thus, the B layer 6 (organic semiconductor layer) was formed.

Au was vapor-deposited onto the B layer 6 by using a mask, whereby the source electrode 4 and the drain electrode 5 were formed. The conditions under which the electrodes were produced were as follows: a degree of vacuum in a vacuum device chamber was $1\times10^{-6}$ torr, and the temperature of the substrate was room temperature. The electrodes thus obtained each had a thickness of 100 nm.

A field effect transistor having a channel length L of 50 µm and a channel width W of 3 mm was produced by the foregoing procedure. The $V_d$-$I_d$ and $V_g$-$I_d$ curves of the produced transistor were measured with a parameter analyzer 4156C (trade name) manufactured by Agilent.

A mobility µ (cm²/Vs) of the transistor was calculated in accordance with the following equation (1).

$$I_d = \mu(C_i W/2L) \times (V_g - V_{th})^2 \qquad \text{(Eq. 1)}$$

In the equation, Ci represents the electrostatic capacity of the gate insulating layer per unit area (F/cm²), W and L represent the channel width (mm) and the channel length (µm) shown in the example, respectively, and $I_d$, $V_g$, and $V_{th}$ represent a drain current (A), a gate voltage (V), and a threshold voltage (V), respectively. In addition, a ratio of $I_d$ at $V_g$ of −80 V to $I_d$ at $V_g$ of 0 V at $V_d$ of −80 V was defined as an on/off ratio. The field effect mobility calculated from the obtained results was $1.8\times10^{-3}$ cm²/Vs. In addition, the on/off ratio was $3.1\times10^3$. In addition, the substrate of the transistor was subjected to CuKα X-ray diffraction measurement. As a result, a diffraction peak was observed, and it was confirmed that the substrate had satisfactory crystallinity.

Example 2

A highly doped N-type silicon substrate was defined as a gate electrode. A silicon oxide film having a thickness of 500 nm (5,000 Å) obtained by thermally oxidizing the surface layer of the silicon substrate was defined as a gate insulating layer. Next, a 1.0 wt % solution of the compound represented by the general formula (e) synthesized in Synthesis Example 1 in chloroform was applied onto the substrate by a spin coating method at the number of revolutions of 900 rpm. Thus, a coating film was formed. Further, the substrate on which the coating film had been thus formed was mounted on a hot plate set at 150° C., and was irradiated with light from a metal halide lamp manufactured by NIPPON P.I. CO., LTD. (PCS-UMX250) through a heat absorbing filter and a blue filter for 5 minutes. Thus, an organic semiconductor layer was formed.

Au was vapor-deposited onto the organic semiconductor layer by using a mask, whereby a source electrode and a drain electrode were formed. The conditions under which the electrodes were produced were as follows: a degree of vacuum in a vacuum device chamber was $1\times10^{-6}$ torr, and the temperature of the substrate was room temperature.

The electrodes thus obtained each had a thickness of 100 nm. A field effect transistor having a channel length L of 50 µm and a channel width W of 3 mm was produced by the foregoing procedure, and was evaluated for its electrical characteristics in the same manner as in Example 1. The transistor had a field effect mobility of $1.0\times10^{-5}$ cm²/Vs. In addition, the transistor had an on/off ratio of $3.6\times10^2$.

Example 3

A highly doped N-type silicon substrate was defined as a gate electrode. A silicon oxide film having a thickness of 500 nm (5,000 Å) obtained by thermally oxidizing the surface layer of the silicon substrate was defined as a gate insulating layer. Next, a 1.0 wt % solution of the compound represented by the general formula (16) synthesized in Synthesis Example 4 in chloroform was applied onto the substrate by a spin coating method at the number of revolutions of 1,000 rpm. Thus, a coating film was formed. Further, the substrate on which the coating film had been thus formed was mounted on a hot plate set at 120° C., and was irradiated with light from a UV light source manufactured by HOYA-SCHOTT (EX250) through a heat absorbing filter for 1 minute. Thus, an organic semiconductor layer was formed. Au was vapor-deposited onto the organic semiconductor layer by using a mask, whereby a source electrode and a drain electrode were formed. The conditions under which the electrodes were produced were as follows: a degree of vacuum in a vacuum device chamber was $1\times10^{-6}$ torr, and the temperature of the substrate was room temperature. The electrodes thus obtained each had a thickness of 100 nm. A field effect transistor having a channel length L of 50 μm and a channel width W of 3 mm was produced by the foregoing procedure. The $V_d$-$I_d$ and $V_g$-$I_d$ curves of the produced transistor were measured with a parameter analyzer 4156C (trade name) manufactured by Agilent.

The mobility μ (cm$^2$/Vs) of the transistor was calculated in accordance with the following equation (1).

$$I_d = \mu(CiW/2L)\times(V_g-V_{th})^2 \qquad \text{(Eq. 2)}$$

In the equation, Ci represents the electrostatic capacity of the gate insulating layer per unit area (F/cm$^2$), W and L represent the channel width (mm) and the channel length (μm) shown in the example, respectively, and $I_d$, $V_g$, and $V_{th}$ represent a drain current (A), a gate voltage (V), and a threshold voltage (V), respectively. In addition, a ratio $I_d$ at $V_g$ of $-80$ V to $I_d$ at $V_g$ of 0 V at $V_d$ of $-80$ V was defined as an on/off ratio. The field effect mobility calculated from the obtained results and the on/off ratio are shown in Table 1.

Example 4

A highly doped N-type silicon substrate was defined as a gate electrode. A silicon oxide film having a thickness of 500 nm (5,000 Å) obtained by thermally oxidizing the surface layer of the silicon substrate was defined as a gate insulating layer. Next, the compound represented by the general formula (16) synthesized in Synthesis Example 4 and ethanol were mixed in a molar ratio (ethanol/general formula (16)) of 7.8, and a 1.0 wt % solution was prepared by adding chloroform to the mixture. The solution was applied onto the substrate by a spin coating method at the number of revolutions of 1,000 rpm. Thus, a coating film was formed. Further, the substrate on which the coating film had been thus formed was mounted on a hot plate set at 140° C., and was heated for 30 minutes. Thus, an organic semiconductor layer was formed. Au was vapor-deposited onto the organic semiconductor layer by using a mask, whereby a source electrode and a drain electrode were formed. The conditions under which the electrodes were produced were as follows: a degree of vacuum in a vacuum device chamber was $1\times10^{-6}$ torr, and the temperature of the substrate was room temperature. The electrodes thus obtained each had a thickness of 100 nm. A field effect transistor having a channel length L of 50 μm and a channel width W of 3 mm was produced by the foregoing procedure, and was evaluated for its electrical characteristics. However, the transistor did not show transistor characteristics. Table 1 shows the results.

Example 5

A transistor was produced in the same manner as in Example 4 except that: the temperature of the hot plate was set at 200° C.; and the organic semiconductor layer was formed with the time period for which the substrate was heated changed to 1 minute, and the transistor was evaluated for its electrical characteristics. Table 1 shows the results.

Example 6

A highly doped N-type silicon substrate was defined as a gate electrode. A silicon oxide film having a thickness of 500 nm (5,000 Å) obtained by thermally oxidizing the surface layer of the silicon substrate was defined as a gate insulating layer. Next, the compound represented by the general formula (16) synthesized in Synthesis Example 4 and ethanol were mixed in a molar ratio (ethanol/general formula (16)) of 7.8, and a 1.0 wt % solution was prepared by adding chloroform to the mixture. The solution was applied onto the substrate by a spin coating method at the number of revolutions of 1,000 rpm. Thus, a coating film was formed. Further, the substrate on which the coating film had been thus formed was irradiated with light from a UV light source manufactured by HOYA-SCHOTT (EX250) through a heat absorbing filter at room temperature for 1 minute. Thus, an organic semiconductor layer was formed. Au was vapor-deposited onto the organic semiconductor layer by using a mask, whereby a source electrode and a drain electrode were formed. The conditions under which the electrodes were produced were as follows: a degree of vacuum in a vacuum device chamber was $1\times10^{-6}$ torr, and the temperature of the substrate was room temperature. The electrodes thus obtained each had a thickness of 100 nm. A field effect transistor having a channel length L of 50 μm and a channel width W of 3 mm was produced by the foregoing procedure, and was evaluated for its electrical characteristics. Table 1 shows the results.

Example 7

A highly doped N-type silicon substrate was defined as a gate electrode. A silicon oxide film having a thickness of 500 nm (5,000 Å) obtained by thermally oxidizing the surface layer of the silicon substrate was defined as a gate insulating layer. Next, the compound represented by the general formula (16) synthesized in Synthesis Example 4 and ethanol were mixed in a molar ratio (ethanol/general formula (16)) of 7.8, and a 1.0 wt % solution was prepared by adding chloroform to the mixture. The solution was applied onto the substrate by a spin coating method at the number of revolutions of 1,000 rpm. Thus, a coating film was formed. Further, the substrate on which the coating film had been thus formed was mounted on a hot plate set at 120° C. and irradiated with light from a UV light source manufactured by HOYA-SCHOTT (EX250) through a heat absorbing filter at room temperature for 1 minute. Thus, an organic semiconductor layer was formed. Au was vapor-deposited onto the organic semiconductor layer by using a mask, whereby a source electrode and a drain electrode were formed. The conditions under which the electrodes were produced were as follows: a degree of vacuum in a vacuum device chamber was $1\times10^{-6}$ torr, and the temperature of the substrate was room temperature. The electrodes thus obtained each had a thickness of 100 nm. A field effect transistor having a channel length L of 50 μm and a channel width W of 3 mm was produced by the foregoing procedure, and was evaluated for its electrical characteristics. Table 1 shows the results.

Example 8

A transistor was produced in the same manner as in Example 7 except that the temperature of the hot plate was set at 130° C., and the transistor was evaluated for its electrical characteristics. Table 1 shows the results.

Example 9

A transistor was produced in the same manner as in Example 7 except that the temperature of the hot plate was set at 140° C., and the transistor was evaluated for its electrical characteristics. Table 1 shows the results.

Example 10

A transistor was produced in the same manner as in Example 7 except that the temperature of the hot plate was set at 180° C., and the transistor was evaluated for its electrical characteristics. Table 1 shows the results.

TABLE 1

|  | Mobility (cm$^2$/Vs) | on/off |
| --- | --- | --- |
| Example 3 | $2.3 \times 10^{-2}$ | $9.6 \times 10^3$ |
| Example 4 | — | — |
| Example 5 | $2.3 \times 10^{-4}$ | $3.7 \times 10^4$ |
| Example 6 | $6.2 \times 10^{-5}$ | 29 |
| Example 7 | $5.0 \times 10^{-2}$ | $1.9 \times 10^3$ |
| Example 8 | $9.0 \times 10^{-2}$ | $4.2 \times 10^2$ |
| Example 9 | $1.0 \times 10^{-1}$ | $1.3 \times 10^2$ |
| Example 10 | $1.5 \times 10^{-4}$ | $1.4 \times 10^3$ |

Example 11

A 1.0 wt % solution of the compound represented by the general formula (16) in chloroform was prepared, and was applied onto a substrate by a spin coating method, whereby a film was formed.

Example 12

The compound represented by the general formula (16) and ethanol were mixed in a molar ratio (ethanol/general formula (16)) of 1.6, and a 1.0 wt % solution was prepared by adding chloroform to the mixture. The solution was applied onto a substrate by a spin coating method, whereby a film was formed.

Example 13

A film was formed in the same manner as in Example 12 except that the molar ratio was changed to 7.8.

Example 14

The compound represented by the general formula (16) and ethanol were mixed in a molar ratio (ethanol/general formula (16)) of 5.7, and a 1.0 wt % solution was prepared by adding chloroform to the mixture. The solution was applied onto a substrate by a spin coating method, whereby a film was formed.

Example 15

A film was formed in the same manner as in Example 14 except that the molar ratio was changed to 11.3.

Example 16

A film was formed in the same manner as in Example 14 except that the molar ratio was changed to 28.3.

Example 17

The compound represented by the general formula (16) and isopropyl alcohol were mixed in a molar ratio (isopropyl alcohol/general formula (16)) of 5.9, and a 1.0 wt % solution was prepared by adding chloroform to the mixture. The solution was applied onto a substrate by a spin coating method, whereby a film was formed.

Example 18

The compound represented by the general formula (16) and acetonitrile were mixed in a molar ratio (acetonitrile/general formula (16)) of 8.7, and a 1.0 wt % solution was prepared by adding chloroform to the mixture. The solution was applied onto a substrate by a spin coating method, whereby a film was formed.

Example 19

A 1.0 wt % solution of the compound represented by the general formula (16) in toluene was prepared, and was applied onto a substrate by a spin coating method, whereby a film was formed.

Example 20

The compound represented by the general formula (16) and ethanol were mixed in a molar ratio (ethanol/general formula (16)) of 6.7, and a 1.0 wt % solution was prepared by adding toluene to the mixture. The solution was applied onto a substrate by a spin coating method, whereby a film was formed.

Example 21

The compound represented by the general formula (16) and 1-butanol were mixed in a molar ratio (1-butanol/general formula (16)) of 4.2, and a 1.0 wt % solution was prepared by adding toluene to the mixture. The solution was applied onto a substrate by a spin coating method, whereby a film was formed.

Example 22

The compound represented by the general formula (16) and toluene were mixed in a molar ratio (toluene/general formula (16)) of 7.0, and a 1.0-wt % solution was prepared by adding chloroform to the mixture. The solution was applied onto a substrate by a spin coating method, whereby a film was formed.

Films in Examples 11 to 22 each produced on a substrate 1.7 cm by 1.8 cm in size were compared with one another, and the average value of five 1 mm square points on one substrate was evaluated on the basis of the following three stages: A, B, and C. Table 2 shows the results.

(Evaluation for film quality)
A: The average number of pinholes is less than 15, and the average diameter of the pinholes is less than 100 μm.
B: The average number of pinholes is 15 or more and less than 50, and the average diameter of the pinholes is less than 100 μm.

C: The average number of pinholes is 50 or more, or the average diameter of the pinholes is 100 μm or more.

TABLE 2

| | Main solvent | Added solvent | Molar ratio (added solvent/general formula (16)) | Film quality |
|---|---|---|---|---|
| Example 11 | Chloroform | — | — | C |
| Example 12 | Chloroform | Ethanol | 1.6 | B |
| Example 13 | Chloroform | Ethanol | 7.8 | A |
| Example 14 | Chloroform | Methanol | 5.7 | A |
| Example 15 | Chloroform | Methanol | 11.3 | A |
| Example 16 | Chloroform | Methanol | 28.3 | A |
| Example 17 | Chloroform | Isopropanol | 5.9 | A |
| Example 18 | Chloroform | Acetonitrile | 8.7 | A |
| Example 19 | Toluene | — | — | C |
| Example 20 | Toluene | Ethanol | 6.7 | A |
| Example 21 | Toluene | 1-butanol | 4.2 | A |
| Example 22 | Chloroform | Toluene | 7.0 | B |

Example 23

Figure 4A:
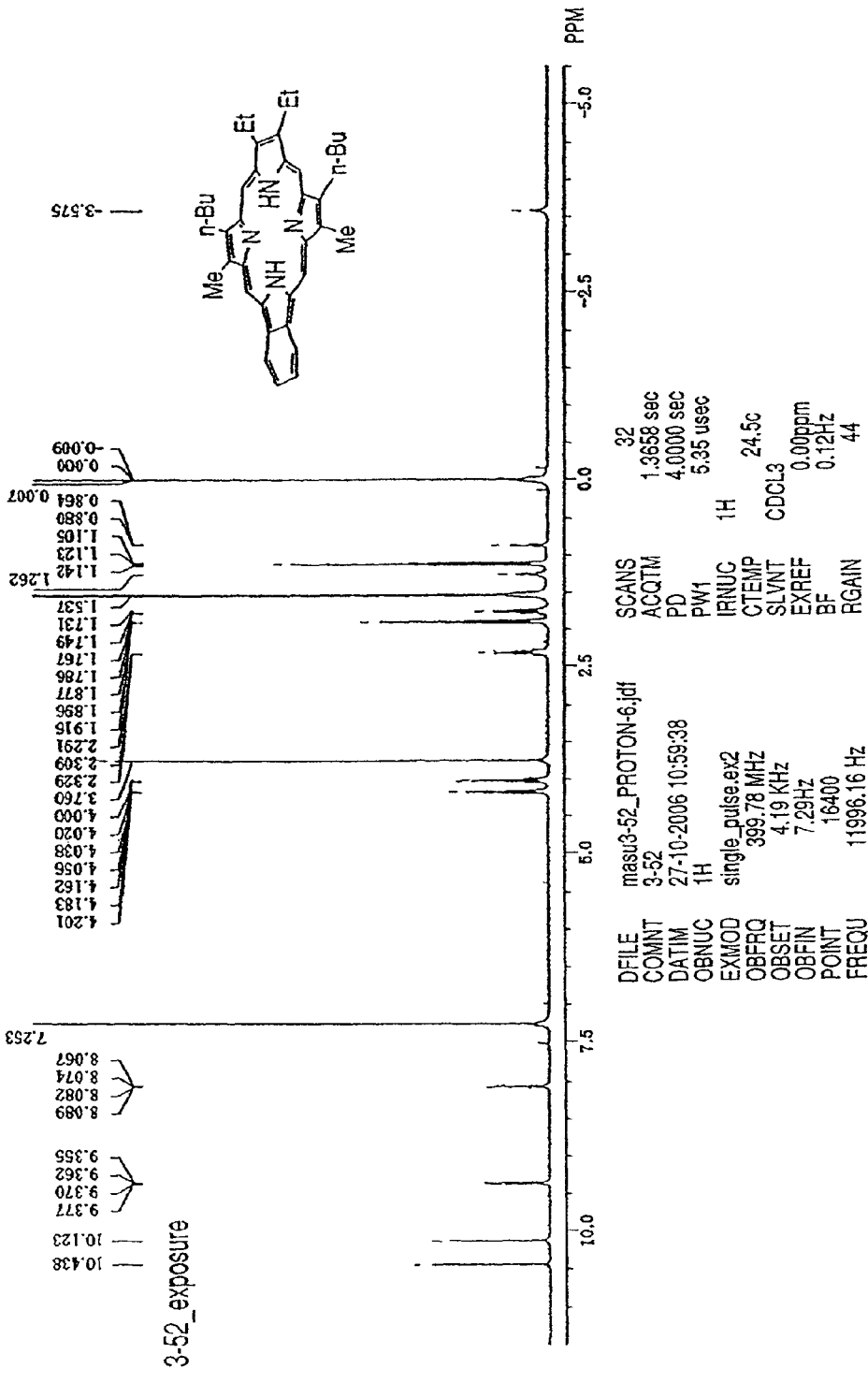
FIGS. 4A and 4B are NMR spectra of a compound from which an organic semiconductor film produced in Example 23 is formed.
Figure 4B:
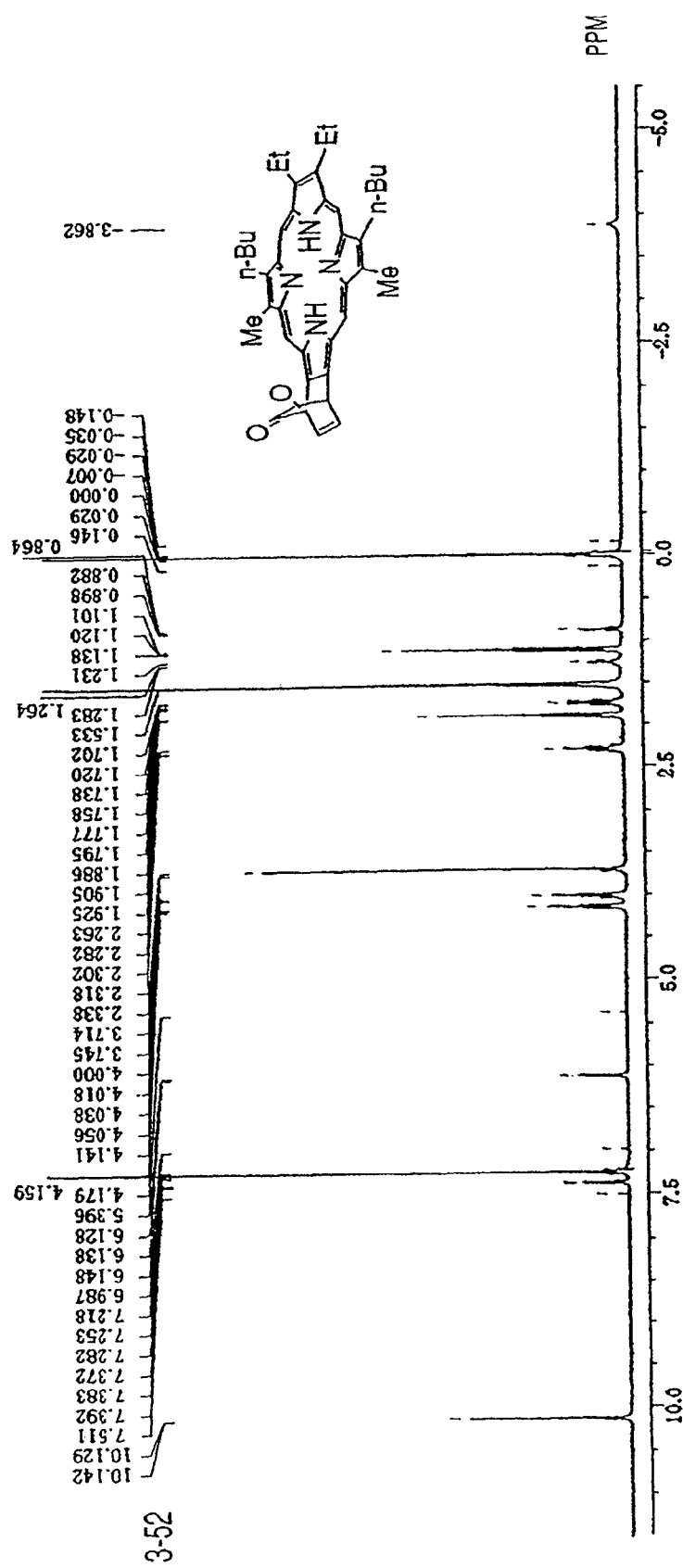

The compound represented by the general formula (e) was dissolved in deuterated chloroform, and the $^1$H-NMR of the compound was measured, whereby it was confirmed that the compound had a structure represented by the general formula (e). The sample after the measurement was irradiated with light from a metal halide lamp for 10 minutes. After that, the $^1$H-NMR of the sample was measured, whereby it was confirmed that the sample was changed to a benzo body represented by a general formula (31) obtained as a result of the elimination of a carbonyl group from the structure represented by the general formula (e). FIGS. 4A and 4B show the NMR spectra of the benzo body.

General formula (31)

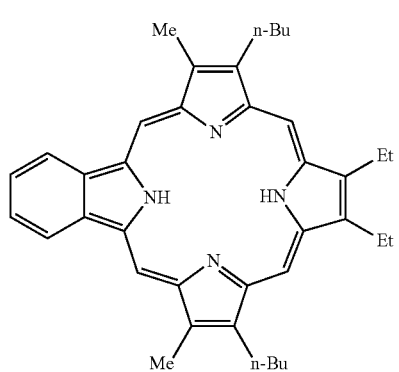

Example 24

Figure 3:
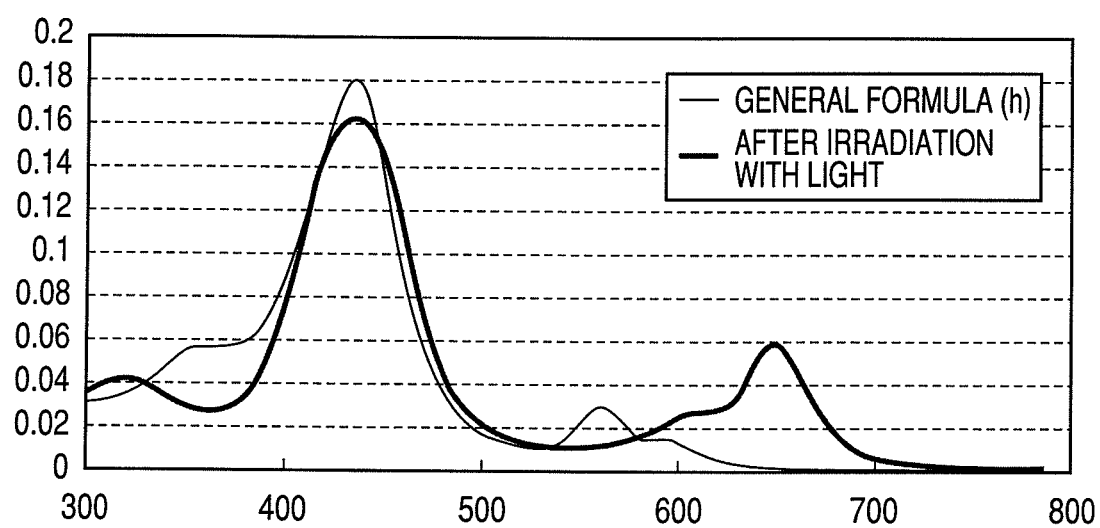
FIG. 3 is a UV spectrum of an organic semiconductor film produced in Example 24.

A solution of a zinc complex of the compound represented by the general formula (h) in acetone was prepared, and was applied onto a quartz substrate by a spin coating method at the number of revolutions of 1,000 rpm. The substrate on which a coating film had been thus formed was irradiated with light from a metal halide lamp in the air at room temperature for 5 minutes. The fact that the conversion of the compound into tetrabenzoporphyrin was attained was confirmed by measuring the UV spectrum of the film. FIG. 3 shows the UV spectrum.

Comparative Example 1

A 1 wt % solution of a compound represented by the following general formula (17) in chloroform was prepared, and was applied onto a quartz substrate by a spin coating method at the number of revolutions of 1,000 rpm. Two substrates on each of which a coating film had been thus formed were produced. One of the substrates was heated at 250° C., and the other was irradiated with light. The heated sample transformed into pentacene, whereas the sample irradiated with light did not change.

General formula (17)

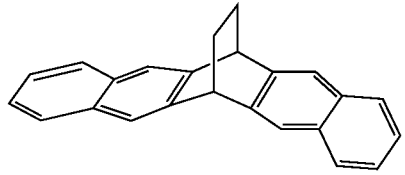

Comparative Example 2

Two substrates on each of which a coating film had been formed were produced in the same manner as in Comparative Example 1 except that a compound represented by the following general formula (18) was used. One of the substrates was heated at 200° C., and the other was irradiated with light from a metal halide lamp manufactured by NIPPON P.I. CO., LTD. (PCS-UMX250). The heated sample did not change, whereas the sample irradiated with light transformed into pentacene.

General formula (18)

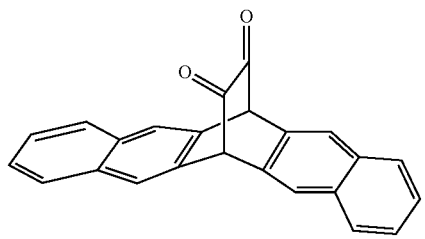

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application Nos. 2006-352555, filed Dec. 27, 2006, and 2007-232091 filed on Sep. 6, 2007 which are hereby incorporated by reference herein in their entirety.

What is claimed is:

1. A method of producing an organic semiconductor device, comprising:
an organic semiconductor layer arrangement step of providing an organic semiconductor layer on a gate insulating layer of a substrate on which a gate electrode and the gate insulating layer covering the gate electrode are arranged; and
an electrode arrangement step of providing a source electrode and a drain electrode on the organic semiconductor layer,
the organic semiconductor layer arrangement step comprising:
a precursor arrangement step of arranging a solution containing a bicyclo organic compound which is a precursor on the gate insulating layer; and
a step of subjecting the bicycle organic compound to irradiation with light, wherein the bicyclo organic compound is a compound represented by the following general formula (9):

General formula (9)

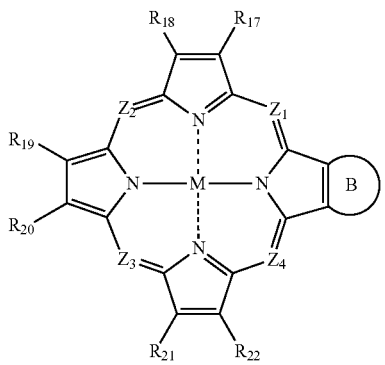

where the B ring is represented by the following general formula (27), $R_{17}$ to $R_{22}$ are each independently one selected from the group consisting of a hydrogen atom, a hydroxyl group, a halogen atom, an alkyl group, an alkoxy group, an alkylthio group, an ester group, an aryl group, a heterocyclic group, and an aralkyl group, $Z_1$ to $Z_4$ are each selected from the group consisting of a nitrogen atom and $CR_{60}$, and may be identical to or different from one another, wherein $R_{60}$ is one selected from the group consisting of a hydrogen atom and an aryl group, M represents two hydrogen atoms, a metal atom, or a metal oxide, and each pair of $R_{17}$ and $R_{18}$, $R_{19}$ and $R_{20}$, or $R_{21}$ and $R_{22}$ may be combined together to form the B ring;

General formula (27)

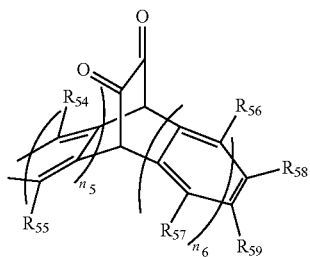

where $R_{54}$ to $R_{59}$ are each independently one selected from the group consisting of a hydrogen atom, an alkyl group, an alkoxy group, an aryl group, a heterocyclic group, an aralkyl group, a phenoxy group, a cyano group, a nitro group, an ester group, a carboxyl group, and a halogen atom, $R_{58}$ and $R_{59}$ may be coupled with each other to form a five-membered heterocyclic ring or a six-membered heterocyclic ring, and $n_5$ and $n_6$ each independently represent an integer of 0 or more.

2. A method of producing an organic semiconductor device according to claim 1, wherein the irradiation with light is performed while using a heat absorbing member, and the bicyclo organic compound is externally heated at the same time of the irradiation with light.

3. A method of producing an organic semiconductor device according to claim 2, wherein the time to perform the irradiation with light and the heating at the same time is 1 second or longer and 30 minutes or shorter.

4. A method of producing an organic semiconductor device according to claim 2, wherein the time to perform the irradiation with light and the heating at the same time is 1 minute or longer and 5 minutes or shorter.

5. A method of producing an organic semiconductor device according to claim 2, wherein heating is further performed after performing the irradiation with light and the heating.

6. A method of producing an organic semiconductor device according to claim 1, wherein all of $Z_1$ to $Z_4$ of the general formula (9) are represented by CH.

7. A method of producing an organic semiconductor device according to claim 1, wherein all of $Z_1$ to $Z_4$ of the general formula (9) are represented by a nitrogen atom.

* * * * *